US009725702B2

(12) United States Patent
Sitarz et al.

(10) Patent No.: US 9,725,702 B2
(45) Date of Patent: Aug. 8, 2017

(54) LACCASE FROM GANODERMA LUCIDUM CAPABLE OF ENHANCING ENZYMATIC DEGRADATION OF LIGNOCELLULOLYTIC BIOMASS

(71) Applicant: DANMARKS TEKNISKE UNIVERSITET, Kgs. Lyngby (DK)

(72) Inventors: Anna Sitarz, Gentofte (DK); Jørn Dalgaard Mikkelsen, Hvidovre (DK); Anne Meyer, Hellerup (DK); Mateusz Lezyk, Inowroclaw (PL)

(73) Assignee: DANMARKS TEKNISKE UNIVERSITET, Kgs. Lyngby (DK)

( * ) Notice: Subject to any disclaimer, the term of this patent is extended or adjusted under 35 U.S.C. 154(b) by 0 days.

(21) Appl. No.: 14/427,192

(22) PCT Filed: Sep. 11, 2013

(86) PCT No.: PCT/EP2013/068836
§ 371 (c)(1),
(2) Date: Mar. 10, 2015

(87) PCT Pub. No.: WO2014/041030
PCT Pub. Date: Mar. 20, 2014

(65) Prior Publication Data
US 2015/0232815 A1 Aug. 20, 2015

(30) Foreign Application Priority Data
Sep. 11, 2012 (EP) .................................... 12183917

(51) Int. Cl.
| | | |
|---|---|---|
| *C12N 9/24* | (2006.01) | |
| *C12N 9/02* | (2006.01) | |
| *C12N 9/42* | (2006.01) | |
| *C12P 19/14* | (2006.01) | |
| *C12P 19/00* | (2006.01) | |
| *C12P 7/08* | (2006.01) | |
| *C07H 21/04* | (2006.01) | |
| *C12P 19/02* | (2006.01) | |

(52) U.S. Cl.
CPC ......... *C12N 9/0061* (2013.01); *C12N 9/2437* (2013.01); *C12N 9/2445* (2013.01); *C12P 19/02* (2013.01); *C12P 19/14* (2013.01)

(58) Field of Classification Search
None
See application file for complete search history.

(56) References Cited

U.S. PATENT DOCUMENTS

2012/0107881 A1* 5/2012 Dhawan .............. C12N 9/0006
435/100

OTHER PUBLICATIONS

Bugg et al; "Pathways for degradation of lignin in bacteria and fungi", Natural Product Reports Nov. 2011, vol. 28, No. 12, Nov. 2011, pp. 1883-1896.
Database UniProt, Mar. 1, 2001, "SubName Full=Laccase;", XP002690273, retrieved from EBI accession No. UNIPROT:Q9HG17.
Ding et al; "Production and characterization of thermostable laccase from the mushroom, *Ganoderma lucidum*, using submerged fermentation", African Journal of Microbiology Research, vol. 6, No. 6, Feb. 2012, pp. 1147-1157.
Giardina et al; "Laccases: a never-ending story", CMLS Cellular and Molecular Life Sciences, Birkhäuser-Verlag, BA, vol. 67, No. 3, Oct. 22, 2009, pp. 369-385.
Jonsson L. J. et al: Detoxification of wood hydrolysates with laccase and peroxidase from the white-rot fungus *Trametes versicolor*. Applied microbiology and Biotechnology, Springer Verlag, Berlin, DE, vol. 49, No. 6, Jun. 1, 1998, pp. 691-397, XP009048784.
Joo et al; "Molecular cloning and expression of a laccase from Ganoderma lucidum, and Its antioxidative properties", Molecules and Cells, Seoul, KR, vol. 25, No. 1, Jan. 1, 2008, pp. 112-118.
Ko et al; "Purification and characterization of laccase isozymes from the white-rot basidiomycete *Ganoderma lucidum*". Applied Microbiology and Biotechnology, vol. 57, No. 1-2, Oct. 2001, pp. 98-102.
Lu et al; "An efficient system for pre-delignification of gramineous biofuel feedstock in vitro; Application of a laccase from Pycnoporus sanguineus H275". Process Biochemistry, vol. 45, No. 7, Jul. 1, 2010, pp. 1141-1147.
Martin et al; "Ethanol production from enzymatic hydrolysates of sugarcane bagasse using recombinant xylose-utilising *Saccharomyces cerevisiae*". Enzyme and Microbial Technolgy, Stoneham, MA, US, vol. 31, No. 3, Aug. 2, 2002, pp. 274-282.
Moreno et al; "Different laccase detoxification strategies for ethanol production from lignocellulosic biomass by the thermotolerant yeast *Kluyveromyces marxianus* CECT 10875". Bioresource Technology, Elsevier BV, GB, vol. 106, Nov. 25, 2011, pp. 101-109.
Apweiler R, Bairoch A, Wu CH, Barker WC, Boeckmann B, Ferro S, Gasteiger E, Huang H, Lopez R, Magrane M, Martin MJ, Natale DA, O'Donovan C, Redaschi N, Yeh L-SL. (2004) UniProt: the Universal Protein knowledgebase. Nucleic Acid Res.;32:D115-D119.
Bendtsen JD, Nielsen G, von Heijne G, Brunak S (2004) Improved prediction of signal peptides: SignalP 3.0. J. Mol. Biol 340:783-795.
Blom N, Sicheritz-Ponten T, Gupta R, Gameltoft S, Brunak S. (2004) Prediction of post-translational glycosylation and phosphorylation of proteins from amino acid sequence. Proteomics 4:1633-1649.

(Continued)

*Primary Examiner* — Iqbal H Chowdhury
(74) *Attorney, Agent, or Firm* — Michael Best & Friedrich LLP

(57) ABSTRACT

The invention addresses the need for enzymes that can enhance the yield of fermentable sugar from the hydrolysis of lignocellulose biomass, for example sugar cane bagasse, barley straw and wheat straw, such that the use of this biomass can become economically viable. The invention provides methods for the hydrolysis of biomass using a laccase derived from *Ganoderma lucidum*. Further, the invention provides an enzyme composition comprising a laccase derived from *Ganoderma lucidum* which may be combined with one or more cellulases, and for its use in enhancing lignocellulose biomass hydrolysis.

8 Claims, 11 Drawing Sheets

(56) References Cited

OTHER PUBLICATIONS

Figure 1:
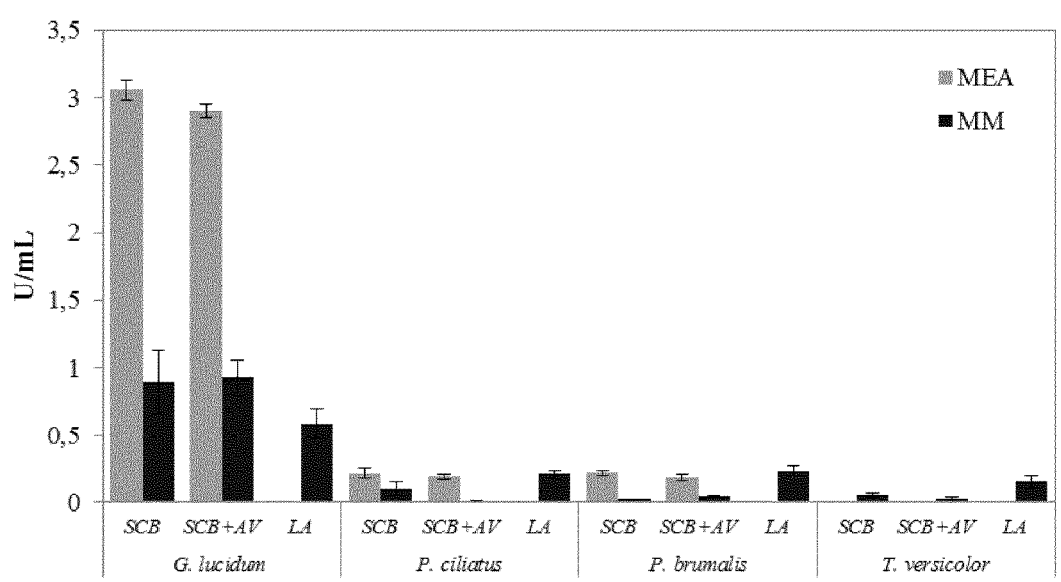

Bourbonnais R. Paice MG. (1992) Demethylation and delignification of kraft pulp by Trametes versicolor laccase in presence of 2.2'-azinobis-(3-ethylbenzthiazoline-6-sulphonate). Appl Microbiol Biotechnol. 36:823-827.
Brake et al; "A functional prepro-aloha-factor gene from *Saccharomyces cerevisiae* can contain 3, 4, or 5 repeats of the mature pheromone sequence". (1983) Mol Cell Biol 3:1440-1450.
Bulter T, Alcalde M, Sieber V, Meinhold P, Schlachtbauer C, Arnold FH. (2003) Functional expression of a fungal laccase in *Saccharomyces cerevisiae* by directed evolution. Appl Environ Microbiol.; 69(2):987-995.
Chandel AK, Kapoor RK, Singh A Kudah RC (2007) Detoxification of sugar cane bagasse hydrolysates improves ethanol production by Candida shehatae NCIM 3501. Biores Technol 98:1947-1950.
Garzillo AMV, Colao MC, Caruso C. Caporale C. Celleti D. Buonocore V. (1998) Laccase from the white-rot fungus *Trametes trogii*. Appl Microbiol Biotechnol.; 49:545-551.
Gasteiger E, Hoogland C, Gattiker A, Duvaud S, Wilkins MR, Appel RD, Bairoch A (2005) Protein identification and analysis tool on the ExPASY server. p. 571-607, In J. M. Walker (ed.), The Proteomics Protocols Handbook. Humana Press Inc., Totowa, NJ.
Gouet P, Coufcelle E, Stuart DI, Métoz F (1999) ESPript: analysis of multiple sequence alignments in PostScript. Bioinformatics 15:305-8.
Goujon et al—(2010) "A new bioinformatics analysis tools framework at EMBL-EBI". Nucl Acid Res W695-W9.
Harkin JM, Larsen MJ, Obst JR. (1974) Use of syringaldazine for detection of laccase in sporophores of wood rotting fungi. Mycologia; 66(3):469-476.
Harris PV, Weiner D, McFarland KC, Re E, Navarro Poulsen JC, Brown K, Sabo R, Ding H, Vlasenko E, Merino S, Xu F, Cherry J, Larsen S, Leggio LL (2010) Stimulation of lignocellulosic hydrolysis by proteins of glycoside hydrolase family 61: Structure and function of large, enigmatic family. Biochem 49:3305-3316.
Hoopes J, Dean JFD. (2001) Staining electrophoretic gels for laccase and peroxidase activity using 1.8-Diaminonaphthalene. Anal Biochem.; 293:96-101.
Jurado et al; "Laccase detoxification of steam-exploded wheat straw for second generation bioethanol". Bioresource Technology 100 (2009), ppf. 6378-6384.
Kumar SVS, Phale PS, Durani S, Wangikar PP (2003) Combined sequence and structure analysis of the fungal laccase family. Biotechnol Bioeng 83:386-94.
Lee SB, Taylor JW (1990) Isolation of DNA from fungal mycelia and single spores. PCR protocols: A guide to methods and applications 282-287.
Moilanen et al; "The laccase-catalyzed modification of lignin for enzymatic hydrolysis". Enzyme and Microbial Technolgy 49 (2011) pp. 492-498.
Nielsen H, Engelbrecht J, Brunak S, von Heijne G (1997) Identification of prokaryotic and eukaryotic signal peptides and prediction of their cleavage sites. Protein Eng 10:1-6.
Palmieri G. Giardina P, Bianco C, Scaloni A, Capasso A, Sannia A. (1997) A novel laccase from Pleurotus ostreatus. J Biol Chem.; 272(50):31301-31307.
Palonen et al; "Role oxidative enzymatic treatments on enzymatic hydrolysis of softwood". Wiley InterScience, Apr. 15, 2004, pp. 550-557.
Piontek, K.; Antorini, M. and Choinowski, T. (2002). Crystal structure of a laccase from the fungus *Trametes versicolor* at 1.90 Å resolution containing a full complement of coppers. The Journal of Biological Chemistry, vol. 277, No. 40, p. 37663-37669.
Ride JP. (1980) The effect of induced lignifications on the resistance of wheat cell walls to fungal degradation. Phys. Plant Pathology.; 16:187-196.
Rosgaard L, Pedersen S. Meyer AS. Comparison of different pretreatment strategies for enzymatic hydrolysis of wheat and barley straw. Appl Biochem Biotechnol (2007) 143:284-296.
Ryu S-H, Lee A-Y, Kim M (2008) Molecular characterization of two laccase from the basidiomycete fungus *Polyporus brumalis*. J. Microbiol 46(1):62-69.
Schiøt M, Rogowska-Wrzesinska A, Roepstorff P, Boomsma JJ. (2010) Leaf-cutting ant fungi produce cell wall degrading pectinase complex reminiscent of phytopathogenic fungi. BMC Biol.; 156:1-12.
Silva IR, Larsen DM, Meyer AS, Mikkelsen JD (2011) Identification, expression, and characterization of a novel bacterial RGI lyase enzyme for the production of bio-functional fibers. Enz Microb Technol 49:160-6.
Sluiter A, Hames B, Ruiz R, Scarlata C. Sluiter J, Templeton D, Crocker P. Determination of structural carbohydrates and lignin in biomass. Laboratory analytical procedure (LAP), NREL/TP-510-42618, 2011:1-15; revised Jun. 2011.
Soden DM, O'Callaghan J, Dobson ADW. (2002) Molecular cloning of laccase isozyme gene from Pleurotus sajor-caju and expression the heterologous Pichia pastoris host. Microbiol.; 148:4003-4014.
Stanke M, Morgenstern B (2005) AUGUSUS: a web server for gene prediction in eukaryotes that allows a user-defined constraints. Nuc Acid Res 33:W465-W467.
Stratton J, Chiruvolu V, Meagher M (1999) High-well density fermentation. In: Higgins D, Gregg J, editors. Pichia protocols, vol. 103. Totowa, NJ., USA: Humana Press p. 109-20.
Sun et al; "Secretory expression and characterization of a soluble laccase from the Ganoderma lucidum strain 7071-9 in Pichia pastoris". Mol Biol Rep (2012) 39, pp. 3807-3814.
Sørensen A, Teller PJ, Hilstrøm T, Ahring BK (2008) Hydrolysis of Miscanthus for bioethanol production using dilute acid presoaking combined with explosion pre-treatment and ezymatic treatment. Biores Technol 99(14):6602-6607.
Sørensen HR, Meyer AS, Pedersen S., (2003) Enzymatic hydrolysis of water-soluble wheat arabinoxylan. I. Synergy between • -L-arabinofuranosidases, endo-1,4-• -xylanase, and • -xylosidase activities. Biotechnol Bioeng 81:726-731.
Ters T, Kuncinger T, Srebotnik E., (2009) Carboxylic acids used in common buffer systems inhibit the activity of fungal laccases. J Mol Cat B:Enz 61:261-267.
Thaysen-Andersen M, Mysling S, Højrup P., (2009) Site-specific glycoprofiling of N-linked glycopeptides using MALDI-TOF MS: Strong correlation between signal strength and glycoform quantities. Anal Chem.; 81:3933-3943.
Thurston CF., (1994) The structure and function of fungal laccases. Microbiol 140:19-26.
Wang et al; "A laccase from the medicinal mushroom *Ganoderma lucidum*". Appl. Microbiol Biotechnol (2006) 72, pp. 508-513.
Wolfenden BS, Willson RL. (1982) Radical-cations as reference chromogens in kinetic studies of one-electron transfer reactions: Pulse radiolysis studies of 2.2'-azinobis-(3-ethylbenzthiazoline-6-sulphonate). J Chem Soc Perkin Trans.;II:805-812.
Xu F, Shin W, Brown SH, Wahlethner JA, Sundaram UM, Solomon EL. (1996) A study of a series of recombinant fungal laccases and bilirubin oxidase that exhibit significant differences in redox potential, substrate specificity, and stability. Biochimica et Biophysics Acta.; 1292:303-311.

\* cited by examiner

LACCASE FROM GANODERMA LUCIDUM CAPABLE OF ENHANCING ENZYMATIC DEGRADATION OF LIGNOCELLULOLYTIC BIOMASS

CROSS-REFERENCE TO RELATED APPLICATIONS

This is a U.S. national stage entry of International Patent Application No. PCT/EP2013/068836, filed on Sep. 11, 2013, which claims priority to European Patent Application No. 12183917.9, filed on Sep. 11, 2012, the entire contents of all of which are fully incorporated herein by reference.

BACKGROUND OF THE INVENTION

Lignocellulosic materials, such as agro-industrial residues (sugarcane bagasse) or forestry are an important source of renewable biomass for the biofuel industry; Lignocellulose comprises cellulose, hemicellulose, and lignin, where lignin functions as a cementing agent between cellulose and hemicellulose fibers, protecting them from microbial and enzymatic attack. Lignin is a complex, aromatic biopolymer consisting of phenolic units mainly p-hydroxyphenyl, guaiacyl, and syringyl-type phenylpropane, which are linked together by ether and carbon-carbon bonds. Sources of lignocellulose biomass include SugarCane Bagasse (SCB); barley straw and wheat straw.

SCB is a fibrous residue of cane stalks that is left over after the crushing and extraction of the sugar rich juice from sugarcane (*Saccharum officinarium*). SCB mainly consist of cellulase 51% (w/w), hemicellulose 23% (w/w), and insoluble lignin 22% (w/w), and may be used as a source of cellulosic ethanol production.

The utilization of lignocellulose, such as SCB, barley and wheat straw, for biofuel production is hampered by difficulties faced in degrading these recalcitrant substrates, where the presence of lignin in the lignocellulose materials is suggested to retard the cellulases during their enzymatic hydrolysis of cellulose. Pre-treatment of the lignocellulose biomass is used to partially solubilize the biomass and thereby enhance the accessibility of the cellulose to enzymatic attack. Steam Explosion (STEX) uses a combination of high-pressure steam, followed by an explosive decompression, to partially hydrolyze hemicelluloses, which also serves to temporarily solubilize and relocate lignin, thereby increasing the accessibility of the remaining cellulose. The addition of an acid catalyst prior to steam treatment is commonly used to increase hydrolysis of hemicelluloses. However, residual lignin in the treated biomass is known to non-specifically bind to hydrolytic enzymes, thereby reducing the efficiency of cellulose hydrolysis. Steam treatment of biomass, particularly acid treated biomass, also releases inhibitory compounds, including phenolic compounds that can both inhibit enzymatic hydrolysis of cellulose to glucose and its subsequent fermentation to produce alcohol.

Laccase treatment of steam treated biomass has been investigated for its ability to improve the down-stream processing of biomass to produce fermentable sugars and alcohol. Laccase (benzenediol: dioxygen oxidoreductases; EC 1.10.3.2) is a blue copper containing enzyme, which catalyzes the removal of an electron and a proton from phenolic hydroxyl or aromatic amino groups to form free phenoxy radicals and amino radicals, respectively. During this reaction, one molecule of atmospheric oxygen is reduced to two molecules of water. Laccase, acting via a mediator, is also able to oxidize non-phenolic lignin units ($C_4$-esterified) to radicals.

Treatment of steam-pretreated softwood with a laccase from *Trametes hirsuta* is reported to improve its enzymatic hydrolysis, however the efficacy of laccase treatment was partly dependent on the presence of the mediator, N-hydroxy-N-phenylacetamide (Palonen and Viikari, 2004). Two laccase enzymes, isolated from *Cerrena unicolor* and *Trametes hirsuta*, are reported to enhance cellulose hydrolysis of steam-treated spuce wood, but to inhibit cellulose hydrolysis of steam-treated giant reed (Moilanen et al., 2011). Treatment of steam-exploded wheat straw with laccase is reported to cause lignin polymerization, which may contribute to detoxification of the products released by stream treatment (Jurado et al., 2009). However, these investigators report that treatment with *Coriolopsis rigida* laccase when performed prior to enzymatic hydrolysis of cellulose actually reduced the recovery of glucose, which was attributed to the release of phenolic compounds by laccases that inhibit cellulases. The investigators comment that contradictory results are reported with respect to laccase treatment, and they conclude that detoxification methods must be studied independently for each pretreated material.

There exists a large industrial interest in identifying new sources of enzymes that can efficiently degrade lignin, and enhance glucose release during lignocellulose degradation (hydrolysis). A search for phylogenetically-related laccases reveals that a large number of different laccases are produced by white-rot fungi (*Basiodiomycota*). *Ganoderma lucidum* (*lingzhi*) is one of the many members of the white-rot fungi. It is well known as a medicinal mushroom in traditional Chinese medicine and is commonly used for pharmaceutical purposes and in health foods.

A laccase gene GLlac1, encoding a GLlac1 laccase, has been cloned from *Ganoderma lucidum* (strain 7071-9 monokaryon) and expressed in *Pichia pastoris*. The expressed laccase is reported to confer anti-oxidative protection from protein degradation, with potential biomedical applications (Joo et al., 2008). GLlac1 laccase, when expressed from a synthetic gene GILCC1 in *Pichia pastoris*, has a Km of 0.995 mM, a pH optimum of 2.6 and is reported to be useful for the removal of color from reactive textile dye effluent (Sun et al., 2012). A laccase, has been isolated from *Ganoderma lucidum* fruiting bodies, having a molecular mass of 75 kDa, and the N-terminal sequence, GQNGDAVP, and is reported to be capable of inhibiting HIV-1 RT (Wang and Ng, 2006). A laccase, isolated from *Ganoderma lucidum* and reported to be useful in paper-making, is disclosed in CN1657611A.

Efficient use of lignocellulose biomass, in particular sugarcane bagasse, as a renewable source of bioethanol is dependent on the provision of individual lignocellulose modifying and degrading enzymes that in combination with optimal pre-treatment steps can maximize fermentable sugar yields. Chandler et al 2007 report that detoxification of sugarcane bagasse hydrolysate using a laccase isolated from *Cyathus stercoreus* NCIM 3501 can improve ethanol fermentation by *Candida shehatae*. There remains a need however, to provide enzymes that can enhance the yield of fermentable sugar yields from biomass, in particular steam exploded sugar cane bagasse, such that the use of this biomass can become economically viable.

SUMMARY OF THE INVENTION

The invention provides a fungal laccase (EC 1.10.3.2) comprising a polypeptide, wherein the amino acid sequence of the polypeptide is at least 499 amino acid residues in length and has at least 92% amino acid sequence identity to SEQ ID NO: 5.

The fungal laccase of the invention may additionally comprise a homologous or heterologous amino-terminal signal peptide. In one embodiment the fungal laccase polypeptide is at least 520 amino acid residues in length, comprising a homologous signal peptide, and having at least 92% amino acid sequence identity to SEQ ID NO: 9. In one embodiment the fungal laccase polypeptide additionally comprises a heterologous carboxy-terminal peptide and wherein the peptide has selective substrate binding affinity suitable for purification of the polypeptide.

The invention provides a DNA molecule comprising a positive DNA strand having a nucleic acid sequence encoding the fungal laccase of the invention. The DNA molecule may further comprises a DNA promoter, wherein the nucleotide sequence of the promoter is operably linked to nucleic acid sequence encoding the fungal laccase. In one embodiment the DNA molecule encoding the fungal laccase has a nucleic acid sequence of SEQ ID NO: 6 or 8.

The invention provides a recombinant host cell comprising the DNA molecule encoding the fungal laccase of the invention. The DNA molecule is either integrated into the genome of the host cell or is integrated into a plasmid located in the recombinant host cell. The recombinant host cell is prokaryotic or eukaryotic cell, selected from among a bacterial cell, a yeast cell and a fungal cell.

The invention provides a method for producing the fungal laccase of the invention, comprising:
a. culturing a recombinant host cell in a cultivation medium, wherein the cell comprises a DNA molecule, the DNA molecule comprising a nucleic acid sequence encoding the fungal laccase according to the invention, and
b. recovering the fungal laccase expressed by the host cell in step a) from the cultivation medium.

The invention provides a method for enhancing enzymatic hydrolysis of lignocellulose biomass, comprising the steps of:
a. providing an aqueous dispersion of biomass;
b. adding a preparation of fungal laccase to the biomass (a);
c. adding a preparation of one or more cellulose hydrolysing enzyme to the biomass (b), wherein the addition in step b) is either simultaneous with the addition in step c), or is prior to the addition in step c);
d. incubating the biomass of step b) and step c) either simultaneously or in sequence, wherein the method optionally includes the step of:
e. separation of soluble biomass from the product of step d) in order to obtain a soluble aqueous hydrolysate; and
wherein the fungal laccase is a polypeptide having at least 85% (or at least 90%) amino acid sequence identity to SEQ ID NO: 5.

In one embodiment of the above method, the biomass may be pre-treated with one or more of heat, pressure and steam in order to partially degrade and solubilize the lignocellulose. For example the biomass may be Sugarcane Bagasse, preferably Sugarcane Bagasse pretreated with steam explosion.

In one embodiment of the above method, step (d) is performed at a pH of between 4.2 and 5.2. Additionally, step (d) can for example be performed at a temperature of between 40° C. and 50° C. Additionally, the incubation of step (d) may have a duration of 16 hours or more step, for example 24 or 30 hours.

The invention provides an enzyme composition suitable for enhancing enzymatic hydrolysis of lignocellulose biomass in the method of the invention, comprising a fungal laccase wherein the fungal laccase is a polypeptide having at least 85% amino acid sequence identity to SEQ ID NO: 5.

In one embodiment, the enzyme composition further comprises one or more cellulose degrading enzyme. The one or more cellulose degrading enzyme may be selected from one or more of an endo-β-1,4-glucanase (EC 3.2.1.4), exo-glucanase (EC 3.2.1.91) and β-glucosidase (EC 3.2.1.21).

In one embodiment the fungal laccase in the enzyme composition is a recombinant polypeptide obtained by recombinant expression in a host cell selected from any one of *Aspergillus niger, Aspergillus tubigensis, Aspergillus awamori, Trichoderma reesei, Penicillium funiculosum, Hansenula polymorpha Bacillus subtilis, Bacillus licheniformis*, and *Escherichia coli*; where the polypeptide may include a heterologous carboxy-terminal peptide having selective substrate binding affinity suitable for purification of the polypeptide.

In one embodiment the enzyme composition may be formulated as a dry powder or a dry tablet or alternatively as a liquid.

The invention additionally provides for the use of an enzyme composition according to the above embodiments for enhancing cellulase-mediated hydrolysis of lignocellulose biomass.

DEFINITIONS

Vector: is a DNA molecule used as a vehicle to transfer genetic material into a host cell. Vectors may be plasmids, which have an origin of replication for at least one host cell, a cloning site for inserting genetic material, and optionally a gene encoding a selectable marker.

FIGURE LEGENDS

FIG. 1. Comparison of laccase activity expressed by four white-rot fungi (*Ganoderma lucidum, Polyporus brumalis, Polyporus ciliatus* and *Trametes versicolor*) grown on malt extract (MEA) or minimal medium (MM) supplemented with SCB, SCB+AV or LA. Laccase activity could not be determined for *T. versicolor* grown on MEA. Laccase activity was defined as the amount of enzyme required to oxidize 1 μmol of syringaldazine per minute at 30° C. and pH 6.5. Oxidation of syringaldazine was monitored spectrophotometrically at 530 nm ($\epsilon_{530}$=65000 M$^{-1}$cm$^{-1}$, (Lin, Lloyd, 2006)) for 10 min. The assay mixture contained: 100 mM phosphate buffer (2.2 mL, pH 6.5), syringaldazine (0.3 mL, 0.216 mM) and a pre-diluted fungal crude extract (0.5 mL) that ensured the linear range of Michaelis-Menten kinetics. The pre-diluted fungal crude extracts were filtered through 0.45 μm filter (MiniSart-plus, sterile, Sartorius, Germany) prior to activity measurements.

Figure 2:
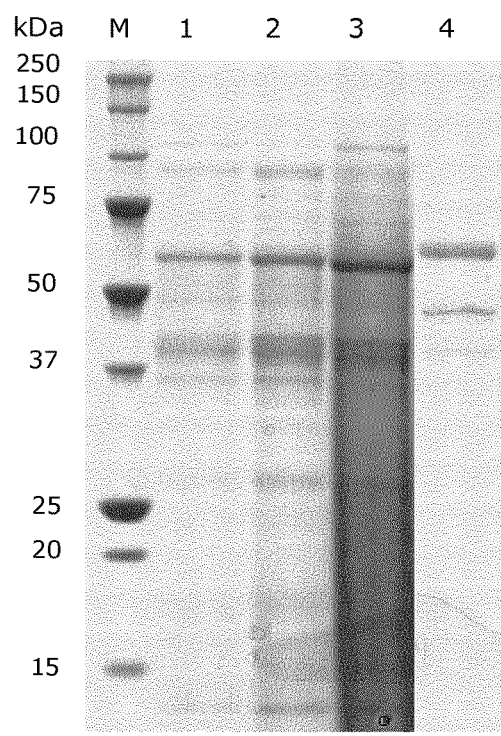

FIG. 2. SDS-PAGE electrophoresis of *Ganoderma lucidum* crude protein extract. Expressed proteins in the fungal crude extract were evaluated by Sodium Dodecyl Sulphate polyacrylamide (SDS-PAGE) electrophoresis, using a Criterion XT gel system (Bio-Rad, CA, USA). The protein samples (65 μL) were diluted in XT sample buffer (25 μL, cat. no. 161-0791) and 500 mM dithiothreitol (10 μL, Sigma Aldrich, Germany). The samples were boiled at 95° C. for 5 min before being loaded into a 10% separation gel (cat. no. 345-0118). Electrophoresis was carried out at a constant voltage of 125 V for 2 h using 5 times diluted XT MOPS as the running buffer (cat. no. 161-0788). The separated proteins were visualized by staining with Coomassie Blue G-250 (cat. no. 161-0786). Estimation of Molecular Weights (MW) of the proteins was made against molecular (stained) standards (250, 150, 100, 75, 50, 37, 25, 20, 15, 10 kDa) (cat. no. 161-0374). All chemicals used during SDS-PAGE were purchased from Bio-Rad, CA, USA.

Wells in the gel represent; protein marker (M), laccase protein from *Trametes versicolor*, Cat. no. 51639, Sigma Aldrich, Germany (4); and protein crude extract from *Ganoderma lucidum* groan on MEA medium supplemented with either SCB (1), SCB+AV (2), or LA (3).

Figure 3:
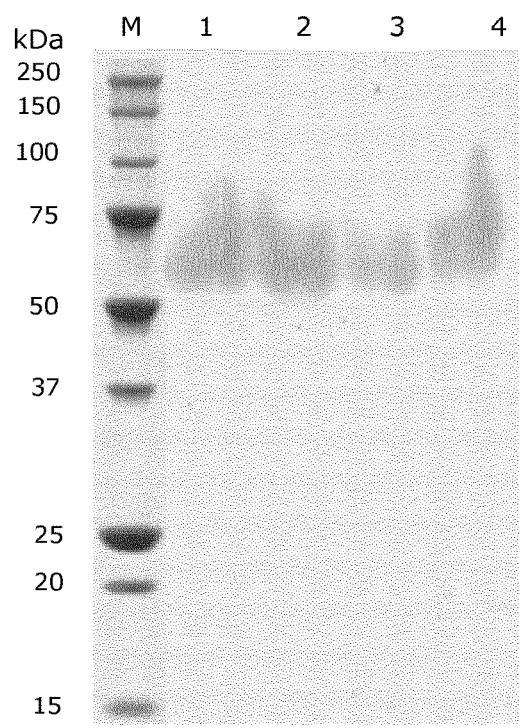

FIG. 3. Native-PAGE electrophoresis of *Ganoderma lucidum* crude protein extract. Freeze-dried supernatant samples were mixed in a ratio 1:1 with XT sample buffer, containing no reducing agents, and loaded onto a Zymogram gel (cat. no. 345-0080) without thermal denaturation. Running buffer and protein standards were the same as for SDS-PAGE (FIG. 2). The separated proteins were visualized by incubating the gel in a 50 mM sodium acetate buffer (pH 5) containing: dimethyl sulfoxide (1%) and DAN (1.8-diaminonaphthalene) solution (2 mM) as substrate.

Wells in the gel represent protein marker (M), laccase protein from *Trametes versicolor*, Cat. no. 51639, Sigma Aldrich, Germany (4) and *Ganoderma lucidum* grown on MEA medium supplemented with either SCB (1), SCB+AV (2), or LA (3).

Figure 4:
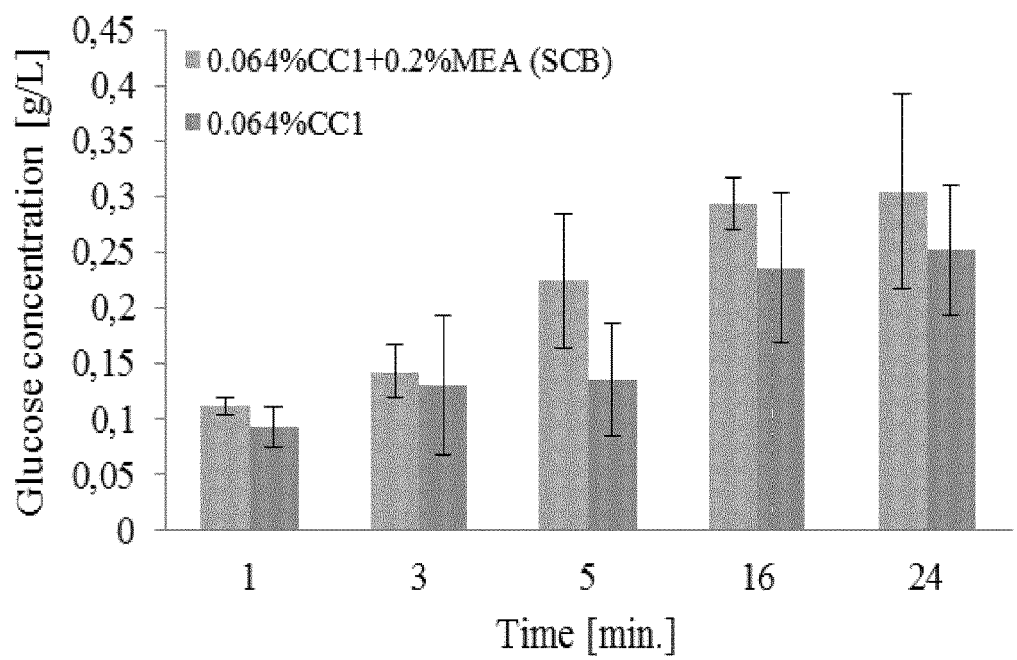
Figure 4:
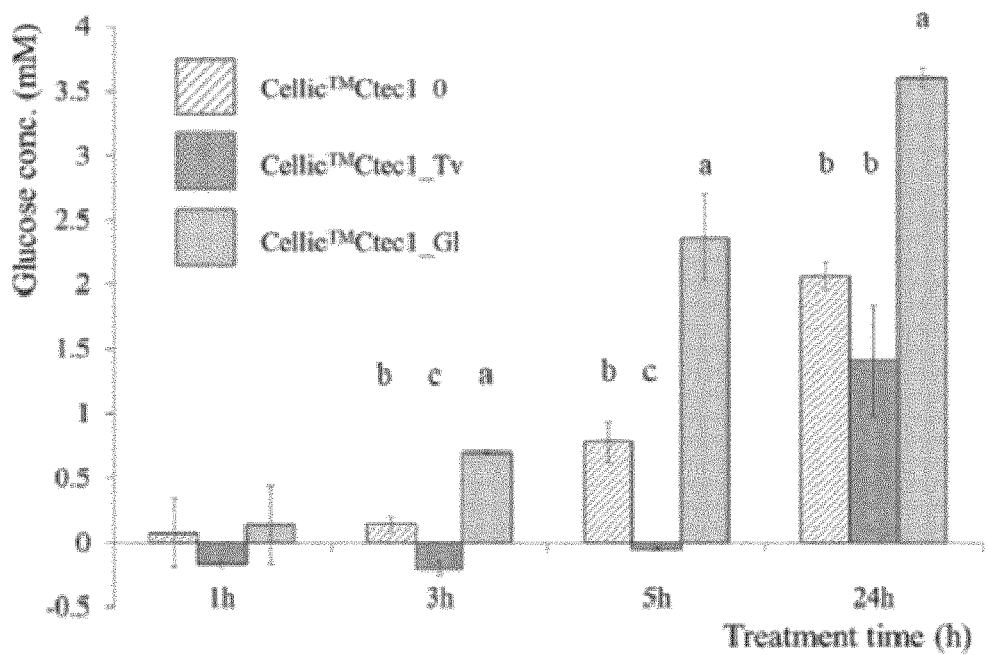

FIG. 4. Effect of *Ganderma lucidum* laccase on the hydrolysis of steam exploded Sugar Cane Bargasse (STEX-SCB) and glucose release by Cellic® CTec1 as compared to a *Trametes versicolor* laccase.

A: A graphical comparison of glucose (g/L) released over time during hydrolysis of STEX-SCB at pH 5.1 and 50° C. by the enzyme preparation Cellic® CTec1 (CC1) alone, and in combination with crude protein extract from *Ganoderma lucidum* grown on MEA (SCB). The effect of glucose release during a laccase-cellulase catalyzed hydrolysis of 5% (w/v) dry matter of pretreated SCB was evaluated in 0.1 M citrate-phosphate buffer pH 5.1 and 50° C. (optimal for the cellulase preparation).

B: A graphical comparison of yields of glucose equivalents (mM) (based on reducing ends measurement) released over time during hydrolysis of 0.8% (w/v (DM)) STEX-SCB at pH 4.8 and 50° C. by the enzyme preparation CC1 alone (Cellic™ CTec1 0); in combination with commercially obtained laccase from *Trametes versicolor* (Cellic™ CTec1_Tv); and in combination with a crude protein extract from *Ganoderma lucidum* (grown on MEA SCB) (Cellic™ CTec1_GI).

The data shown in Figure A and B were obtained using the commercially available cellulase cocktail preparation Cellic®CTec1 (0.064% Enzyme/Substrate ratio (E/S), w/w; Novozymes, Denmark) with combination of a laccase-rich broth from *Ganoderma lucidum* or *Trametes versicolor* laccase (0.4% E/S, w/w). The hydrolysis reactions were sampled after 0, 1, 3, 5, 16, and 24 hours and the reaction stopped by incubation at 99° C. for 15 min. The samples were then centrifuged at 10.000 rpm for 2 min, the supernatants were filtered through 0.2 μm filter and the yields of released glucose were quantified using D-glucose-HK kit (Megazyme, Denmark) at 340 nm in an Infinite 200 microtiter plate reader (Tecan, Salzburg, Austria). Glucose yields released over time were corrected for the glucose present in the hydrolysis sample at time 0. E/S dosage was based on the total protein concentration used. Cellic®CTec1 comprises the *Trichoderma reesei* cellulase complex (exo-glucanase, endo-glucanase, and β-glucosidase activities) with additional β-glucosidase and glycoside hydrolase family 61 hydrolyse boosting proteins (Harris, 2010). All determinations of the enzymatic hydrolysis samples were performed in duplicates, pooled standard deviations ranged from 0.04-0.26. Protein quantification was performed using the Pierce BCA (Bi Cinchoninic Acid) protein assay kit microplate procedure according to manufacturer's instructions (Thermo Fisher Scientific, Rockford, US) as described before (Silva, et al. 2011). BSA was used as a standard.

Figure 5:
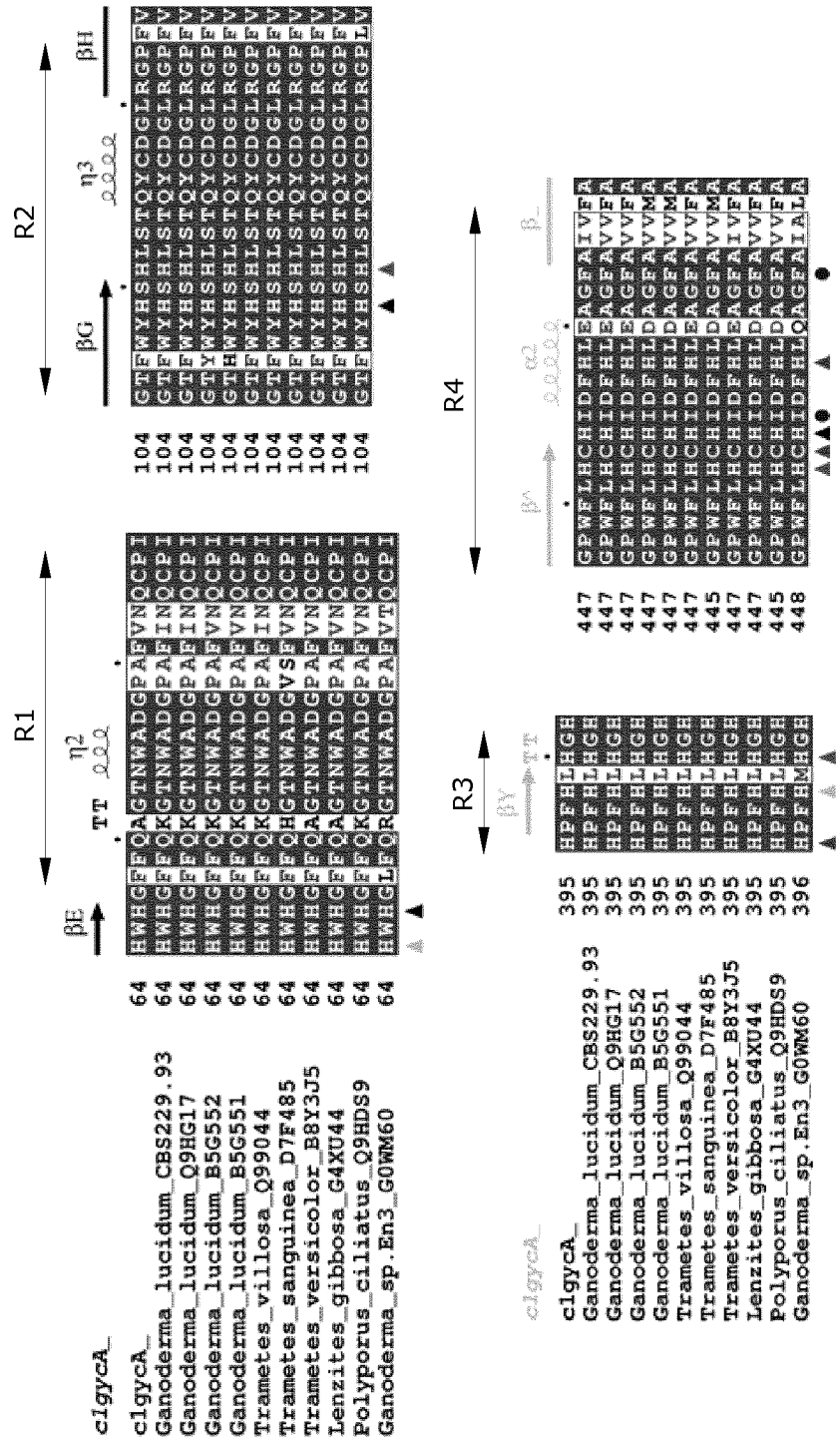

FIG. 5. The ungapped amino acid sequence of selected peptide regions (R1-R4) within the LacGL1 laccase polypeptide are aligned with the corresponding peptide regions of other fungal laccases belonging to the multicopper oxidases family. The copper binding domains with their conserved amino acids that take part in coordination to four copper atoms, located in the selected peptides regions are indicated. Amino acids in red boxes indicate fully conserved residues and triangles below the red boxes identify 11 fully conserved amino acids coordinating to the four copper atoms, which allow these fungal laccases to be distinguished within a broader class of multicopper oxidases. Red, green, pink, and black triangles indicate coordination to the T1Cu, T2Cu, T3αCu, and T3βCu copper ions, respectively. The blue circles indicate the residues positioned 4 Å axial to the T1 copper ion. Note that the axial, non-coordinating isoleucine (4551) and phenylalanine (463F) are invariable among the selected fungal laccases. The secondary structures (α-helices and β-sheets) above the alignment are based on a crystallographic structure of *Trametes versicolor* (PDB ID: 1GYC) (Piontek et al., 2002). α-helices and β-sheets colored black and green indicate domain 1 (residues 1-131, and 476-499), and domain 3 (residues 301-475), respectively. Domain 2 (residues 132-300) is not presented here due to the lack of residues serving a function in catalysis. Alignment of sequences was made using ClustalW 2.0 software (Goujon et al., 2010) and ESPript for final output (Gouet et al., 1999). The signal peptides were cleaved off prior to alignment using SignalP software.

Figure 6:
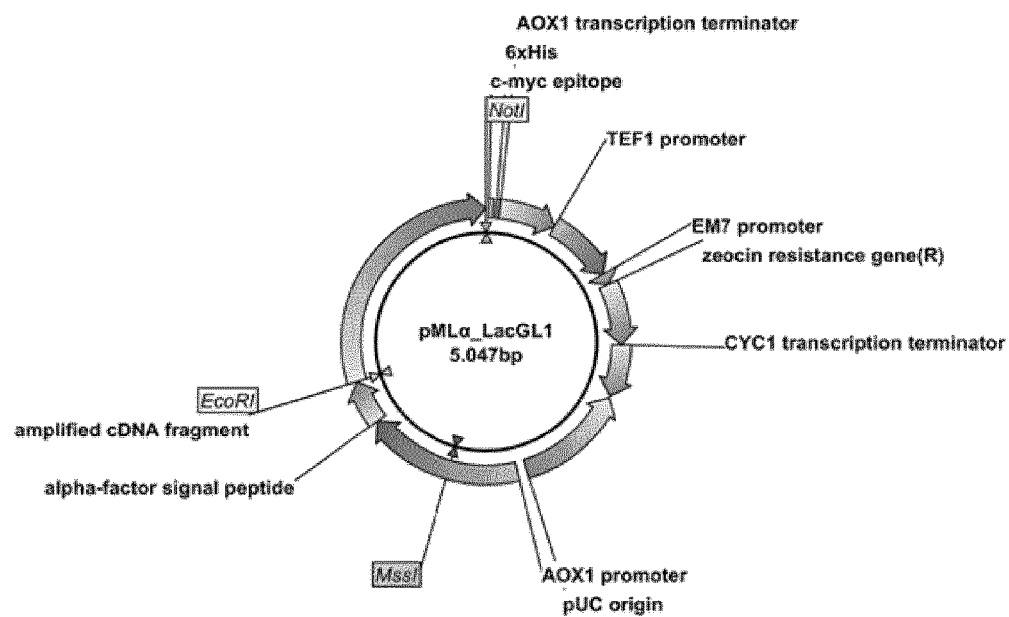

FIG. 6. The map of the recombinant plasmid pMLα_LacGL1 used for expression of the LacGL1 laccase in *Pichia pastoris* X-33. The pMLα_LacGL1 vector contains a sequence encoding for the signal peptide from *Saccharomyces cerevisiae* α-mating factor pre pro peptide fused in-frame to LacGL1 with a HIS tag and c-myc epitope fused at the C-terminus.

Figure 7:
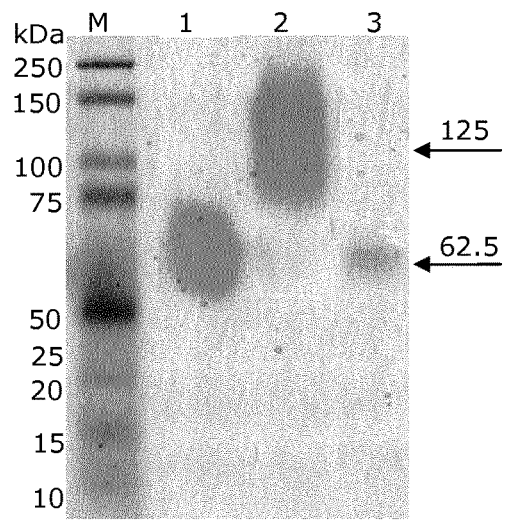

FIG. 7. The activity staining of native and recombinantly expressed LacGL1 laccase on Native PAGE, with and without EndoH treatment. (M) molecular weight standards, (1) the laccase from a crude extract of *G. lucidum* CBS229.93, (2) the LacGL1 laccase expressed in *Pichia pastoris*, (3) the LacGL1 laccase expressed in *P. pastoris* after EndoH treatment. The Native PAGE gel was submerged in 49 mL of 0.1 M citrate-phosphate and 1 mL ABTS (4 mM) to visualize the activity staining of laccase. The EndoH (endoglycosidase) treatment of the LacGL1 laccase was performed for 24 h, according to New England Biolabs procedure (Ipswitch, Mass., The USA).

Figure 8:
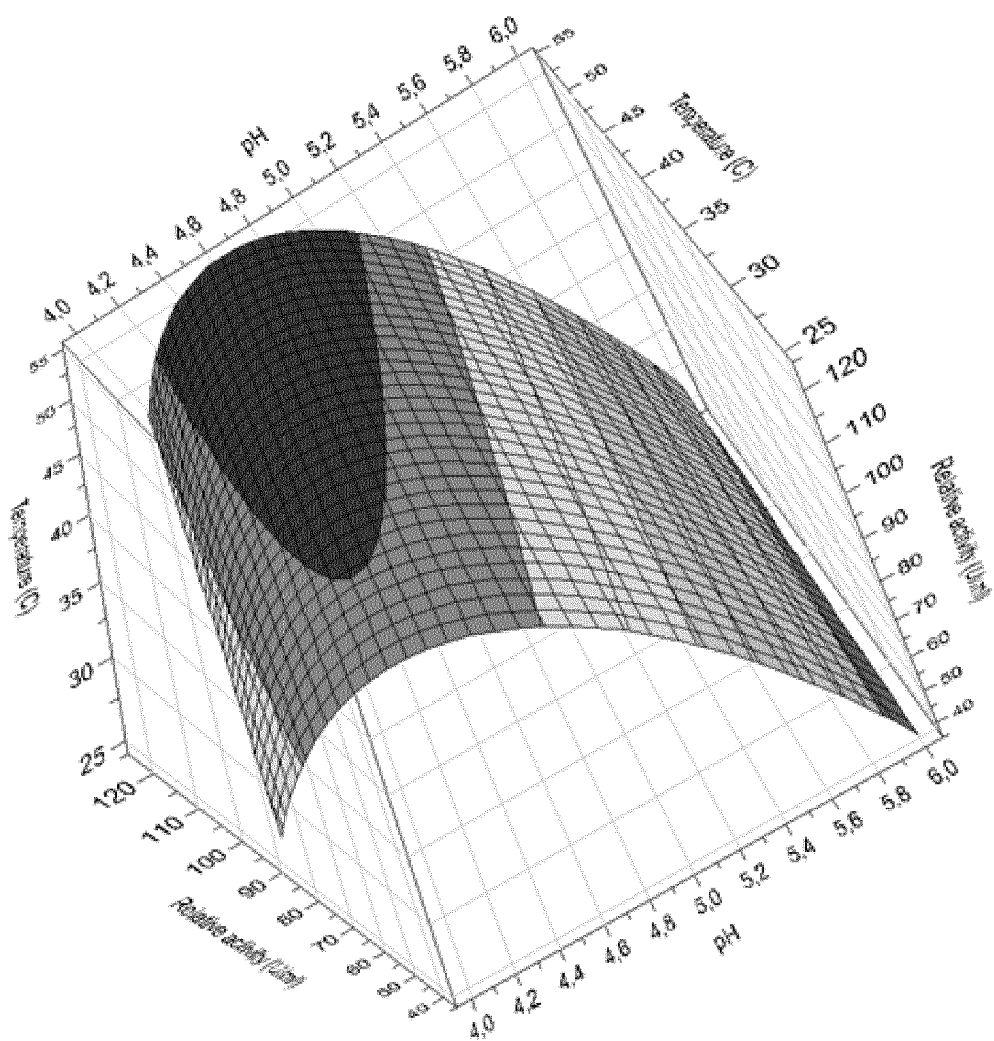

FIG. 8. A surface response plot of the relative activity (U/mL) of the LacGL1 laccase expressed in *Pichia pastoris* as a function of pH and temperature. The effect of the pH and temperature on the LacGL1 laccase activity, expressed from *P. pastoris*, was modeled via randomized, full factorial, statistically designed experiment—MODDE program version 7.0.0.1 (Umetrics, Umeå, Sweden). The statistical design consisted of 12 experiments, including a triplicate repetition at the center point (pH 5 and 40° C.), using ABTS as a substrate. The influence of the temperature and pH was monitored between 25-55° C. and pH 4-6 (for 0.1 M citrate-phosphate buffer), respectively. The mixture with the ABTS and buffer at the defined pH value was incubated for 5 min. in a thermocycler set to a desired temperature and afterwards added to a previously pre-diluted enzyme in a microtiter plate which was incubated for 1 min. in a microtiter plate reader set to a desired temperature. After mixing the substrate and buffer with the enzyme, the initial rate of the product formation was measured as described above. The volumes and concentrations of enzyme, substrate, and buffer were identical as for the laccase activity assay.

Figure 9:
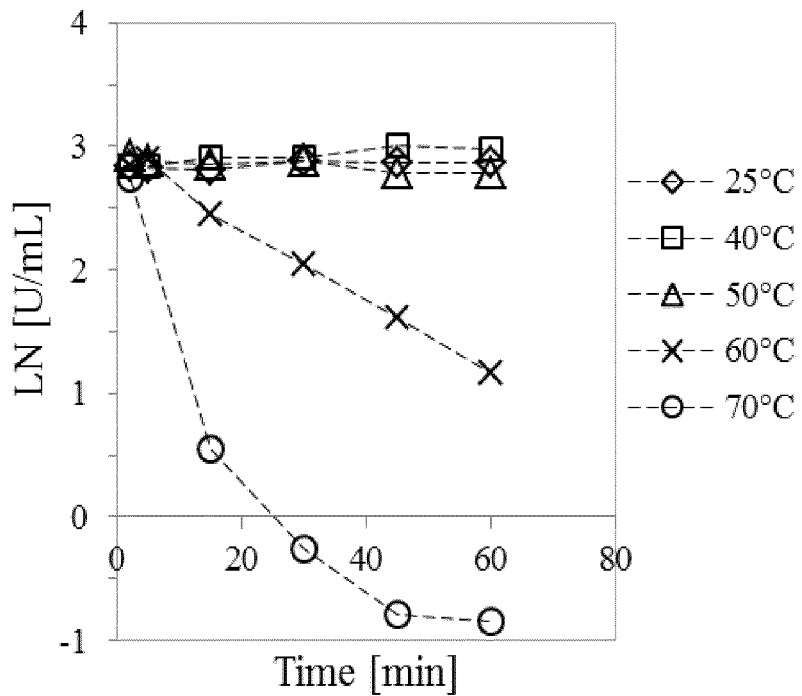

FIG. 9. The temperature stability profile of LacGL1 laccase as a function of LN [U/mL] vs. incubation time at pH 4.7 and 0.1 M citrate-phosphate buffer. The highest impact on the rate of product formation under optimal pH conditions and incubation time at a specific temperature profile was observed for temp 60° C. and 70° C., respectively. The relative difference between single measurements was <5%.

Figure 10:
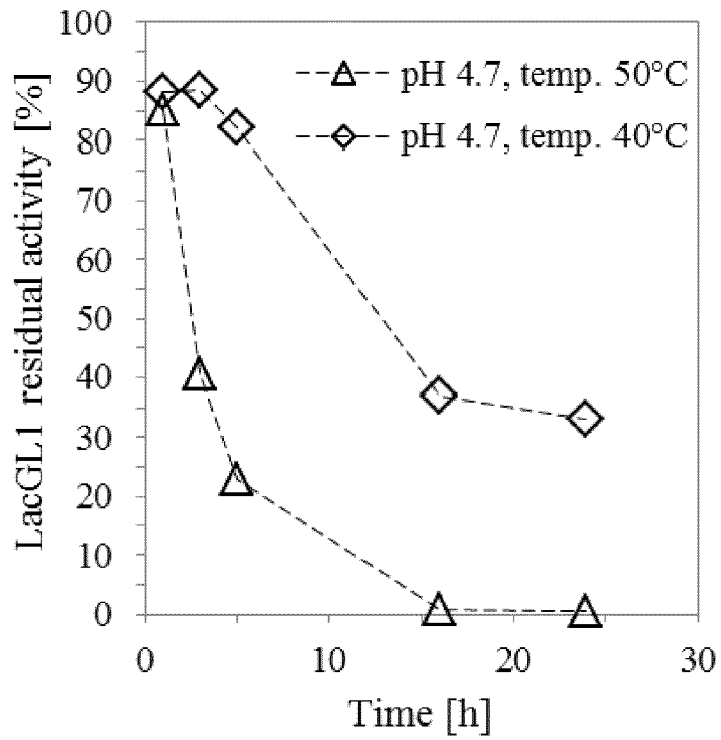

FIG. 10. LacGL1 laccase stability evolution plot at optimum pH of 4.7 and two different temperature values (40° C. and 50° C.). Since the plot is a continuation of temperature stability plot (FIG. 9), the first measurement is given after 1 h. Laccase residual activity [%] is calculated based on activity value of laccase measured at pH 4.7 and 25° C. The relative difference between single measurements was <5%.

Figure 11:
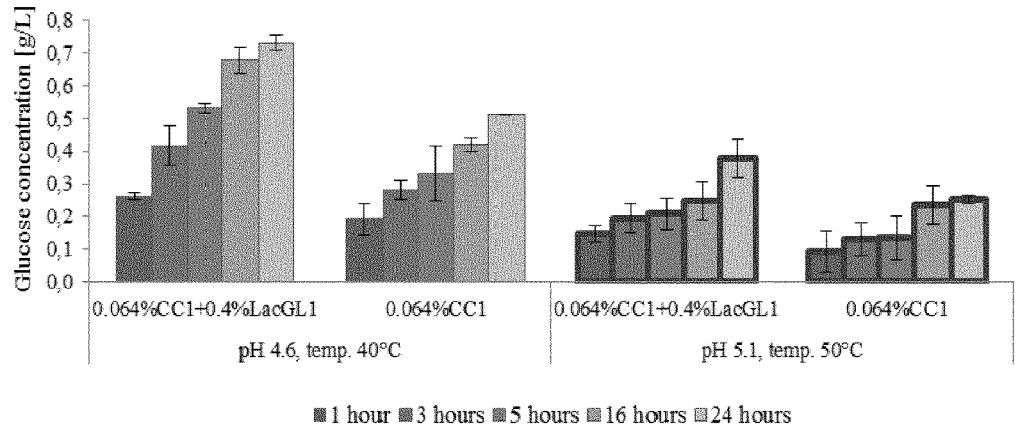

FIG. 11. A graphical comparison of yields of released glucose over time in LacGL1-Cellic® CTec1 catalyzed hydrolysis STEX-SCB at different pH and temperatures. The cellulase preparation is Cellic® CTec1 (CC1) and laccase was *Ganoderma lucidum* LacGL1 expressed in *Pichia pastoris* X-33. CC1 and LacGL1 were added in E/S ratio of 0.064%, and 0.4% (w/w), respectively.

Figure 12:
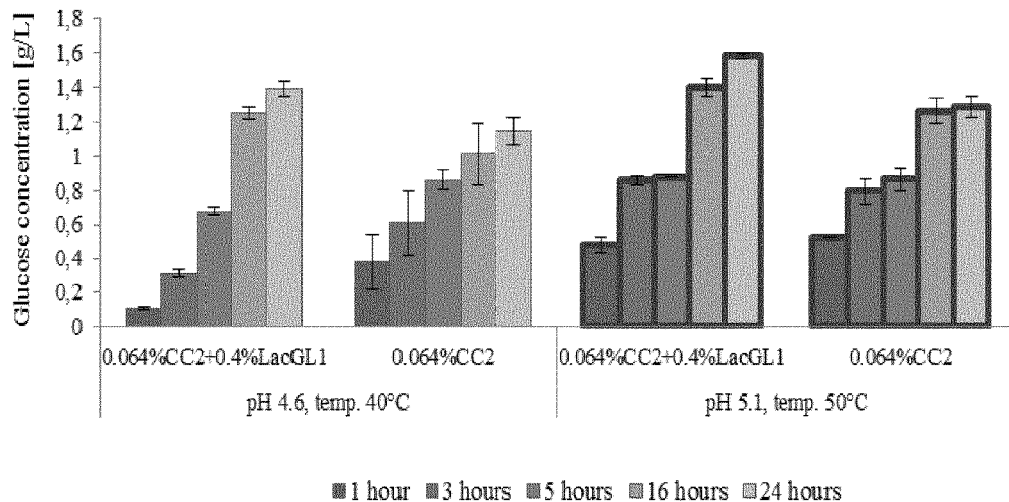

FIG. 12. A graphical comparison of the yields of released glucose over time in LacGL1-Cellic® CTec2 catalyzed hydrolysis of STEX-SCB at different pH and temperatures. The cellulase preparation is Cellic® CTec2 (CC2) and laccase was *Ganoderma lucidum* LacGL1 expressed in *Pichia pastoris* X-33. CC1 and LacGL1 were added in E/S ratio of 0.064%, and 0.4% (w/w), respectively.

Figure 13:
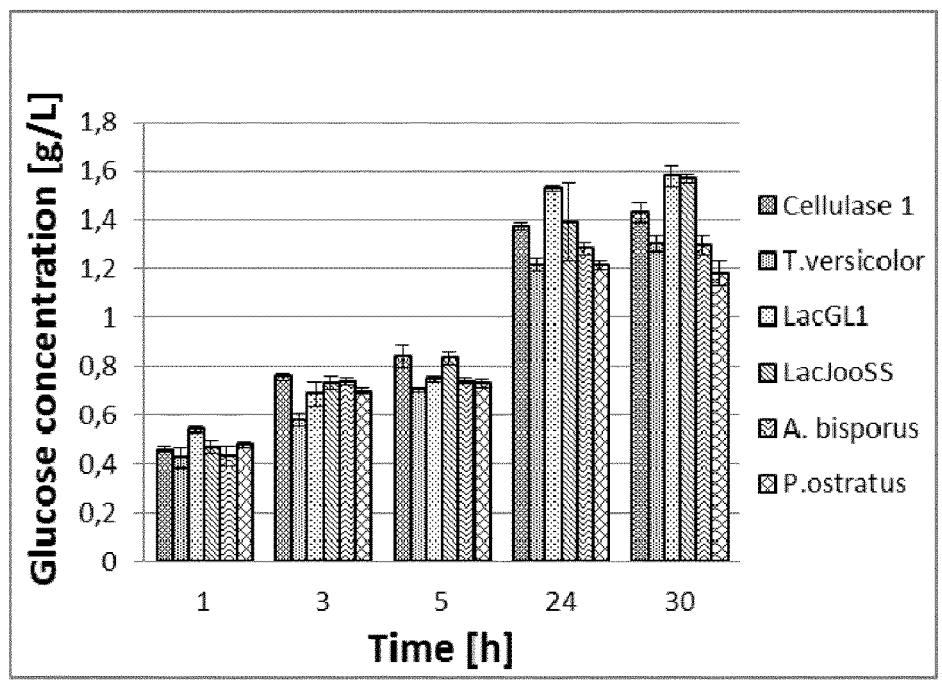
Figure 13:
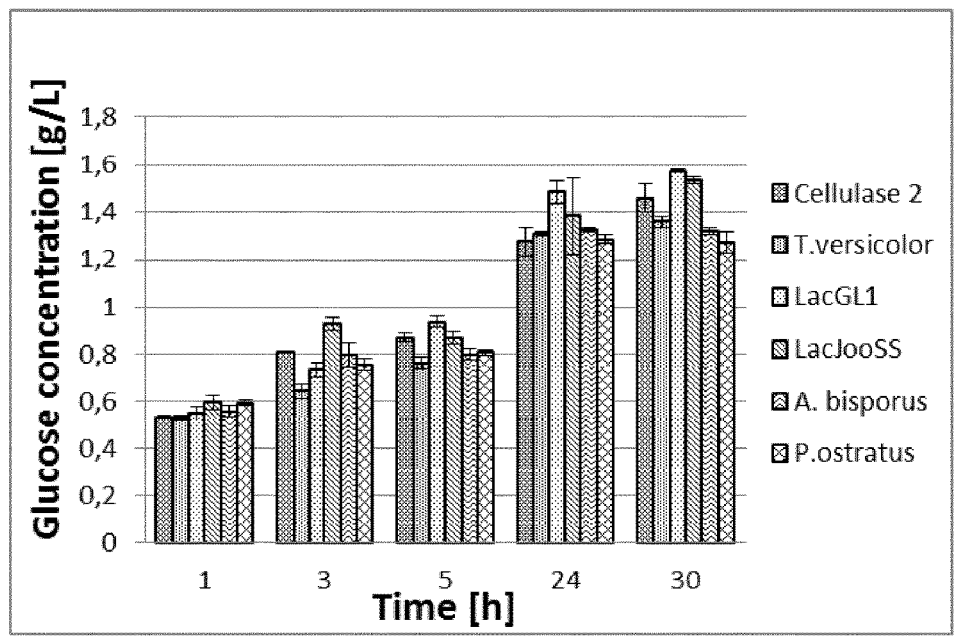

FIG. 13. A graphical comparison of glucose released over time during hydrolysis of STEX-SCB at pH 5.1 and 50° C. by each of commercial enzyme preparations Cellulase 1 (CC2) [A]; or Cellulase 2 [B], either alone, or in combination with a laccase enzyme; the tested laccases being respectively LacGL1 and GLlac1 (LacJooSS; Q9HG17) derived from *G. lucidum*; and laccases derived from *Agaricus bisporus* (Sigma 40452), *Pleurotus ostreatus* (Sigma 75117) and, *Trametes versicolor* (Sigma 51639).

Figure 14:
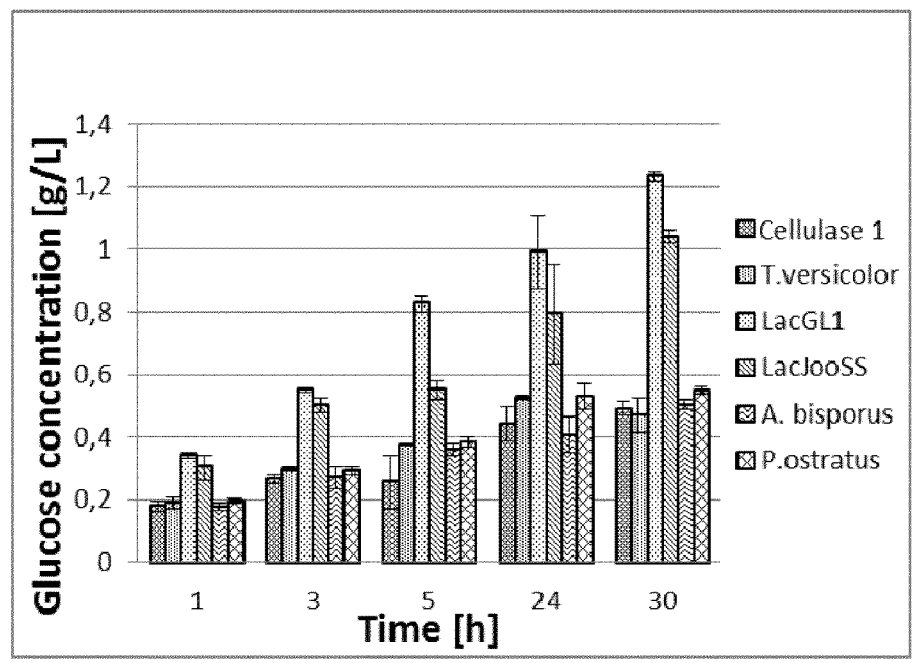
Figure 14:
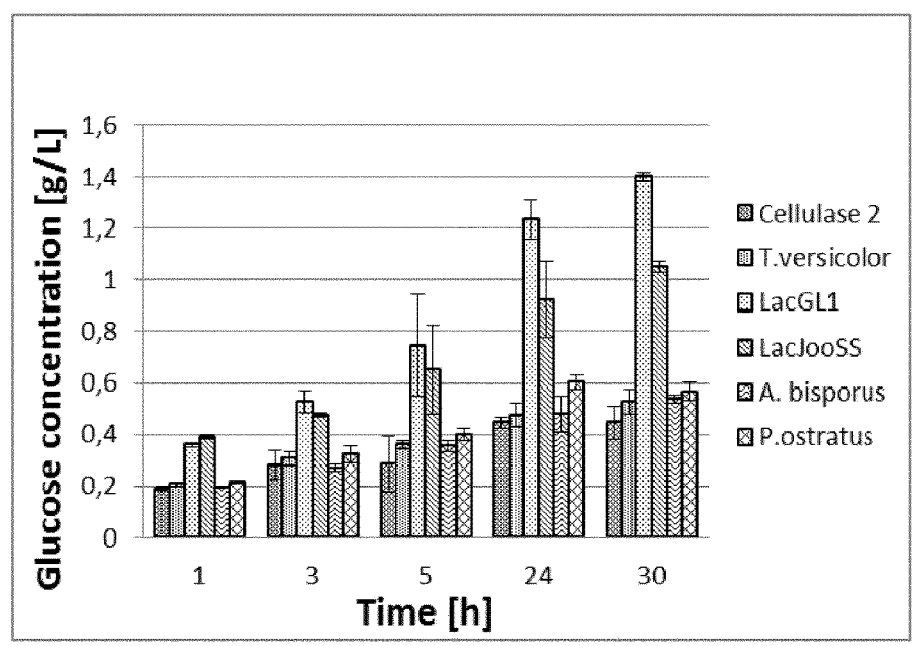

FIG. 14. A graphical comparison of glucose released over time during hydrolysis of pre-treated barley straw at pH 5.1 and 50° C. by each of commercial enzyme preparations Cellulase 1 (CC2) [A]; or Cellulase 2 [B], either alone, or in combination with a laccase enzyme; the tested laccases being respectively LacGL1 and GLlac1 (LacJooSS; Q9HG17) derived from *G. lucidum*; and laccases derived from *Agaricus bisporus* (Sigma 40452), *Pleurotus ostreatus* (Sigma 75117) and, *Trametes versicolor* (Sigma 51639).

Figure 15:
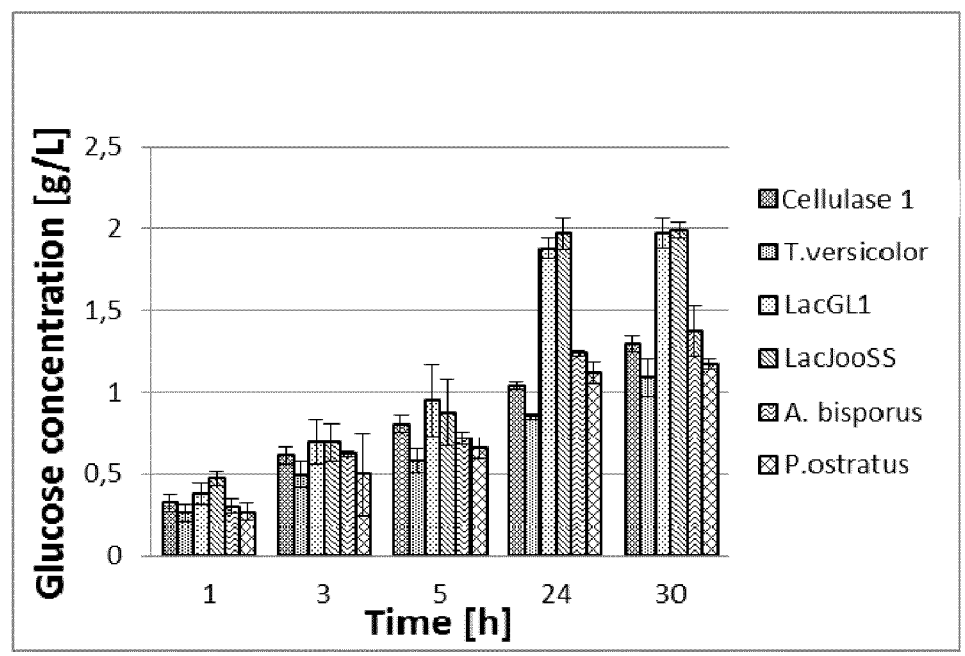
Figure 15:
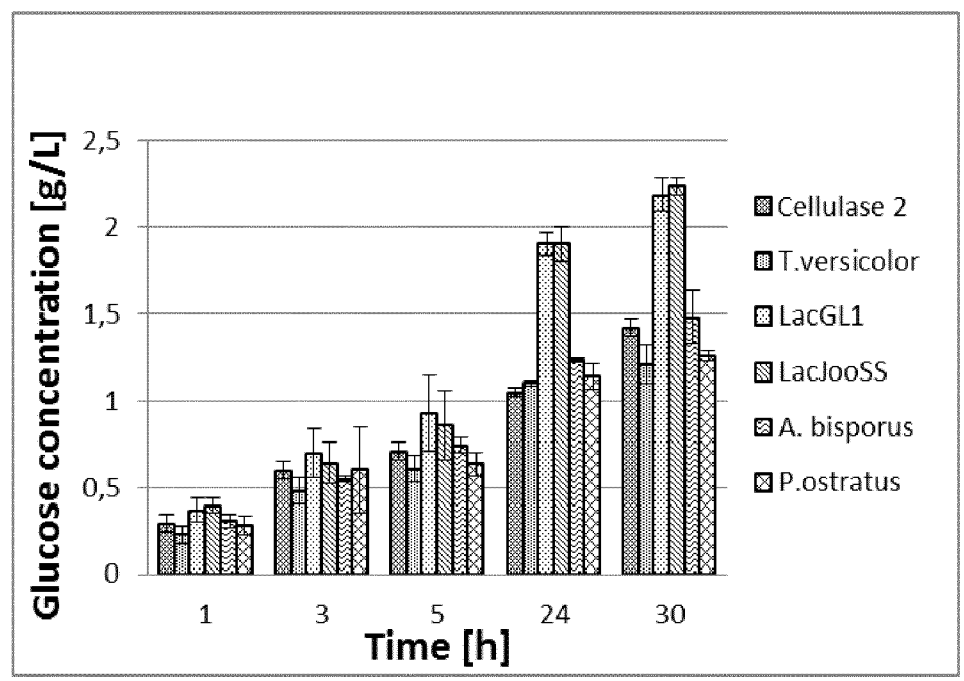

FIG. 15. A graphical comparison of glucose released over time during hydrolysis of pre-treated wheaty straw at pH 5.1 and 50° C. by each of commercial enzyme preparations Cellulase 1 (CC2) [A]; or Cellulase 2 [B], either alone, or in combination with a laccase enzyme; the tested laccases being respectively LacGL1 and GLlac1 (LacJooSS; Q9HG17) derived from *G. lucidum*; and laccases derived from *Agaricus bisporus* (Sigma 40452), *Pleurotus ostreatus* (Sigma 75117) and, *Trametes versicolor* (Sigma 51639).

DETAILED DESCRIPTION

I. A Fungal Laccase
I.i. Structural Properties of the Fungal Laccase

According to one embodiment, the invention provides a fungal laccase enzyme (EC 1.10.3.2), comprising a polypeptide having an amino acid sequence of 499 amino acids. The laccase polypeptide belongs to the multicopper oxidase family of enzymes, and comprises four copper binding domains that serve as coordinates for four copper atoms. The amino acid sequence of four regions (R1-R4) comprise copper binding domains that are highly conserved in this family of enzymes. In particular, the fungal laccase of the invention, shares a high degree of amino acid sequence identity with other fungal laccases in these four highly conserved regions, as shown in the alignment of their ungapped sequences in FIG. 5. The alignment indicates the position of 1 cysteine and ten histidines in these regions that coordinate to the T1Cu, T2Cu, T3αCu, and T3βCu copper ions, as well as the axial, non-coordinating isoleucine (455I) and phenylalanine (463F) conserved among the selected fungal laccases. Eight of the 10 histidines are part of a conserved pattern of HXH motifs, separated from each other by 25 to 175 amino acid residues, characteristic of copper binding domains (Kumar et al., 2003). The conserved amino acid sequences of these regions are reflected in corresponding secondary structures (α-helices and β-sheets) in each of these regions, which are shown above the aligned sequences in FIG. 5, that are based on a crystallographic structure of *Trametes versicolor* laccase (PDB ID: 1GYC).

Accordingly, the fungal laccase of the invention is a polypeptide comprising 499 amino acids, said polypeptide four peptide regions R1-R4 having amino acid sequence SEQ ID NO: 1, 2, 3, and 4 respectively, wherein the polypeptide is a laccase that is expressed by the fungus *Ganoderma lucidum*. In one embodiment, the fungal laccase is a polypeptide comprising 499 amino acids, whose amino acid sequence has at least 70, 75, 80, 85, 90, 92, 93, 94, 95, 96, 97, 98% or 99% sequence identity to SEQ ID NO: 5.

In a further embodiment the fungal laccase is expressed in vivo in a host cell as a polypeptide additionally comprising a signal peptide located at the N-terminus of the encoded polypeptide, whereby the signal peptide is cleaved off during expression and secretion of the polypeptide from the host cell. The signal peptide at the N-terminus of the expressed laccase is one that is suitable for expression system in the selected host cell, such as those listed below in respect to recombinant expression of the fungal laccase. In one embodiment, the fungal laccase comprising a signal peptide is a polypeptide comprising 520 amino acids, whose amino acid sequence shares at least 70, 75, 80, 85, 90, 92, 94, 95, 96, 97, 98% or 99% sequence identity to SEQ ID NO: 9. In another embodiment the fungal laccase is expressed with an N-terminal signal peptide comprising the α-mating factor pre pro peptide (MRIRHRSQD; SEQ ID NO: 7) from *Saccharomyces cerevisiae* (Brake, at al. 1983) as described in Example 5.1.

In a further embodiment, the fungal laccase is expressed in vivo in a host cell as a polypeptide additionally comprising a C-terminal or N-terminal peptide extension, whose amino acid sequence has a substrate binding affinity that enables its binding to the substrate thereby facilitating the isolation of a polypeptide comprising this peptide during purification (see recombinant expression of laccase below).

In a further embodiment, the fungal laccase, comprising 499 amino acids, whose amino acid sequence is at least 70, 75, 80, 85, 90, 92, 94, 95, 96, 97, 98% or 99% sequence identity to SEQ ID NO: 5, is characterized by a pI of 5.07, where the encoded polypeptide has a predicted molecular mass of 54.5 kDa. Since the amino acid sequence of the fungal laccase comprises several predicted glycosylation sites, the fungal laccase, when expressed in vivo in a eukaryotic host cell, will additionally be glycosylated. The degree and form of glycosylation will depend on the eukaryotic host cell in which the laccase is expressed, and may lead to an increase in the molecular mass of the fungal laccase, as described below in respect to recombinant expression of the laccase.

In a further embodiment, the fungal laccase of the invention comprises SEQ ID NO: 9, and is encoded by a DNA molecule having at least 80, 85, 90, 92, 94, 95, 96, 97, 98% or 99% nucleotide sequence identity to the laccase gene having SEQ ID NO: 6 or a cDNA derived from laccase m RNA having SEQ ID NO: 8, isolated from *Ganoderma lucidum* CBS229.93, as described below. The fungal laccase (LacGL1) from *Ganoderma lucidum* CBS229.93 having amino acid sequence of SEQ ID NO: 9 is distinct from all other published amino acid sequences, but is closely related to a laccase (UniProt Accession: Q9HG17) from *Ganoderma lucidum* strain 7071-9 (Joo, et al. 2008) (SEQ ID NO 29; where the mature protein corresponds to amino acid residues 22-520) and laccase (UniProt Accession:C5HL41), sharing 91% amino acid sequence identity with each of these reported sequences; while sharing 88% amino acid sequence identity with *G. lucidum* laccases with UniProt Accessions: B5G552 and B5G551. The fungal laccase (LacGL1) from *Ganoderma lucidum* CBS229.93 shares a much lower amino acid sequence identity with laccase isolated from *T. villosa*.

LacGL1 laccase (SEQ ID NO: 5) shows only 75% amino acid sequence identity to a laccase disclosed in CN1657611A that was isolated from *Ganoderma lucidum*.

I.ii. Functional Properties of the Fungal Laccase

The fungal laccase, comprising 499 amino acids, whose amino acid sequence is at least 70, 75, 80, 85, 90, 92, 94, 95, 96, 97, 98% or 99% sequence identity to SEQ ID NO: 5, is characterized by a pH optimum of 4.7 (Example 8.1), when measured with the substrate 2,2'-azinobis 3-ethylbenzothiazoline-6-sulfonic acid (ABTS) according to the method detailed in Example 7, or Table 2. The fungal laccase exhibits a substrate affinity, in respect of ABTS, of 0.107 mM when expressed in *Ganoderma lucidum* CBS229.93 (Example 1.5); and 0.122 mM when recombinantly expressed in *Pichia pastoris* (Example 8.2).

The predicted temperature optimum of the fungal laccase, at pH 4.7, is 55° C., while it retains high activities over the temperature range of 25-55° C. (Example 8.1). However, its thermal stability falls with time at temperatures above 50° C.

The fungal laccase can oxidise phenolic substrates (e.g. hydroxyquinone, and methoxy-substituted monophenols (e.g. guaiacol and 2,6-dimethoxyphenol) as shown in Table 5 in Example 8.2. The enzymatic activity of the fungal laccase is inhibited by sodium azide (90-100% inhibition at 0.01 mM); sodium fluoride (46-56% inhibition at 0.1 mM); EDTA (16-30% inhibition at 50 mM) and DTT (100% inhibition at 0.5 mM), as shown in Table 6 in Example 8.3.

The enzymatic properties reported in the literature for the closest related *Ganoderma lucidum* laccase, GlLCC1 (Q9HG17), when expressed in *P. pastoria*, were very different from those of LacGL1; with a pH optimum of 2.6, and a Km of 0.996 mM for ABTS (Sun et al., 2012). However, as shown herein, the two *Ganoderma lucidum* laccases LacGL1 and GLlac1 (Q9HG17) share an amino acid sequence identity of 91% and an unexpectedly similar capacity to enhance lignocellulose hydrolysis (see Example 12). The LacGL1 and GLlac1 laccases are clearly divergent from a *Ganoderma lucidum* laccase described by Wang and Ng, 2006, which had a higher molecular mass (75 kDa) a broader pH optimum (3-5), a higher temperature optimum (70° C.) and a different N-terminal amino acid sequence (GQNGDAVP).

II A LacGL1 Laccase Gene and cDNA from *Ganoderma lucidum* CBS229.93

According to a further embodiment, the invention provides an isolated LacGL1 gene and LacGL1 cDNA cloned from *Ganoderma lucidum* CBS229.93 that encodes the fungal laccase of the invention, LacGL1.

The LacGL1 gene was cloned from genomic DNA isolated from *Ganoderma lucidum* CBS229.93 employing PCR amplification. Specific amplification was assisted by the use of PCR primers whose sequence encoded amino acid sequences of isolated LacGL1 laccase peptides found to be conserved within the laccase enzyme family, as described in Example 2 and 4. The LacGL1 cDNA was cloned by PCR from cDNA synthesized from m RNA isolated from *Ganoderma lucidum* CBS229.93 as described in Example 4 (see 4.4).

The nucleotide sequence of the cloned LacGL1 gene is 2093 nucleotides in length, having SEQ ID NO: 6. The cloned sequence encompasses the entire coding sequence of the LacGL1 gene, extending from the start ATG codon to the TGA stop codon. The corresponding LacGL1 cDNA is 1563 nucleotides in length, having SEQ ID NO: 8. The LacGL1 gene comprises 9 introns, based on an alignment of the nucleotide sequences of the cloned LacGL1 gene and LacGL1 cDNA.

The LacGL1 cDNA from *Ganoderma lucidum* CBS229.93 has a nucleotide sequence that is distinct from all other published nucleotide sequences, but it shares 87% nucleotide sequence identity with the reported sequence of a laccase from *Ganoderma lucidum* strain 7071-9 (Joo, et al. 2008) and 77% with a Lac1 gene from *Polyporus brumalis* (Ryu, et al. 2008).

III Recombinant Expression of a Fungal Laccase

In a further embodiment, the invention provides recombinant genes, expression vectors and recombinant host cells that facilitate the expression of a fungal laccase, as defined above in section I, wherein the laccase is a polypeptide that at least comprises 499 amino acids, whose amino acid sequence has at least 70, 75, 80, 85, 90, 92, 94, 95, 96, 97, 98% or 99% sequence identity to SEQ ID NO: 5.

III.i. DNA Molecule Encoding a Recombinant Fungal Laccase

A DNA molecule encoding the fungal laccase can be synthesized in vitro, whose nucleotide sequence is designed to provide a codon usage that is optimal for expression in a given host cell, such methods being described in standard textbooks in the art. In one embodiment the DNA molecule encodes a fungal laccase polypeptide that additionally has a signal peptide at the N-terminus to facilitate secretion of the laccase by a host cell, and where the signal peptide has a cleavage site that defines the position of signal peptide removal during expression. When the DNA molecule encoding the fungal laccase polypeptide is expressed in a host cell that is a yeast cell, a suitable signal peptide for facilitating secretion includes the α-mating factor pre pro peptide from *Saccharomyces cerevisiae* (Brake, at al. 1983) as described in Example 5.1. Alternative signal peptides, suitable for expression and secretion in eukaryotic hosts are known in the art.

In a further embodiment, the DNA molecule encodes a fungal laccase polypeptide that additionally has a C-terminal or N-terminal peptide (peptide tag), whose amino acid sequence has a substrate binding affinity, facilitating purification of the polypeptide. In one embodiment the DNA molecule encodes a fungal laccase polypeptide that additionally has a C-terminal peptide comprising a c-myc epitope, as exemplified in Example 5.

III.ii A DNA Vector for Cloning and/or Expression of a Recombinant Fungal Laccase In a further embodiment, the invention provides a DNA molecule, wherein the molecule is a DNA vector (plasmid) comprising a nucleic acid sequence encoding the fungal laccase polypeptide. The DNA vector is either a vector capable of self-replication within the host cell, or it is an integration vector, capable of integration into the genome of the host cell. The DNA molecule (and vector) may comprise a DNA promoter capable of directing the in vivo expression of the encoded fungal laccase. The nucleic acid sequence encoding the fungal laccase may be cloned downstream of the DNA promoter located in the DNA molecule (or vector) and subsequently transformed into a host cell, where it is either capable of self-replication or all or part of the DNA molecule is integrated into the host genome. If the DNA molecule is integrated into the host genome, it can be inserted down-stream of a promoter present in the host genome, the promoter in both cases being capable of directing expression of the DNA molecule in the respective host cell in vivo. DNA promoter sequences suitable for directing expression of the DNA molecule encoding a fungal laccase including inducible promoter systems are known in the art, as further exemplified in Example 5.

III.iii A Host Cell Expressing of a Recombinant Fungal Laccase

A recombinant host cell comprising a recombinant DNA molecule (transgene) encoding the fungal laccase describe above is a prokaryotic or eukaryotic cell, capable of both expressing and secreting the fungal laccase. The host cell may comprise a vector (plasmid) comprising the DNA molecule and capable of self-replication in the host, or alternatively, the host cell may comprise the DNA molecule as a transgene, stably integrated into the host genome. Examples of a suitable host prokaryotic cell for recombinant expression include *Bacillus subtilis* and *Escherichia coli*. Examples of a host eukaryotic cell, suitable for expression of the recombinant DNA molecule (transgene) and secretion of the fungal laccase include *Aspergillus niger, Aspergillus tubigensis, Aspergillus awamori, Trichoderma reesei, Penicillium funiculosum, Bacillus subtilis, Bacillus licheniformis, Hansenula polymorpha*. Expression of the fungal laccase in a yeast cell is exemplified in Example 5, where the fungal laccase is expressed as a polypeptide comprising an N-terminal signal peptide comprising the α-mating factor pre pro peptide from *Saccharomyces cerevisiae* (Brake, at al. 1983), and a C-terminal comprising 6 consecutive histidine residues and a c-myc epitope having as described in Example 5.1. The signal peptide is co-translationally cleaved off the polypeptide, and the mature polypeptide having SEQ ID NO: 10 is secreted into the extracellular medium of the yeast cell.

III.iv Production, Concentration and/or Purification of a Recombinantly Expressed Fungal Laccase A host cell comprising a recombinant DNA molecule (transgene) encoding the fungal laccase can be cultivated or incubated in a medium that allows for the expression of the DNA molecule (transgene) encoding the fungal laccase. Media suitable for cultivation and/or incubation of a host cell, will be host dependent, and known in the art. When the fungal laccase is recombinantly expressed and secreted by a host cell, the fungal laccase will be released into the extracellular medium. Use of an inducible promoter, as describe above (III.ii), can be used to selectively induce expression of the recombinant gene encoding the fungal laccase, such that the secreted fungal laccase accounts for a majority of the protein in the extracellular fraction. Further concentration and/or purification of the fungal laccase will depend on the degree of purity required for the fungal laccase.

In one embodiment the fungal laccase includes a peptide tag (as described in III.i) whose substrate binding properties facilitate selective binding of the secreted fungal laccase to a solid substrate. For example, a fungal laccase having a c-Myc peptide will bind to an anti-C-myc antibody column by virtue of the epitope (AEEQKLISEEDL), and the fungal laccase can subsequently be specifically released from the column.

IV Formulation of a Recombinantly Expressed Fungal Laccase

A recombinantly expressed fungal laccase of the invention having at least 70, 75, 80, 85, 90, 92, 94, 95, 96, 97, 98% or 99% sequence identity to SEQ ID NO: 5, which may optionally have been processed by concentration and/or purification, can optionally be dried (for example by freeze-drying) for subsequent formulation and/or packaging in dried (granulated or spray dried form). In one embodiment the fungal laccase is formulated and/or packaged in dried or liquid form as a fungal laccase concentrate. In another embodiment, fungal laccase is formulated and/or packaged in dried or preferably liquid form as a mixture combined with additionally one or more enzymes. The additional one or more enzymes may for example be cellulose-degrading enzymes (e.g. Cellic® CTec1 and Cellic® CTec2 supplied by Novozymes A/S; and Laminex C2K, Multifect B, GC 220 and GC 880 supplied by Dupont/Danisco/Genencor International B.V.).

V. Use of a Fungal Laccase in Biomass Hydrolysis

Surprisingly, the fungal laccase of the invention, for example when expressed in its native host, *Ganoderma lucidum* CBS229.93, is able to support cell growth in growth media where lignin (in the form of alkaline lignin) is the primary carbon source, as well as growth media in which the primary carbon source is Sugarcane Bagasse (SCB). *Ganoderma lucidum* CBS229.93 outperformed a number of other tested white rot fungi, in its ability to grow on both lignin and the lignocellulose substrate, SCB, as shown in Example 1. The surprisingly strong growth of *Ganoderma lucidum* CBS229.93, on these lignin-based substrates, is due to a high level of laccase secretion, which catalyzes the depolymerization of the lignin and lignocellulose substrates.

The fungal laccase of the invention, obtainable as a recombinantly expressed enzyme in a host cell, or from expression by a native host, for example *Ganoderma lucidum* CBS229.93, has been isolated, and shown to oxidise both phenolic compounds, methoxy-substituted compounds and ABTS as shown in Example 2 and 8. The most important and unexpected property of the fungal laccase of the invention, is its ability to synergistically enhance the depolymerisation (hydrolysis) of lignocellulose substrates by cellulases. The depolymerized biomass product STEX-SCB (which is SCB pre-treated by a steam-explosion process), barley straw and wheat straw into glucose are all markedly increased by a combination of the fungal laccase together with cellulose enzyme mixtures, as those available in commercial form, for example Cellic® CTec1 and Cellic® CTec2, as illustrated in Example 3, 10 and 12. This unexpected and valuable property was not seen for any other commercially available laccase tested. This synergistic effect allows a decrease in the total enzyme dosage of cellulase (e.g. Cellic® CTec2) needed for de-polymerization of the pretreated biomass, which has a potential in decreasing of the overall operational costs of cellulose-to-glucose conversion and a simultaneous increase in the yields of the produced ethanol. The activity of the fungal laccase is highest at pH 4.7 and between 40-50° C., which is very close to the conditions optimal for Cellic® CTec1 and Cellic® CTec2, which is an additional factor contributing to the synergy between these enzymes. Use of the fungal laccase whose activity optimum is exhibited under conditions that closely mirror those needed for cellulose degradation also simplifies and speeds the processing of biomass.

The use of the fungal laccase in combination with cellulose hydrolyzing enzymes can boost the tolerance of this de-polymerization process to inhibitory compounds produced during different forms of pretreatment, and thereby reduce the need to wash the biomass free of inhibitors. The fungal laccase also allows for a faster reaction turnover in the hydrolysis tank, which has a direct impact on amount of storage space required for lignocellulosic material and reduces the time window for spoilage during storage.

Thus, according to a further embodiment, the fungal laccase of the invention is for use in a process for lignocellulose biomass depolymerization, where the fungal laccase is a polypeptide that at least comprises 499 amino acids, whose amino acid sequence has at least 70, 75, 80, 85, 90, 92, 94, 95, 96, 97, 98% or 99% sequence identity to SEQ ID NO: 5. The fungal laccase can be used in a process of lignocellulose biomass depolymerization where it is added in combination with one or more cellulose-hydrolyzing enzymes. Cellulose hydrolysis involves the synergistic action of three types of cellulases including endo-β-1,4-glucanase (EC 3.2.1.4), exoglucanase (EC 3.2.1.91) and β-glucosidase (EC 3.2.1.21), which, step by step, nick the intermolecular β-1,4-glucosidic bonds, cleave cellulose chain ends to release cellobiose unit, and cut cellobioses and oligosaccharides to produce glucose. Examples of enzyme compositions comprising cellulose-hydrolyzing enzymes include Cellic® CTec1 and Cellic® CTec2 supplied by Novozymes A/S; and Laminex C2K, Multifect B, GC 220 and GC 880 supplied by Dupont/Danisco/Genencor International B.V.). Alternatively the fungal laccase can be used in a two-step process, where the lignocellulose biomass is incubated with the fungal laccase in a first step, and then one or more cellulose hydrolyzing enzymes are subsequently added prior to a second incubation step. A two-process allows the two steps to be carried out under conditions further optimized for the respective enzyme preparations. The biomass to be hydrolyzed is composed of lignocellulose, and is preferably SCB, barley straw or wheat straw. More preferably the biomass is pretreated with heat and/or steam, as described in Example 9 and 12.

VI A Method for Biomass Depolymerization Using a Fungal Laccase

In a further embodiment, the invention provides a method for lignocellulose biomass hydrolysis (depolymerization), where the biomass includes SCB, barley straw and wheat straw, more preferably pre-treated lignocellulose biomass. The method employs the fungal laccase of the invention, which is shown to enhance cellulase-mediated hydrolysis of lignocellulose biomass to a significantly greater degree compared to several other commercially available laccases.

The method includes the steps of:
a. providing an aqueous dispersion of lignocellulose biomass;
b. adding a preparation of fungal laccase to the biomass (a), wherein the fungal laccase is as defined in section I (optionally a recombinantly expressed fungal laccase as defined in section III);
c. adding a preparation of cellulose degrading enzymes to the biomass in (b), wherein the addition in step b) is either simultaneous with the addition in step c), or is prior to the addition in step c);
d. incubation of the biomass of step b) and step c), either simultaneously or in sequence; and optionally
e. separation of soluble from insoluble biomass to obtain a soluble aqueous hydrolysate.

The term "in sequence" in respect to "incubation" in step (d) is to be understood to comprise a first incubation period of the product of step (b) followed by a second incubation period of the product of step (c). Suitable cellulose degrading enzymes in this method include Cellic®CTec1 and Cellic®CTec2 supplied by Novozymes A/S; and Laminex C2K, Multifect B, GC 220 and GC 880 supplied by Dupont/Danisco/Genencor International B.V.

VI a Method for Detecting and Measuring Laccase Activity of a Fungal Laccase

Methods for the accurate measurement of laccase activity of a fungal laccase of the invention and for determining its substrate specificity and conditions optimal for its enzymatic activity (EC 1.10.3.2) are detailed in example 7.

EXAMPLES OF THE INVENTION

Example 1

*Ganoderma lucidum* CBS229.93 Expresses High Laccase Activity

Forty four white-rot fungal isolates belonging to *Ascomycota* (strains of *Alternaria*, *Fusarium*, *Memnoniella*, *Stemphyliu*, and *Ulocladium*), and *Basidiomycota* were screened for their ability to grow on sugarcane bagasse, where only four basidiomycete isolates (*Ganoderma lucidum*, *Trametes versicolor*, *Polyporus brumalis*, and *Polyporus ciliatus*) were able to grow on this recalcitrant substrate—chosen as an important source of ligninolytic substrate. A special focus was paid to *Ganoderma lucidum*, which was the only fungal isolate that could additionally grow on lignin (lignin alkaline) supplemented to the cultivation medium Four different white-rot fungi (*Ganoderma lucidum*, *Polyporus brumalis*, *Polyporus ciliatus* and *Trametes versicolor*) were then compared as a source of laccase activity. The fungi were grown on nitrogen-rich (MEA) or nitrogen-limited (MM) medium supplemented with various carbon and lignin-derived sources, and the culture medium was subsequently collected, and tested for secreted laccase activity, as described below.

1.1 Source of White-rot Fungi (*Basidiomycetes*)

*Ganoderma lucidum* (CBS 229.93), *Trametes versicolor* (CBS 100.29), *Polyporus brumalis* (CBS 470.72), *Polyporus ciliatus* (CBS 366.74), were purchased from CBS Fungal Biodiversity Center (www.cbs.knaw.nl.). *Ganoderma lucidum* was maintained on Malt Extract Agar (MEA) slants (2% malt extract, 0.1% peptone, 2% glucose, and 1.5% agar). The medium was adjusted to a pH of 6.0 with 2 M NaOH, prior to sterilization (121° C., 20 min.).

1.2 Growth Media and Cultivation of White-rot Fungi for Testing Laccase Production Malt Extract medium (MEA), contained: malt extract 20 g/L; peptone 1 g/L; glucose 20 g/L, and agar 20 g/L for agar slants. MEA medium was supplemented with 1 mL of a stock trace metal solution (1 g/L $ZnSO_4*7H_2O$ and 0.5 g/L $CuSO_4*5H_2O$).

Minimal Medium (MM), was prepared as described before (Songulashvilli, et al. 2008), and contained $NH_4NO_3$ 1 g/L; $Na_2HPO_4$ 0.2 g/L; $KH_2PO_4$ 0.8 g/L; $MgSO_4*7H_2O$ 0.5 g/L.

MEA and MM medium were supplemented with a combination of 5 g/L SCB and 5 g/L Avicel (Sigma Aldrich, Germany), 5 g/L Lignin Alkaline (NacalaiTesque Inc. Kyoto, Japan), 10 g/L Sugar cane Bagasse (SCB) or 10 g/L LA (referred in text as SCB+AV, LA, and SCB, respectively). Additionally, MM medium was supplemented with 2 g/L of glucose when 10 g/L LA or 10 g/L SCB were added.

The pH of both media was adjusted to 5.6 with 2 M NaOH prior to autoclaving. All fungal cultures were cultivated at 25° C. for a period of 16 and 30 days for MEA and MM medium, respectively. The growth of fungi was performed on solid support, such as leca beads (JohannesFog S/A, Denmark), which was added and autoclaved together with the medium.

Fungal crude extract (15 mL), corresponding to the media remaining after removal of mycelia and leca beads by centrifugation at 10.000 rpm for 20 min, was frozen and freeze-dried (Lyovac GT 2, Germany) to a dry pellet. The dry pellet was 10 times concentrated by solubilization in 1.5 mL of water and used to assay laccase activity (by ABTS plate assays, SDS-PAGE and Native-PAGE analysis).

1.3 ABTS Plate Assay for Laccase Activity

Laccase activity was detected using the substrate 2,2'-azinobis(3-ethylbenzothiazoline-6-sulfonic acid (ABTS; purchased from Sigma Aldrich, Germany) as described by Srinivasan et al. 1995. 25 µL of 10× concentrated crude fungal aqueous extract solution were placed in a 4 mm well in the ABTS-agar plate. Appearance of a green halo around the well indicates laccase activity. 25 µL of boiled crude extract solution was used as a negative control, while 25 µL of commercial preparation of laccase (Cat. no. 51639), lignin peroxidase (Cat. no. 42603) and manganese peroxidase (Cat. no. 93014) were used as enzyme activity controls. All enzymes were purchased from Sigma-Aldrich, Germany and were diluted to the same concentration of U/mL, prior to ABTS-plate assay.

Laccases catalyse the oxidation of ABTS in absence of $H_2O_2$, while lignin peroxidase and manganese peroxidase require at least 0.003% (w/v) $H_2O_2$. In order to exclude oxidases, potentially present in crude extract, as the cause of ABTS by oxidization in the presence of hydrogen peroxide, hydrogen peroxide was added to all commercial enzyme preparations in the final concentration of 0.003% (w/v). The false-positive response of ABTS to hydrogen peroxide (fungi are able to produce $H_2O_2$-producing enzymes (Lonergan, Baker, 1995)) present in the crude extract was monitored at hydrogen peroxide concentrations of 30, 0.3, 0.03 and 0.003% (w/v). These tests established that $H_2O_2$ levels as high as 30% (w/v) were required for auto-oxidization of ABTS, ruling out the likelihood of fungal false positives.

1.4 High Laccase Activity Detected in *Ganoderma lucidum* CBS229.93 Grown on Lignin-supplemented Media Compared to the other white rot fungi tested, *Ganoderma lucidum* CBS229.93 was better able to metabolize and grow on lignin-supplemented media, due to its stronger grow on all media tested, including Lignin Alkaline (LA) supplemented media (Table 1). Furthermore, *Ganoderma lucidum* CBS229.93 secreted correspondingly higher laccase activity levels, based on the degree and speed of green color development the ABTS plate assay. In comparison, *Polyporus brumalis* and *Polyporus ciliatus* were unable to grow and secrete detectable ABTS oxidation activity when grown on MEA medium supplemented with LA, although they were able to grow to a lesser degree on all other media tested. The growth of *Trametes versicolor* was similar to that of *G. lucidum*; however the detected oxidation of ABTS was much lower.

TABLE 1

Evaluation of the fungal growth[1] on the recalcitrant substrate supplementing both MM and MEA medium

| Cultivation media used[2] | | Ganoderma lucidum | Polyporus brumalis | Polyporus ciliatus | Trametes versicolor |
|---|---|---|---|---|---|
| LA [3] | MM | + | ± | ± | ± |
| | MEA | ++ | − | − | − |
| SCB + Av. [4] | MM | ++ | + | + | + |
| | MEA | +++ | + | + | + |
| SCB [5] | MM | ++ | + | + | + |
| | MEA | +++ | + | + | + |

[1]The grading of the fungal growth on recalcitrant substrate supplementing MM and MEA medium on a (+), (−) scale. (±) faint growth (single mycelium colonies), (+) good growth (mycelium mat covering the whole diameter of the experimental tube), (++) better growth (as in case of good growth but mycelium mat thicker), (+++) exceptional growth (thick mycelium mat plus spreading fungal growth on the walls of the experimental tube), and (−) no growth. The grading of the fungal growth was based on the area of mycelium (colony size) floating on the Leca ® beads support added to the cultivation medium.
[2]Cultivation media used in this study; MEA (malt extract medium) and MM (minimal medium)
[3, 4, and 5] Cultivation media supplementation: Lignin Alkaline (LA), sugarcane bagasse and Avicel (SCB + AV.), and sugarcane bagasse (SCB), respectively.

1.5 Laccase Activity Produced by *Ganoderma lucidum* is Quantitatively Greater than Other White-rot Fungi Laccase activity in the crude extracts of all four fungi, was measured quantitatively using syringaldazine (Sigma Aldrich, Germany), which is a true laccase substrate, due to its lack of auto-oxidation by the interference from peroxidases (Harkin, et al. 1974). Laccase activity was measured by the method of Ryde (1980).

Quantitative measurements for the four fungi grown on media supplemented with SCB and SCB+AV, show that the highest laccase activity were obtained with *Ganoderma lucidum* when grown on MEA medium, which were 3.5 fold higher compared to cultivation in MM medium under the same conditions (FIG. 1). By comparison, the laccase activity yields for *Polyporus brumalis* and *Polyporus ciliatus* were 13 to 17 fold lower than for *Ganoderma lucidum*. Similarly, an approximately six fold higher laccase activity yield was detected for *Ganoderma lucidum* grown on MEA supplemented with LA, as compared to *P. ciliatus, P. brumalis*, and *T. versicolor* (FIG. 1).

Example 2

Characterization of Laccase Expressed and Secreted by *Ganoderma lucidum* CBS229.93

Native laccase secreted by *Ganoderma lucidum* CBS229.93 was chacterised in repect of its molecular mass, kinetic properties, and partial sequence.

2.1 SDS-PAGE Electrophoresis of *Ganoderma lucidum* CBS229.93 Secreted Proteins.

Crude protein extracts obtained from *Ganoderma lucidum*, grown on MEA medium supplemented with SCA, SCA+AV or LA, each contained an approximately 62.5 kD protein, which is slightly lower than the molecular mass of the commercial laccase from *Trametes versicolor* (FIG. 2).

2.2 Native PAGE Electrophoresis of *Ganoderma lucidum* CBS229.93 Secreted Proteins Native PAGE of the crude protein extract of *Ganoderma lucidum* was performed according to Hoopes and Dean (2001), where laccase activity was detected by incubating the gel with the laccase substrate 1.8-diaminonaphthalene (DAN). The 62.5 KD protein secreted by *Ganoderma lucidum* was thereby identified as an active laccase.

2.3 Kinetic Measurements of Secreted *Ganoderma lucidum* CBS229.93 Laccase

The *Ganoderma lucidum* CBS229.93 laccase was calculated to have a $K_m$ value of 0.107 mM for the substrate ABTS based on a Hanes-Wolf plot, Table 2, which lies in the median range with respect to other fungal laccases, while being distinct from and lower than the $K_m$ value of the *Ganoderma lucidum* laccase, GaLc3.

TABLE 2

Kinetic constants of laccases*. The pH value at which $K_m$ was measured is also included.

| Substrate | Laccase | $K_m$ (μM) | pH | Reference |
|---|---|---|---|---|
| ABTS | *Pleurotus sajor-caju* Lac4 | 2500 | 3.3 | Soden, et al. 2002 |
| | *Myceliophthora thermophila* Lcc1 | 290 | 6 | Bulter, et al. 2003 |
| | *Pleurotus ostreatus* POXC | 280 | 3 | Palmieri, et al. 1997 |
| | *Pleurotus ostreatus* POXA2 | 120 | 3 | Palmieri, et al. 1997 |
| | *Ganoderma lucidum* CBS229.93 | 107 | 5 | |
| | *Pleurotus ostreatus* POXA1 | 90 | 3 | Palmieri, et al. 1997 |
| | *Rhizoctonia solani* Lcc4 | 52 | 5.3 | Xu, et al. 1995 |
| | *Ganoderma lucidum* GaLc3 | 370 | 5 | Ko, et al. 2001 |
| | *Trametes trogii* POXL3 | 30 | 3.4 | Garzillo, et al. 1998 |

*Michaelis constant ($K_m$) of laccase secreted *Ganoderma lucidum* was measured under reaction conditions detailed by Bourbonnais and Pace (1992), using the substrate ABTS (aqueous solution ABTS of 50 mg/mL) as described by Wolfenden and Willson, 1982, at a final concentration of: 0.0113, 0.0085, 0.006, 0.0025, 0.001, 0.0005, and 0.0001M.

2.4 Partial Amino Acid Sequence of Secreted *Ganoderma lucidum* CBS229.93 Laccase The partial amino acid sequences of peptides derived from *Ganoderma lucidum* CBS229.93 laccase showed homology to laccase sequences from *Basidiomycota* (Table 3). In particular, the amino acid sequences between position 88 to 100, and position 185 to 197 are quite conserved within the family of Ganodermataceae's based on blast results in UniProt database (Apweiler, et al. 2004).

TABLE 3

Overview of identity of four glycopeptides analyzed by MALDI-TOF from *G. lucidum* CBS229.93 * to other laccases deposited in NCBI database

| | | | sequence identity of discovered glycopeptides [%] | | | |
|---|---|---|---|---|---|---|
| UniProt identifier | Identified organism | AA seq. | [88]TTSIHWH GFFQK[100] | [245]DDDSTVL TLADWYHV AAR[263] | [452]TLSNADI APDGFTR[466] | [185]GSDSTLI NGLGR[197] |
| Q9GH17 | *Ganoderma lucidum* 7071-9 | 520 | 100 | 80 | 81 | 100 |
| Q9HDS8 | *Polyporus cilliatus* | 524 | 90 | 80 | 81 | 100 |
| C5HL41 | *Ganoderma lucidum* TR6 | 520 | 100 | 80 | 81 | 100 |
| B5G552 | *Ganoderma lucidum* RZ | 520 | 100 | 75 | 88 | 100 |
| Q308Q9 | *Trametes versicolor* | 522 | 100 | 85 | 64 | 93 |
| A3F8Z8 | *Polyporus brumalis* lac1 | 520 | 100 | 90 | 70 | 93 |
| A3F8Z8 | *Polyporus brumalis* lac2 | 524 | 90 | — | — | 93 |
| Q9UVQ2 | *Pycnoporus cinnabarinus* lac1 | 518 | 90 | 75 | 68 | 93 |

* *Ganoderma lucidum* laccase protein (~62.5 kDa) was excised from SDS-PAGE gel and in-gel digested with trypsin prior to MALDI-TOF analysis as previously described by Thaysen-Andersen (2009) and as detailed by Schiøt (2010). The short amino acid peptide sequences were obtained by the de novo sequencing and were analyzed using 4800 Proteomics Analyzer (Applied Biosystems, Foster City, CA, USA) in MS/MS mode, followed by manual interpretation of the obtained MS/MS spectra by the AminoCalc program (Protana A/S, Odense, Denmark). Peptide 88-100 (SEQ ID NO: 11); Peptide 245-263 (SEQ ID NO: 12); Peptide 452-466 (SEQ ID NO: 13); Peptide 185-197 (SEQ ID NO: 14);

Example 3

*Ganderma lucidum* CBS229.93 Laccase Enhances Cellulase-mediated Hydrolysis of Steam Exploded SCB and Glucose Release by Cellic®CTec1

FIG. 4 A shows a graphical comparison of glucose released over time during hydrolysis of steam-exploded SCB at pH 5.1 and 50° C. by the enzyme preparation Cellic®CTec1 (CC1) alone, and in combination with crude protein extract from *Ganoderma lucidum* grown on MEA (SCB) as compared to commerically available *Tramates versicolor* laccase. CC1 and crude protein extract from *Ganoderma lucidum* were added in enzyme/substrate (E/S) ratio of 0.064%, and 0.2% (w/w), respectively. Addition of the *Ganoderma lucidum* crude protein extract increased glucose release by 17% over a period of 24 h in when tested on a 5% (w/v) dry matter of pretreated SCB (STEX-SCB). When this comparative assay was performed again (see FIG. 4B), but at pH 4.8 with a substrate of 0.8% (w/v) dry matter pretreated SCB, the addition of the *Ganoderma lucidum* crude protein extract increased glucose yields by 43% over a period of 24 h. In contrast, *Tramates versicolor* laccase actually reduced cellulase-mediated STEX-SCB hydrolysis.

Example 4

Cloning and Characterisation of *Ganderma Lucidum* CBS229.93 Laccase Gene, LacGL1 and cDNA Encoding Laccase The LacGL1 gene encoding the LacGL1 laccase was cloned by PCR amplification from genomic DNA isolated from *Ganoderma lucidum* CBS229.93.

4.1 Isolation of Genomic DNA Isolated from *Ganderma Lucidum* CBS229.93

*Ganoderma lucidum*'s mycelium (0.1 to 0.3 g) was collected from MEA plates using a sterile scalpel, transferred to a previously cooled mortar and pestle, and ground in liquid nitrogen. The genomic DNA was isolated using the chloroform: phenol: isoamyl alcohol (25:24:1, v:v:v) method previously described by Lee and Taylor (1990). Extracted DNA pellets, from 10 isolation tubes, resuspended in 10 μL of TE buffer each (10 mM Tris-HCl, 100 mM EDTA, pH 7.2) were collected and precipitated together using 2 to 3 volumes of ice-cold 96% ethanol (v/v) and ⅒ volume of 3 M sodium acetate, pH 5.2. and incubated at −20° C. overnight. The genomic DNA was then pelleted by centrifugation at 14000 rpm at 4° C. for 30 min., and the pellet was washed in 70% ethanol (v/v), dried at room temperature and resuspended in a desired amount of TE buffer.

4.2 Cloning the LacGL1 Gene from Ganderma lucidum CBS229.93 Genomic DNA

MALDI-TOF analysis of Ganoderma lucidum CBS229.93 laccase revealed amino acid sequence identity between five short peptides belonging to Ganoderma luci- dum CBS229.93 laccase and G. lucidum Q9HG17 laccase, where the two peptides TTSIHWHGFFQ and FPLGSD- STLINGLG, were highly conserved within several members of Basidiomycota (Table 3). A forward and reverse PCR primer pair (WADGP_fwd3 and LINGLP_rev1 in Table 4) were designed based on the corresponding G. lucidum Q9HG17 m RNA sequence encoding these two conserved peptide sequences.

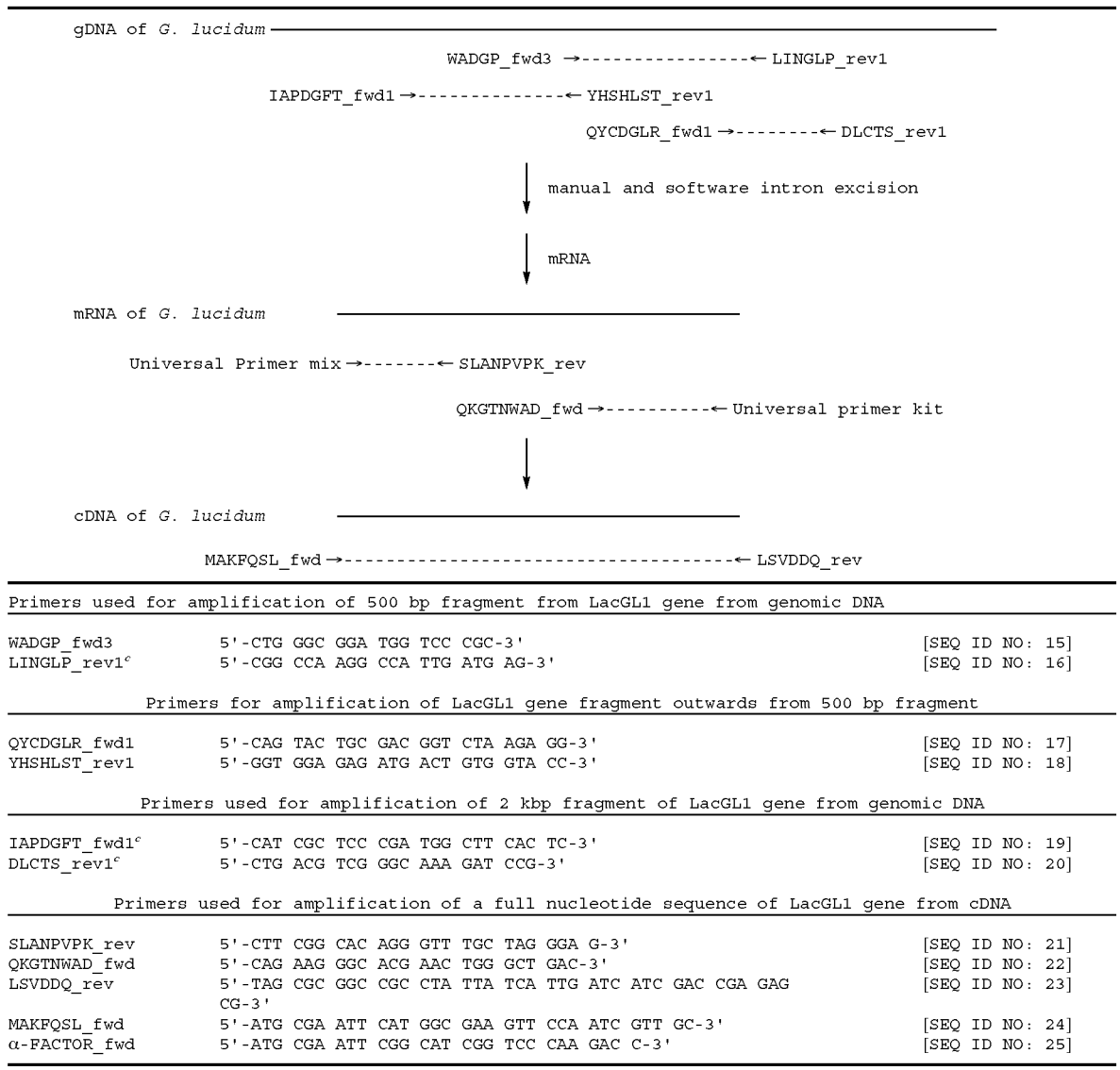

TABLE 4

Cloning steps for isolation of the LacGL1 gene

| Primers used for amplification of 500 bp fragment from LacGL1 gene from genomic DNA | | |
|---|---|---|
| WADGP_fwd3 | 5'-CTG GGC GGA TGG TCC CGC-3' | [SEQ ID NO: 15] |
| LINGLP_rev1<sup>c</sup> | 5'-CGG CCA AGG CCA TTG ATG AG-3' | [SEQ ID NO: 16] |

| Primers for amplification of LacGL1 gene fragment outwards from 500 bp fragment | | |
|---|---|---|
| QYCDGLR_fwd1 | 5'-CAG TAC TGC GAC GGT CTA AGA GG-3' | [SEQ ID NO: 17] |
| YHSHLST_rev1 | 5'-GGT GGA GAG ATG ACT GTG GTA CC-3' | [SEQ ID NO: 18] |

| Primers used for amplification of 2 kbp fragment of LacGL1 gene from genomic DNA | | |
|---|---|---|
| IAPDGFT_fwd1<sup>c</sup> | 5'-CAT CGC TCC CGA TGG CTT CAC TC-3' | [SEQ ID NO: 19] |
| DLCTS_rev1<sup>c</sup> | 5'-CTG ACG TCG GGC AAA GAT CCG-3' | [SEQ ID NO: 20] |

| Primers used for amplification of a full nucleotide sequence of LacGL1 gene from cDNA | | |
|---|---|---|
| SLANPVPK_rev | 5'-CTT CGG CAC AGG GTT TGC TAG GGA G-3' | [SEQ ID NO: 21] |
| QKGTNWAD_fwd | 5'-CAG AAG GGC ACG AAC TGG GCT GAC-3' | [SEQ ID NO: 22] |
| LSVDDQ_rev | 5'-TAG CGC GGC CGC CTA TTA TCA TTG ATC ATC GAC CGA GAG CG-3' | [SEQ ID NO: 23] |
| MAKFQSL_fwd | 5'-ATG CGA ATT CAT GGC GAA GTT CCA ATC GTT GC-3' | [SEQ ID NO: 24] |
| α-FACTOR_fwd | 5'-ATG CGA ATT CGG CAT CGG TCC CAA GAC C-3' | [SEQ ID NO: 25] |

<sup>a</sup>The name of the primer was based on the corresponding amino acid region in the laccase of Ganoderma lucidum Q9GH17. The chosen amino acid regions for primers design were based on mRNA of laccase from G. lucidum Q9HG17.
<sup>c</sup>Underlined amino acids in the primer name represent single positional mutations in LacGL1 laccase as compared to laccase from G. lucidum Q9GH17.
Universal Primer kit: 5'ctaatacgactcactatagggc AAGCAGTGGTATCAACGCAGAGT-3' [SEQ ID NO: 26] and 5' ctaatacgactcactatagggc-3' [SEQ ID NO: 27]

The LacGL1 gene amplification with primer pair (WADGP_fwd3 and LINGLP_rev1) was carried out with 8 U of RUN polymerase (A&A Biotechnology, Poland) per volume of 25 μL. The PCR temperature program was initiated at 94° C. for 5 min., followed by 30 cycles of 94° C. for 30 s., 58° C. for 30 s., 72° C. for 2 min., and a final extension at 72° C. for 7 min. The PCT products were purified using QIAquick Gel Extraction Kit (QIAGEN, Denmark), subcloned and sent for sequencing in pCR®-BluntII-TOPO® vector.

PCR amplification yielded a 500 bp fragment of the LacGL1 gene, showing 80% nucleotide sequence identity to the mRNA sequence of *G. lucidum* Q9HG17, and comprising coding sequences encoding a region of the LacGL1 laccase positioned between the conserved peptides, TTSI-HWHGFFQ and FPLGSDSTLINGLG.

In order to extend the 500 bp cloned fragment, outward primers, QYCDGLR_fwd1 and YHSHLST_rev1 (Table 4), located within the cloned fragment, were used to amplify *G. lucidum* genomic DNA in combination with the fwd and rev partners, IAPDGFI_fwd1 and DLCTS_rev1, corresponding to the 5' and 3' end, respectively, of the *G. lucidum* Q9HG17 mRNA coding sequence. PCR amplification of LacGL1 gene was initiated by denaturation of the DNA strain at 96° C. for 30 s., followed by 35 cycles at 96° C. for 30 s., 63.4° C. for 30 s., 72° C. for 30 s., and a final extension at 72° C. for 5 min., with the following aliquots of the PCR reaction mixture: 0.25 µL of 2 U/µL Phusion polymerase (Finnzymes, Finland), 0.5 µL of 50 mM MgCl$_2$, 5 µL of 5×HF buffer, 0.2 µL 25 mM dNTPs (Fermentas, Denmark), 2.5 µL of 10 pmol/µL of corresponding P1 and P2 primer (see Table 1), and 1 µL of a properly diluted DNA.

PCR yielded a 1963 bp fragment of part of the LacGL1 laccase gene, corresponding to nucleotides 105-2067 of SEQ ID NO: 6. Manual and software analysis (Stanke, Morgenstern, 2005) of introns and exons in the gene (SEQ ID NO: 6), revealed the existance of 9 introns, located at 184-250, 320-369, 491-547, 662-722, 787-862, 959-1009, 1167-1218, 1417-1476, and 1741-1796 bp which all followed GT-AG rule at the exon/intron junctions, and had a characteristic for *Basidiomycetes* motif within the intron-CTNA.

4.4 Cloning the LacGL1 cDNA from *Ganderma lucidum* CBS229.93

The RACE technique, Ryu, et al. 2008, was used to clone sequences 5' and 3' to the cloned 1963 bp genomic fragment, in order to then obtain the full nucleotide sequence of LacGL1 cDNA from total RNA of *Ganoderma lucidum* CBS229.93.

The first strand cDNA library construction and the Rapid Amplification of cDNA Ends (RACE) experiment were carried out using SMARTer® RACE cDNA Amplification Kit (CloneTech, USA), and 5' and 3' RACE PCR fragments were generated using the Universal Primer Mix, as supplied in the kit, and gene specific primer QKGTNWAD_fwd or SLANPVPK_rev (Table 4), respectively, whose sequences are based on the partial nucleotide sequence of the LacGL1 gene. The RACE reaction cycle was as follows: 94° C. for 1 min.; five cycles of 94° C. for 30 s, 72° C. for 3 min.; five cycles of 94° C. for 30 s, 70° C. for 30 s, 72° C. for 3 min.; and 25 cycles of 94° C. for 30 s, 68° C. for 30 s, 72° C. for 3 min. The generated RACE products were cloned into pCR®-BluntII-TOPO® vector and sequenced. The overlap of 5' and 3' sequence fragments enabled assembling of the full coding sequence of LacGL1 gene. The obtained full nucleotide sequence of LacGL1 gene was then amplified from the cDNA library using MAKFQSL_fwd and LSVD-DQ_rev primer (Table 1) and sent off for sequencing in a pCR®-BluntII-TOPO® vector.

The determined nucleotide sequence of the LacGL1 cDNA (SEQ ID NO: 8) and the corresponding 1963 bp fragment of the LacGL1 gene, deprived of introns were identical. On the basis of the LacGL1 cDNA, the LacGL1 mRNA is 1563 nt in length.

Example 5

Characterisation of *Ganderma lucidum* CBS229.93 Laccase, LacGL1, Encoded by the LacGL1 Gene The LacGL1 polypeptide encoded by the LacGL1 laccase cDNA and gene (obtained by translation using an ExPASY translate tool, Gasteiger et al. 2005) has 520 amino acids (SEQ ID NO: 9) comprising a 21 amino acid long signal peptide and cleavage site, predicted by SignalP software (Nielsen, et al. 1997; Bendtsen, et al. 2004). The pI and the molecular mass of the native laccase (minus its signal peptide) was calculated to be 5.07 and 54.5 kDa; and the LacGL1 laccase (minus signal peptide) but containing a 27-amino-acid purification tag was calculated to be 5.21 and 57.5 kDa. This calculated molecular mass is slightly lower than that of the 62.5 kDa native LacGL1 laccase detected in SDS-PAGE (FIG. 2) and Native-PAGE (FIG. 3). This is presumably due to laccase glycosylation, since the LacGL1 sequence contains seven potential N-glycosylation sites, computed by NetNGlyc server (Blom, et al. 2004).

The deduced sequence of LacGL1, shared 91% amino acid sequence identity to *Ganoderma lucidum* strain 7071-9 laccase (Q9HG17-UniProt identifier), and 81% amino acid sequence identity to *Polyporus brumalis* laccase (A3F8Z8), respectively.

Analysis of the amino acid sequence of the LacGL1 laccase from *Ganoderma lucidum* CBS229.93 revealed a high degree of homology in the conserved copper binding domains, comprising amino acids that take part in coordination to four copper atoms (FIG. 5). These domains consist of four ungapped sequence regions, identified as R1-R4, that contain 1 cysteine and ten histidines as conserved residues that are involved in binding four copper ions (Thurston, 1994). Eight out of ten histidines appeared in a highly conserved pattern of HXH motifs (FIG. 5) in the protein. An X in this motif represents an undefined residue. Moreover, the HXH motifs were separated from each other by segments of 25 to 175 amino acids (Kumar, et al. 2003). The most important residues that coordinated to copper ions were located in domain 1 and 3.

Example 6

Recombinant Cloning and Expression of *Ganderma lucidum* CBS229.93 LacGL1 Gene in *Pichia pastoris*

The LacGL1 cDNA was cloned into an expression vector together with an α-factor signal peptide coding sequence from *Saccharomyces cerevisiae* (pMLα_LacGL1, FIG. 6) for directing the extracellular transport of the expressed LacGL1 protein, when expressed in *P. pastoris*.

6.1 Construction of an Expression Vector pMLα_LacGL1

The LacGL1 laccase cDNA was amplified using a proof-reading polymerase: Phusion® Hot Start II High-Fidelity DNA Polymerase (Finnzymes, Finland). The amplified laccase cDNA was sub-cloned with the nucleotide sequence encoding α-mating factor pre pro peptide from *Saccharomyces cerevisiae* (Brake, at al. 1983), using primers α-FAC-TOR_fwd and LSVDDQ_rev (Table 1), and the amplified product was digested with EcoRI and NotI and cloned to pPICZαA plasmid to generate pMLα_LacGL1 vector (FIG. 6). The pMLα_LacGL1 vector further comprises sequences encoding a c-myc epitope and a HIS tag (27 additional amino acids), which extend from the C-terminal end of the expressed laccase.

6.2 Expression of LacGL1 Laccase in *P. pastoris* X-33 and Visualization of its Secretion

*P. pastoris* strain X-33 was transformed by electrophoresis with pMLα_LacGL1 vector. Plasmid pPICZαA was used as a negative control for laccase expression (Invitrogen, Life Technologies Corporation, Carlsbad, Calif., USA). All expression vectors were linearized with PmeI (MssI) prior to the transformation. The transformant cells were selected on Yeast Extract Peptone Dextrose (YPDS) agar plates (1% yeast extract, 2% peptone, 2% dextrose, 1 M sorbitol, 2% agar) containing 100 μg/m L zeocin. The in-agar expression of LacGL1 laccase from positive *P. pastoris* transformants was detected by appearance of brown-red halos after 7 days growth at 30° C. on Buffered Minimal Methanol (BMM) agar plates (100 mM potassium phosphate, pH 6, 1.34% Yeast Nitrogen Base (YNB), $4 \times 10^{-5}$% biotin, 1% methanol, and 1.5% agar) supplemented with 0.3 mM $CuSO_4$ and 0.04% guaiacol.

Production of the recombinant LacGL1 laccase was also performed in liquid cultures prior to fermentation. Inoculation of the selected positive clones into Buffered Glycerol Medium (BGMY) medium (1% yeast extract, 2% peptone, 100 mM potassium phosphate, pH6, 1.34% YNB, $4 \times 10^{-5}$% biotin, 1% glycerol) was followed by incubation at 30° C. overnight in a shaking incubator. The cells were harvested when the $OD_{600}$ reached a value of 1, resuspended in Buffered Methanol Medium (BMMY) medium (1% yeast extract, 2% peptone, 100 mM potassium phosphate, pH 6, 1.34% YNB, $4 \times 10^{-5}$% biotin, 0.5% methanol) supplemented with 0.3 mM $CuSO_4$ and incubated for 5 days with an addition of methanol to a final concentration of 0.5%, every 24 h. The strain exhibiting the highest laccase specific activity for ABTS was chosen for fermentation.

6.3 Heterologous Production of LacGL1 Laccase by Recombinant *P. pastoris*

*P. pastoris* strain X-33 comprising the pMLα-LacGL1 vector was inoculated overnight at 30° C., at 150 rpm in the shaking flasks in BMG (Buffered Minimal Glycerol) medium (100 mM potassium phosphate, pH 6, 1.34% YNB, $4 \times 10^{-5}$% biotin, 1% glycerol) until the cell density reached a value of 1.7. This step was followed by inoculation of a 5 L Sartorius Biostat Aplus fermentor. The 5 L scale production of recombinant laccase in *P. pastoris* was performed essentially according to Stratton et al. (1999) and as detailed by Silva et al. (2011), except that the Methanol Fed-Batch phase was carried out at 20° C., to improve the enzyme stability. Agitation was kept below 750 rpm to avoid excessive cell disruption of the *P. pastoris* cells and in turn to limit the downstream purification process. Additional oxygen was added automatically to accommodate optimal growth and enzyme expression. The total time for the fermentation process was 112 h.

During the 5-L scale fermentation (112 h), the methanolytic yeast growth was monitored by measurement of the $OD_{600}$, which increased from 1.7 to 630, while the extracellular proteins, including the LacGL1, reached a concentration of 14.7 g/L. The fermentation broth was centrifuged at 5300×g 5° C. for 1 h, and the supernatant comprising total extracellular proteins was then sterile filtered, and the proteins concentrated by ultrafiltration, using a cross-flow bioreactor system with a 30 kDa cutoff membrane (Millipore, Sartorius, Denmark), as described by Silva et al. (Silva et al. 2011). The enzyme aliquots containing 25% (w/v) glycerol were stored at −80° C.

LacGL1 laccase activity was detected among the extracellular proteins expressed by recombinant *P. pastoris* fraction, that were separated by native PAGE and tested for in-gel laccase activity (FIG. 7) as described in Example 2, but using ABTS as substrate. The expressed LacGL1 laccase had a relatively high molecular mass of 125 kDa. EndoH treatment of the expressed LacGL1 laccase decreased its molecular mass to 62.5 kDa (FIG. 7), showing that the high mass was mainly due to extensive glycosylation of the *Pichia* expressed laccase.

Example 7

Method for Measuring Laccase Activity on Defined Substrates

The laccase activity was measured based on a modified method of Ters et al. (2009). The laccase activity was defined as the amount of the enzyme required to oxidise 1 μmol of ABTS per minute at 25° C., and pH 4.7. The assay mixture contained: 0.1 M citrate-phosphate buffer (255 μL, pH 4.7), ABTS (5 μL, 4 mM (ABTS stock solution)), and pre-diluted laccase (5 μL) that ensured the linear range of Michaelis-Menten kinetics. The oxidation of ABTS was monitored at 420 nm ($\epsilon_{420}$=36800 $M^{-1}cm^{-1}$) for 2 min. in an Infinite 200 microtiter plate reader (Tecan, Salzburg, Austria). Laccase activity assays on the substrates: hydroquinone (248 nm), 2.6-dimethoxyphenol (470 nm), and guaiacol (436 nm) was done similarly with the substrate concentration as described in Table 2 using the following extinction coefficient values: 17.542 $M^{-1}cm^{-1}$, 35.645 $M^{-1}cm^{-1}$, and 6.400 $M^{-1}cm^{-1}$, respectively (Minussi et al. 2007). The data collection was monitored by the program Tecan i-control version 1.5.14.0 (Tecan, Salzburg, Austria). The calculated laccase activity was corrected by the absorbance of a control sample which contained: 0.1 M citrate-phosphate buffer (255 μL, pH 4.7), ABTS (5 μL, 4 mM), and 5 μL of distilled water instead of the enzyme. All determinations of the laccase activity were performed in duplicates, with an average sample standard deviation less than 5%.

Example 8

Characterization of LacGL1 Laccase Expressed by Recombinant *P. pastoris*

The LacGL1 laccase activity expressed by recombinant *P. pastoris* was measured to be 17.5 U/mL after sterile filtration, according to the method in example 7.

8.1 Evaluation of the Influence of pH and Temperature on LacGL1 Laccase Activity The effect of the pH and temperature on the LacGL1 laccase activity was determined with a statistically designed, randomized, full factorial experiment as described in FIG. 8. The relative laccase activity was calculated based on the LacGL1 activity at pH 4.7 and 25° C. The highest relative activity was obtained at pH 4.7 (central area of the plot) and 55° C. and was almost temperature independent, while the lowest relative activity was seen at pH values below 6 (peripheral area of the plot). The model correlation coefficient $R^2$ (0.99) suggested that the fitted model could explain 99% of the total variation in the data. Together with the high values of predictivity $Q^2$ (0.97) and reproducibility (0.98) it could be concluded that the model was reliable.

The predicted optimal conditions for the LacGL1 laccase activity were validated by measuring the effect of temperature on the relative activity of LacGL1 laccase at pH 4.7. At temperatures of 25, 40, and even 50° C., activity did not change significantly within an hour, however temperatures of 60° C. and 70° C. lowered the laccase activity to 19 and 3%, respectively (FIG. 9). These results confirmed the model data in respect of a temperature range from 25° C. to 50° C. Additionally, the LacGL1 laccase showed a rather high stability at 50° C. and 40° C. for a prolonged time of incubation, retaining 33% activity after 24 h at 40° C. in contrast to 23% activity after 5 h at 50° C. (FIG. 10).

8.2 Substrate Specificity of LacGL1 Laccase

LacGL1 laccase was able to oxidize both ABTS and other phenolic compounds (Table 5) such as: hydroquinone, guaiacol, and 2.6-dimethoxyphenol, however in a slower rate than for ABTS. The comparison of the rate of product formation of the laccase from the crude extract of *G. lucidum* (LacGLCE), showed a similar pattern, however the expressed LacGL1 laccase was slightly faster.

TABLE 5

Substrate specificity of LacGL1 laccase.

| Substrate [1 mM] | Laccase relative rate of product formation [%][a] | |
|---|---|---|
| | LacGL1[b] | Lac_GLCE[c] |
| ABTS | 100 | 100 |
| Hydroquinone | 80 | 66 |
| Guaiacol | 66 | 57 |
| 2.6-Dimethoxyphenol | 61 | 51 |

[a]All values represent the mean of duplicate measurements with a relative difference between single measurements of <5%.
[b]Laccase from *Ganoderma lucidum*, expressed in *P. pastoris*,
[c]Laccase in *Ganoderma lucidum* crude extract, used as a reference for LacGL1 laccase.

The LacGL1 laccase $K_m$ value for ABTS as substrate was calculated to be 0.122 mM, from a Hanes-Wolf plot testing 5 µL of LacGL1 laccase preparation with an ABTS concentration range of: 0.015, 0.031, 0.041, 0.062, 0.077, and 0.092 mM.

8.3 Inhibitors of LacGL1 Laccase

LacGL1 laccase and the laccase from the crude extract of *G. lucidum* were strongly inhibited by sodium azide (0.01 and 0.1 mM) and dithiothreitol (0.5 mM), but at a lower but significant level by sodium fluoride, as shown in Table 6. EDTA affected the laccase activity to a lesser extent.

TABLE 6

The effect of the inhibitory substances on the oxidation of ABTS by the LacGL1 laccase from *Ganoderma lucidum*, expressed in *Pichia pastoris*.

| Compound | Concentration [mM] | Inhibition [%][a] | |
|---|---|---|---|
| | | LacGL1 | Lac_GLCE |
| Sodium azide | 0.0001 | 16 | 18 |
| | 0.0005 | 50 | 47 |
| | 0.001 | 57 | 57 |
| | 0.01 | 100 | 89 |
| | 0.1 | 100 | 100 |
| Sodium fluoride | 0.0001 | 8 | 23 |
| | 0.0005 | 13 | 24 |
| | 0.001 | 19 | 28 |
| | 0.01 | 22 | 38 |
| | 0.1 | 46 | 56 |
| EDTA | 50 | 16 | 30 |
| Dithiothreitol | 0.5 | 100 | 100 |

Example 9

Composition of Sugarcane Bagasse Prior to and after Pre-treatment by Steam Explosion SCB (Sugarcane Bagasse) was obtained from the commercial American Society of Sugarcane Technologists, Florida Division (LaBelle, Fla., USA). The raw biomass was washed in the distilled water to remove any sand particles and dried at 50° C., prior to the pretreatment. Afterwards, 15% dry matter (w/v) of SCB was pretreated by the steam explosion process at 175° C. for 10 min., 11 bars pressure, and a double addition of oxygen (3 min. each session) as described previously (Sorensen et al. 2007). After the steam explosion, the filter cake and the hydrolysate were mixed together, dried at 55° C. for 44 h, and coffee-milled to pass a sieve size of 210 µm (Endecotts, London, UK). The pretreated SCB (STEX-SCB) contained; 48.8% (w/w) cellulose, 13.8% (w/w) hemicellulose, and 19.3% (w/w) insoluble lignin.

The content of the dry matter and the biomass composition was determined according to the National Renewable Energy Laboratory (NREL) procedure (Sluiter et al. 2010). The levels of glucose and xylose liberated after strong acid hydrolysis were determined by HPAEC using Dionex BioLC system equipped with Dionex CarboPac PA1 analytical column (Dionex, Sunnyvale, Calif., USA) and an electrochemical detector used in the pulsed amperiometric detection mode principally as described previously (Sorensen et al. 2003).

Example 10

LacGL1 Laccase Enhances Cellulase-mediated Hydrolysis of Pretreated Sugarcane Bagasse The ability of recombinant expressed LacGL1 laccase to enhance cellulose mediated hydrolysis of pre-treated Sugarcane Bagasse to fermentable sugars was tested in combination with commercially available cellulose compositions.

10.1 Determination of Glucose Release as a Measure of Laccase-Cellulase Catalyzed Hydrolysis of Pre-Treated (Steam Exploded) Sugarcane Bagasse.

5% (w/v) dry matter of pretreated SCB (STEX SCB) was evaluated in 0.1 M citrate-phosphate buffer at pH 4.7 and 40° C. (optimal for the LacGL1 laccase) or pH 5.1 and 50° C. (optimal for the cellulase preparations), respectively. The commercially available cellulase cocktail preparations: Cellic® CTec1 and Cellic® CTec2 (0.064% Enzyme/Substrate ratio (E/S), w/w; Novozymes, Bagsværd, Denmark) were used with the combination of the LacGL1 laccase (0.4% E/S, w/w). The hydrolysis reactions were collected after 0, 1, 3, 5, 16, and 24 hours and stopped by incubation at 99° C. for 15 min. The samples were then centrifuged at 10.000 rpm for 2 min., the supernatants were filtered through 0.2 µm filter and the yields of released glucose were quantified using the D-glucose-HK kit (Megazyme, Denmark). The glucose yields released over time were corrected for the glucose content of the hydrolysis sample at time 0. The E/S dosage was based on the total protein concentration used. The protein quantification was performed using the Pierce BCA (BiCinchoninic Acid) protein assay kit microplate procedure according to manufacturer's instructions (Thermo Fisher Scientific, Rockford, US) using Bovine serum albumin (BSA) was used as a standard, as described before (Silva et al. 2011). The Cellic® CTec1 (CC1) and Cellic® CTec2 (CC2), cellulase preparations, are based on the *Trichoderma reesei* cellulase complex (exo-glucanase, endo-glucanase, and β-glucosidase activities) with additional β-glucosidase and glycoside hydrolase family 61 hydrolyse boosting proteins (Harris 2010). All determinations of the enzymatic hydrolysis samples were performed in duplicates.

10.2 LacGL1 Laccase Enhanced Hydrolysis of Pretreated (Steam Exploded) Sugarcane Bagasse by Cellulase Release of glucose during cellulose hydrolysis of STEX SCB is enhanced by the addition of LacGL1 laccase in a dosage dependent manner (data not shown). The combined laccase plus cellulase treatment of STEX SCB were performed at two different conditions: Firstly, at pH 4.6, 40° C. which is optimal for the LacGL1 laccase (as previously shown from MODDE pH-temp.-activity model, FIG. 8 and thermal stability plots, FIGS. 9, 10), which are slightly less optimal for cellulases; and secondly at 50° C. and pH 5.1, which are the golden standard conditions for optimal performance of CC1 and CC2. From the MODDE data, three different effects on glucose levels were observed and depended on the three factors: the type of the cellulase preparation, the addition of LacGL1, the temperature, and the pH of the reaction (FIG. 11, 12). Overall, the highest rate of STEX SCB hydrolysis, considering all of the aforementioned factors, was obtained for the combination of LacGL1-Cellic® CTec2 at pH 5.1 and 50° C. The total glucose yields were 19, and 27.5% higher, as compared with CC2 (alone) mediated-hydrolysis under the same conditions, and at pH 4.6 and 40° C., respectively. The higher pH and temperature enhanced LacGL1-CC2 catalyzed hydrolysis by 12% (FIG. 12).

LacGL1 also enhanced CC1 mediated-hydrolysis at pH 4.6 and 40° C. by 30% (FIG. 11). For this enzyme combination, the optimal conditions were pH 4.6 and 40° C., giving an improvement in glucose yields of 48%, and 66% over LacGL1-CC1 and CC1 hydrolyzed samples at pH 5.1 and 50° C.

Example 11

Recombinant Cloning and Expression of *Ganderma lucidum* GLlac1 in *Pichia pastoris*

11.1 Cloning *Ganoderma lucidum* Laccase GLlac1 in *Pichia pastoris*

The *Ganoderma lucidum* GLlac1 cDNA (Gen Bank accession No. FJ656307) encoding a GLlac1 laccase comprising its native signal peptide was downloaded from Gen Bank (http://www.ncbi.nlm.nih.gov/nucleotide/224037823?report=genbank&log$=nuclalign&blas t_rank=1&RID=2XPBZ0Z4015). The 1,497-bp GLlac1 coding sequence (SEQ ID NO: 28) encoding a GLlac1 laccase (SEQ ID NO: 29) was synthesized by DNA 2.0 (Menlo Park, USA) and the synthetic coding sequence was ligated into plasmid pJ912 and cloned in *E. coli* DH5α. The purified plasmid pJ912 was linearized by digestion with enzyme MssI and then transformed into competent cells of *P. pastoris* by electroporation (Bio-Rad Genepulser, Hercules, USA). Methanol-induced expression of the synthetic GLlac1 coding sequence in the transformed *P. pastoris* host was driven by the AOX1 promoter. After electroporation, *P. pastoris* cells were plated on YPD plates (1% yeast extract, 2% peptone, 0.4% dextrose, 2% agar) containing Zeocin (100 μg ml-1) and positive transformants screened on indicator agar plates with BMM agar (100 mM potassium phosphate buffer, pH 6.0, 3.4 g L-1 yeast nitrogen base without amino acids, 400 μg L-1 biotin, 0.5% methanol and 2% agar) containing 0.2 mM ABTS and 0.1 mM $CuSO_4$ at 30° C. for 96 h.

11.2 Production of Recombinant *G. lucidum* GLlac1 Laccase in *P. pastoris*

A Sartorious (BIOSTAT® Aplus) fermenter (Sartorius AG, Goettingen, Germany) with a total volume of 4 L was used for fed-batch fermentations at 25° C. following the "*Pichia* Fermentation Process Guidelines" from Invitrogen with slight modifications. The basal salts medium was supplemented with 0.1 mM CuSO4 and *Pichia* trace metal (PTM1) salts. The batch fermentation (2.5 L starting volume) was inoculated with 200 mL preculture of recombinant *P. pastoris*-33 comprising the GLlac1 coding sequence, in Invitrogens Shake Flask Medium. Air flow was kept constant at 4 L min$^{-1}$ and the stirrer speed was set to maximum 800 rpm. The pH was maintained at 5.0 with $NH_4OH$ and DO was set to 25% saturation and controlled by stirring and gas enrichment using pure oxygen. After depletion of glycerol in the batch medium the fed-batch phase was started with a constant feed of 100 mL 50% glycerol containing 12 mL L$^{-1}$ PTM1 at 0.6 mL h$^{-1}$. After the glycerol fed-batch phase, a pulse of 4 mL methanol containing 12 mL L$^{-1}$ PTM1 salts was added for fast induction. Hereafter the methanol feed rate was gradually accelerated to 0.41 mL h$^{-1}$ by decreasing temperature at 20° C. Harvest samples were taken for measurement of laccase activity and total soluble protein content. Antifoam was injected manually as required throughout the fermentation.

The fermentation broth from the recombinant *P. pastoris* was centrifuged at 5300×g 5° C. for 1 h, and the supernatant comprising total extracellular proteins was then sterile filtered, and the proteins concentrated by ultrafiltration, as described by Silva et al. (Silva et al. 2011). The enzyme aliquots containing 25% (w/v) glycerol were stored at −80° C.

GLlac1 laccase activity was detected among the extracellular proteins expressed by recombinant *P. pastoris*. The expressed and secreted mature GLlac1 laccase corresponds to amino acid residues 22-520 of SEQ ID NO: 28, from which the signal peptide has been removed.

Example 12

The *Ganoderm lucidum* LacGL1 and GLlac1 Laccases Significantly Greater Enhancement of Cellulase-Mediated Hydrolysis of Biomass Compared to Other Microbial Laccases Used in the Biomass Industry The ability of LacGL1 and GLlac1 (Q9HG17) laccases from *G. lucidum* to enhance cellulase-mediated hydrolysis of lignocellulose biomass was compared with the widely used commercial fungal laccases from *Agaricus bisporus, Pleurotus ostreatus* and, *Trametes versicolor*. The enzymes were tested on three different forms of biomass.

12.1 Biomass Hydrolysis Mediated by a Cellulase with and without a Selected Laccase The commercial fungal laccases were purchased as lyophilized protein samples from Sigma Aldrich. A solution of each of the above 5 laccases was prepared in a citric buffer containing 20% of glycerol (pH 5.1, 100 mM). The laccase activity of each laccase was measured with ABTS (2,2'-Azino-bis(3-ethylbenzothiazolin-6-sulfonic acid)-diazonium salt) as a substrate at 420 nm ($\epsilon$=36,000 M−1 cm−1) to ensure that comparable amounts of enzyme were used in the comparative tests.

Two different commercially available cellulase enzyme preparations used in the comparative study were "Cellulase 1" and "Cellulase 2", which were tested in combination with each of the laccases listed above.

The three different types of pretreated biomass used in the comparative study were sugarcane bagasse, barley straw and wheat straw. The source and pre-treatment of the sugarcane bagasse by steam explosion was as set out in Example 9. The barley straw and wheat straw used was grown and harvested in Denmark, and then subjected to a three-stage pretreatment process, comprising a triple heating treatment of the straw (whole bales) involving: heating straw having approximately 16% dry matter at 60° C. for 15 min; liquids were then removed from the product by heating to 180° C. for 10 min; followed by heating to 195° C. for 3 min (as described in Rosgaard et al, 2007). The composition of the dry and the pretreated biomass were determined according to the US National Renewable Energy Laboratory (NREL) procedures (Sluiter et al, 2010).

The laccase-cellulase catalyzed hydrolysis of the pretreated biomass samples to release glucose was performed as follows: Hydrolysis of 5% (w/v) samples of pretreated sugarcane bagasse, barley straw, and wheat straw biomass were assayed using an Enzyme/Substrate (E/S) ratio of 0.064% w/w for laccases and of 0.4% w/w for each commercial cellulase preparation in each hydrolysis reaction. The E/S dosage was based on the total protein concentration used, as determined using Pierce BCA (BiCinchoninic Acid) protein assay kit microplate procedure according to manufacturer's instruction (Thermo Fisher Scientific, Rockford, US).

Hydroysis samples were incubated in triplicate for 30 hours at pH 5.1 (100 mM), 50° C. on a thermomixer set to 800 rpm. The samples were collected after 0, 1, 3, 5, 24 and 30 hours and the hydrolysis reaction terminated by incubation at 99° C. for 15 min. Samples were then centrifuged at 10,000 rpm for 2 minutes, and the supernatants were removed and filtered through a 0.2 μm filter. The amount of released glucose in the filtrate was determined spectrophotometrically using a Chromogen glucose oxidase/peroxidase reagent (GOPOD) (Megazyme International Ireland Ltd, Wicklow, Ireland). The glucose yields released over time were corrected for the amount of glucose present in the hydrolysis sample at time 0. Data are given as averages of triplicate replica+/− standard deviation.

12.2 LacGL1 and GLlac1 Laccase Significantly Enhance Cellulase-mediated Hydrolysis of a Range of Pretreated Biomass Laccase and cellulase-mediated hydrolysis of the 3 biomass forms, measured as glucose release, are shown graphically in FIGS. 13, 14 and 15. The efficacy of the different enzyme combinations for enhancing glucose release for the 3 biomass samples at the 30 hour time point was subjected to statistical analysis.

Sugarcane bagasse: Glucose release by combination of LacGL1 or GLlac1 with cellulase (cellulase 1 or 2) was the same, and was significantly enhanced compared to a combination of any one of the other tested laccases with the two cellulases ($p<0.05$).

Barley straw: Glucose release by LacGL1 was significantly greater than GLlac1 when combined with cellulase (cellulase 1 or 2) ($p<0.05$); while both LacGL1 and GLlac1 gave significantly enhanced glucose release compared to a combination of any one of the other tested laccases with the two cellulases ($p<0.05$).

Wheat straw: Glucose release by a combination of LacGL1 or GLlac1 with cellulase (cellulase 1 or 2) was the same, but was significantly enhanced compared to a combination of any one of the other tested laccases with the two cellulases ($p<0.05$).

CITED REFERENCES

Apweiler R, Bairoch A, Wu C H, Barker W C, Boeckmann B, Ferro S, Gasteiger E, Huang H, Lopez R, Magrane M, Martin M J, Natale D A, O'Donovan C, Redaschi N, Yeh L-SL. (2004) UniProt: the Universal Protein knowledgebase. Nucleic Acid Res.; 32: D115-D119.

Bendtsen J D, Nielsen G, von Heijne G, Brunak S (2004) Improved prediction of signal peptides: SignalP 3.0. J. Mol. Biol 340:783-795.

Blom N, Sicheritz-Ponten T, Gupta R, Gameltoft S, Brunak S. (2004) Prediction of post-translational glycosylation and phosphorylation of proteins from amino acid sequence. Proteomics 4:1633-1649.

Bourbonnais R, Paice M G. (1992) Demethylation and delignification of kraft pulp by *Trametes versicolor* laccase in presence of 2.2'-azinobis-(3-ethylbenzthiazoline-6-sulphonate). Appl Microbiol Biotechnol. 36:823-827.

Brake A J, Julius D J, Thorner J (1983) A functional prepro-aloha-factor gene from *Saccharomyces cerevisiae* can contain 3, 4, or 5 repeats of the mature pheromone sequence. Mol Cell Biol 3:1440-1450.

Bulter T, Alcalde M, Sieber V, Meinhold P, Schlachtbauer C, Arnold F H. (2003) Functional expression of a fungal laccase in *Saccharomyces cerevisiae* by directed evolution. Appl Environ Microbiol.; 69(2):987-995.

Chandel A K, Kapoor R K, Singh A Kudah R C (2007) Detoxification of sugar cane bagasse hydrolysates improves ethanol production by *Candida shehatae* NCIM 3501. Biores Technol 98:1947-1950.

Garzillo A M V, Colao M C, Caruso C, Caporale C, Celleti D. Buonocore V. (1998) Laccase from the white-rot fungus *Trametes trogii*. Appl Microbiol Biotechnol.; 49:545-551.

Gasteiger E, Hoogland C, Gattiker A, Duvaud S, Wilkins M R, Appel R D, Bairoch A (2005) Protein identification and analysis tool on the ExPASY server. p. 571-607, In J. M. Walker (ed.), The Proteomics Protocols Handbook. Humana Press Inc., Totowa, N.J.

Gouet P, Coufcelle E, Stuart DI, Métoz F (1999) ESPript: analysis of multiple sequence alignments in PostScript. Bioinformatics 15:305-8

Goujon M, McWilliam H, Weizhong L, Valentin F, Squizzato S, Paern J, Loperz R (2010) A new bioinformatics analysis tools framework at EMBL-EBI. Nucl Acid Res W695-W9.

Harkin J M, Larsen M J, Obst J R. (1974) Use of syringaldazine for detection of laccase in sporophores of wood rotting fungi. Mycologia; 66(3):469-476.

Harris P V, Weiner D, McFarland K C, Re E, Navarro Poulsen J C, Brown K, Salbo R, Ding H, Vlasenko E, Merino S, Xu F, Cherry J, Larsen S, Leggio LL (2010) Stimulation of lignocellulosic hydrolysis by proteins of glycoside hydrolase family 61: Structure and function of large, enigmatic family. Biochem 49:3305-3316.

Hoopes J, Dean J F D. (2001) Staining electrophoretic gels for laccase and peroxidase activity using 1.8-Diaminonaphthalene. Anal Biochem.; 293:96-101.

Joo S S, Ryu I W, Park J-K, Yoo Y M, Lee D-H, Hwang K W, Coi H-T, Lim C-J, Kim K (2007) Molecular cloning and expression of laccase from *Ganoderma lucidum*, and its antioxidative properties. Mol Cells 25(1):112-118.

Jurado M, Prieto A, Martinez-Alcalá Á, Martinez Á, Martinez M J (2009) Laccase detoxification of steam-exploded wheat straw for second generation bioethanol. Bioresource Technology 100:6378-6384.

Ko E-M, Leem Y-E, Choi H T. (2001) Purification and characterization of laccase isozymes from the white-rot basidiomycete *Ganoderma lucidum*. Appl Microbiol Biotechnol.; 57:98-102.

Kumar S V S, Phale P S, Durani S, Wangikar PP (2003) Combined sequence and structure analysis of the fungal laccase family. Biotechnol Bioeng 83:386-94.

Lee S B, Taylor J W (1990) Isolation of DNA from fungal mycelia and single spores. PCR protocols: A guide to methods and applications 282-287.

Moilanen U, Kellock M, Galkin S, Viikari L (2011) The laccase-catalysed modification of lignin for enzymatic hydrolysis. Enzyme and Microbiol Technology 49:492-498.

Nielsen H, Engelbrecht J, Brunak S, von Heijne G (1997) Identification of prokaryotic and eukaryotic signal peptides and prediction of their cleavage sites. Protein Eng 10:1-6.

Palmieri G, Giardina P, Bianco C, Scaloni A, Capasso A, Sannia A. (1997) A novel laccase from *Pleurotus ostreatus*. J Biol Chem.; 272(50):31301-31307.

Palonen H, Viikari L (2004) Role of oxidative enzymatic treatments on enzymatic hydrolysis of softwood. Biotechnol Bioengin 86(5):550-557.

PIONTEK, K.; ANTORINI, M. and CHOINOWSKI, T. (2002). Crystal structure of a laccase from the fungus *Trametes versicolor* at 1.90 Å resolution containing a full complement of coppers. The Journal of Biological Chemistry, vol. 277, no. 40, p. 37663-37669

Rosgaard L, Pedersen S, Meyer A S. Comparison of different pretreatment strategies for enzymatic hydrolysis of wheat and barley straw. Appl Biochem Biotechnol (2007) 143:284-296.

Ryde J P. (1980) The effect of induced lignifications on the resistance of wheat cell walls to fungal degradation. Phys. Plant Pathology.; 16:187-196.

Ryu S-H, Lee A-Y, Kim M (2008) Molecular characterization of two laccase from the *basidiomycete* fungus *Polyporus brumalis*. J. Microbiol 46(1):62-69.

Schiøt M, Rogowska-Wrzesinska A, Roepstorff P, Boomsma JJ. (2010) Leaf-cutting ant fungi produce cell wall degrading pectinase complex reminiscent of phytopathogenic fungi. BMC Biol.; 156:1-12.

Silva I R, Larsen D M, Meyer A S, Mikkelsen JD (2011) Identification, expression, and characterization of a novel bacterial RGI lyase enzyme for the production of biofunctional fibers. Enz Microb Technol 49:160-6.

Sluiter A, Hames B, Ruiz R, Scarlata C, Sluiter J, Templeton D, Crocker P. Determination of structural carbohydrates and lignin in biomass. Laboratory analytical procedure (LAP), NREL/TP-510-42618, 2011:1-15; revised June 2010.

Soden D M, O'Callaghan J, Dobson ADW. (2002) Molecular cloning of laccase isozyme gene from *Pleurotus sajor-caju* and expression in the heterologous *Pichia pastoris* host. Microbiol.; 148:4003-4014.

Stanke M, Morgenstern B (2005) AUGUSUS: a web server for gene prediction in eukaryotes that allows a user-defined constraints. Nuc Acid Res 33:W465-W467.

Stratton J, Chiruvolu V, Meagher M (1999) High-well density fermentation. In: Higgins D, Gregg J, editors. *Pichia* protocols, vol. 103. Totowa, N.J., USA: Humana Press p. 109-20.

Sørensen A, Teller P J, Hilstrøm T, Ahring BK (2008) Hydrolysis of Miscanthus for bioethanol production using dilute acid presoaking combined with explosion pre-treatment and ezymatic treatment. Biores Technol 99(14):6602-6607.

Sørensen H R, Meyer A S, Pedersen S., (2003) Enzymatic hydrolysis of water-soluble wheat arabinoxylan. I. Synergy between α-L-arabinofuranosidases, endo-1,4-β-xylanase, and β-xylosidase activities. Biotechnol Bioeng 81:726-731.

Thaysen-Andersen M, Mysling S, Højrup P., (2009) Site-specific glycoprofiling of N-linked glycopeptides using MALDI-TOF MS: Strong correlation between signal strength and glycoform quantities. Anal Chem.; 81:3933-3943.

Ters T, Kuncinger T, Srebotnik E., (2009) Carboxylic acids used in common buffer systems inhibit the activity of fungal laccases. J Mol Cat B: Enz 61:261-267.

Thurston C F., (1994) The structure and function of fungal laccases. Microbiol 140:19-26.

Sun J, Peng R H, Xiong A-S, Tian Y, Zhao W, Xu H, Liu D-T, Chen J-M, Yao Q-H (2012) Secretory expression and characterization of a soluble laccase from the *Ganoderma lucidum* strain 7071-9 in *Pichia pastoris*. Mol. Biol Rep 39:3807-3814

Wang H X and Ng T B (2006) A laccase from the medicinal mushroon *Ganoderma lucidum*. Appl. Micrbiol Biotechnol 72: 508-513

Wolfenden B S, Willson R L. (1982) Radical-cations as reference chromogens in kinetic studies of one-electron transfer reactions: Pulse radiolysis studies of 2.2'-azinobis-(3-ethylbenzthiazoline-6-sulphonate). J Chem Soc Perkin Trans.; II: 805-812.

Xu F, Shin W, Brown SH, Wahlethner JA, Sundaram UM, Solomon EI. (1996) A study of a series of recombinant fungal laccases and bilirubin oxidase that exhibit significant differences in redox potential, substrate specificity, and stability. Biochimica et Biophysica Acta.; 1292:303-311.

The invention claimed is:

1. A method for enhancing enzymatic hydrolysis of lignocellulose biomass, comprising the steps of:
   a. providing an aqueous dispersion of biomass;
   b. adding a preparation of fungal laccase to the biomass (a);
   c. adding a preparation of one or more cellulose hydrolysing enzyme to the biomass (b), wherein the addition in step b) is either simultaneous with the addition in step c), or is prior to the addition in step c);
   d. incubating the biomass of step b) and step c) either simultaneously or in sequence; wherein the fungal laccase is a polypeptide comprising the amino acid sequence of SEQ ID NO: 5.

2. The method for enzymatic hydrolysis of lignocellulose biomass of claim 1, comprising a further step (e) of separating the soluble biomass from the product of step d) in order to obtain a soluble aqueous hydrolysate.

3. The method for enzymatic hydrolysis of lignocellulose biomass of claim 1, wherein the one or more cellulose hydrolysing enzyme is selected from among an endo-β-1,4-glucanase (EC 3.2.1.4), exoglucanase (EC 3.2.1.91) and β-glucosidase (EC 3.2.1.21).

4. The method for enzymatic hydrolysis of lignocellulose biomass of claim 1, wherein the biomass is subjected to pre-treatment with one or more of heat, pressure and steam in order to partially degrade and solubilize the lignocellulose.

5. The method for enzymatic hydrolysis of lignocellulose biomass of claim 1, wherein step (d) is performed at a pH of between 4.2 and 5.2.

6. The method for enzymatic hydrolysis of lignocellulose biomass of claim 1, wherein step (d) is performed at a temperature of between 40° C. and 50° C.

7. The method for enzymatic hydrolysis of lignocellulose biomass of claim 1, wherein the incubation of step (d) has a duration of 16 hours or more.

8. The method for enzymatic hydrolysis of lignocellulose biomass of claim 1, wherein the amino acid sequence of the fungal laccase (EC 1.10.3,2) is at least 499 amino acid residues in length.

\* \* \* \* \*

SEQUENCE LISTING

```
<160> NUMBER OF SEQ ID NOS: 29

<210> SEQ ID NO 1
<211> LENGTH: 24
<212> TYPE: PRT
<213> ORGANISM: Ganoderma lucidum
<220> FEATURE:
<221> NAME/KEY: PEPTIDE
<222> LOCATION: (1)..(24)
<223> OTHER INFORMATION: LacGL1 laccase peptide R1

<400> SEQUENCE: 1

His Trp His Gly Phe Phe Gln Lys Gly Thr Asn Trp Ala Asp Gly Pro
1               5                   10                  15

Ala Phe Ile Asn Gln Cys Pro Ile
            20
```

```
<210> SEQ ID NO 2
<211> LENGTH: 22
<212> TYPE: PRT
<213> ORGANISM: Ganoderma lucidum
<220> FEATURE:
<221> NAME/KEY: PEPTIDE
<222> LOCATION: (1)..(22)
<223> OTHER INFORMATION: LacGL1 laccase peptide R2

<400> SEQUENCE: 2

Gly Thr Phe Trp Tyr His Ser His Leu Ser Thr Gln Tyr Cys Asp Gly
1               5                   10                  15

Leu Arg Gly Pro Phe Val
            20

<210> SEQ ID NO 3
<211> LENGTH: 8
<212> TYPE: PRT
<213> ORGANISM: Ganoderma lucidum
<220> FEATURE:
<221> NAME/KEY: PEPTIDE
<222> LOCATION: (1)..(8)
<223> OTHER INFORMATION: LacGL1 laccase peptide R3

<400> SEQUENCE: 3

His Pro Phe His Leu His Gly His
1               5

<210> SEQ ID NO 4
<211> LENGTH: 22
<212> TYPE: PRT
<213> ORGANISM: Ganoderma lucidum
<220> FEATURE:
<221> NAME/KEY: PEPTIDE
<222> LOCATION: (1)..(22)
<223> OTHER INFORMATION: LacGL1 laccase peptide R4

<400> SEQUENCE: 4

Gly Pro Trp Phe Leu His Cys His Ile Asp Phe His Leu Glu Ala Gly
1               5                   10                  15

Phe Ala Val Val Phe Ala
            20

<210> SEQ ID NO 5
<211> LENGTH: 499
<212> TYPE: PRT
<213> ORGANISM: Ganoderma lucidum
<220> FEATURE:
<221> NAME/KEY: mat_peptide
<222> LOCATION: (1)..(499)
<223> OTHER INFORMATION: Mature LacGL1 laccase (minus signal peptide)

<400> SEQUENCE: 5

Gly Ile Gly Pro Lys Thr Asp Leu Thr Ile Ser Asn Ala Asp Val Ala
1               5                   10                  15

Pro Asp Gly Tyr Thr Arg Ala Ala Val Val Asn Gly Val Phe Pro
            20                  25                  30

Ala Pro Leu Ile Thr Gly Asn Lys Gly Asp Arg Phe Gln Leu Asn Val
            35                  40                  45

Ile Asp Gln Met Thr Asn His Thr Met Leu Lys Ser Thr Ser Ile His
        50                  55                  60

Trp His Gly Phe Phe Gln Lys Gly Thr Asn Trp Ala Asp Gly Pro Ala
65                  70                  75                  80
```

```
Phe Ile Asn Gln Cys Pro Ile Ser Ser Gly His Ser Phe Leu Tyr Asp
                85                  90                  95
Phe Gln Val Pro Asp Gln Ala Gly Thr Phe Trp Tyr His Ser His Leu
            100                 105                 110
Ser Thr Gln Tyr Cys Asp Gly Leu Arg Gly Pro Phe Val Val Tyr Asp
            115                 120                 125
Pro Lys Asp Pro Leu Lys Lys Leu Tyr Asp Ile Asp Asp Ser Thr
            130                 135                 140
Val Ile Thr Leu Thr Asp Trp Tyr His Val Ala Ala Arg Leu Gly Pro
145                 150                 155                 160
Arg Phe Pro Leu Gly Ser Asp Ser Thr Leu Ile Asn Gly Leu Gly Arg
                165                 170                 175
Ser Thr Thr Asn Val Thr Ala Asp Leu Ala Val Ile Asn Val Thr Gln
            180                 185                 190
Gly Lys Arg Tyr Arg Phe Arg Leu Val Ser Leu Ser Cys Asp Pro Asn
            195                 200                 205
Tyr Thr Phe Ser Ile Asp Asp His Asn Met Thr Val Ile Glu Ala Asp
            210                 215                 220
Gly Ile Glu Thr Gln Pro Val Thr Val Asn Ala Ile Gln Ile Phe Ser
225                 230                 235                 240
Ala Gln Arg Tyr Ser Phe Val Leu Thr Ala Asn Gln Thr Ile Asp Asn
                245                 250                 255
Tyr Trp Ile Arg Ala Asn Pro Asn Phe Gly Asn Val Gly Phe Thr Asp
                260                 265                 270
Gly Ile Asn Ser Ala Ile Leu Arg Tyr Ala Gly Ala Asp Pro Val Glu
            275                 280                 285
Pro Thr Thr Ser Gln Gln Thr Thr Gln Asn Leu Leu Asn Glu Val Asp
            290                 295                 300
Leu His Pro Phe Val Pro Lys Arg Thr Pro Gly Gln Pro Thr Gln Gly
305                 310                 315                 320
Gly Val Asp Thr Ala Ile Asn Met Val Phe Asn Phe Asn Gly Ser Asn
                325                 330                 335
Phe Phe Ile Asn Asn Ala Ser Phe Val Pro Pro Thr Val Pro Val Leu
                340                 345                 350
Leu Gln Ile Leu Ser Gly Ala Gln Ala Ala Gln Asp Leu Leu Pro Ser
            355                 360                 365
Gly Ser Val Tyr Thr Leu Pro Val Asn Lys Ser Ile Glu Leu Thr Phe
            370                 375                 380
Pro Ala Thr Ala Asn Ala Pro Gly Ala Pro His Pro Phe His Leu His
385                 390                 395                 400
Gly His Ala Phe Ala Val Val Arg Ser Ala Gly Ser Thr Val Tyr Asn
                405                 410                 415
Tyr Asp Asn Pro Val Trp Arg Asp Val Val Ser Thr Gly Thr Pro Ala
                420                 425                 430
Ala Gly Asp Asn Val Thr Ile Arg Phe Gln Thr Asp Asn Pro Gly Pro
            435                 440                 445
Trp Phe Leu His Cys His Ile Asp Phe His Leu Glu Ala Gly Phe Ala
                450                 455                 460
Val Val Phe Ala Glu Asp Pro Thr Asp Thr Ser Leu Ala Asn Pro Val
465                 470                 475                 480
Pro Lys Ala Trp Ser Asp Leu Cys Pro Thr Tyr Asp Ala Leu Ser Val
                485                 490                 495
Asp Asp Gln
```

```
<210> SEQ ID NO 6
<211> LENGTH: 2093
<212> TYPE: DNA
<213> ORGANISM: Ganoderma lucidum
<220> FEATURE:
<221> NAME/KEY: gene
<222> LOCATION: (1)..(2093)
<223> OTHER INFORMATION: LacGL1 gene
<220> FEATURE:
<221> NAME/KEY: exon
<222> LOCATION: (1)..(183)
<220> FEATURE:
<221> NAME/KEY: Intron
<222> LOCATION: (184)..(250)
<223> OTHER INFORMATION: Intron 1
<220> FEATURE:
<221> NAME/KEY: exon
<222> LOCATION: (251)..(319)
<220> FEATURE:
<221> NAME/KEY: Intron
<222> LOCATION: (320)..(369)
<223> OTHER INFORMATION: Intron 2
<220> FEATURE:
<221> NAME/KEY: exon
<222> LOCATION: (370)..(490)
<220> FEATURE:
<221> NAME/KEY: Intron
<222> LOCATION: (491)..(547)
<223> OTHER INFORMATION: Intron 3
<220> FEATURE:
<221> NAME/KEY: exon
<222> LOCATION: (548)..(661)
<220> FEATURE:
<221> NAME/KEY: Intron
<222> LOCATION: (662)..(722)
<223> OTHER INFORMATION: Intron 4
<220> FEATURE:
<221> NAME/KEY: exon
<222> LOCATION: (723)..(786)
<220> FEATURE:
<221> NAME/KEY: Intron
<222> LOCATION: (787)..(862)
<223> OTHER INFORMATION: Intron 5
<220> FEATURE:
<221> NAME/KEY: exon
<222> LOCATION: (863)..(958)
<220> FEATURE:
<221> NAME/KEY: Intron
<222> LOCATION: (959)..(1009)
<223> OTHER INFORMATION: Intron 6
<220> FEATURE:
<221> NAME/KEY: exon
<222> LOCATION: (1010)..(1166)
<220> FEATURE:
<221> NAME/KEY: Intron
<222> LOCATION: (1167)..(1218)
<223> OTHER INFORMATION: Intron 7
<220> FEATURE:
<221> NAME/KEY: exon
<222> LOCATION: (1219)..(1416)
<220> FEATURE:
<221> NAME/KEY: Intron
<222> LOCATION: (1417)..(1476)
<223> OTHER INFORMATION: Intron 8
<220> FEATURE:
<221> NAME/KEY: exon
<222> LOCATION: (1477)..(1740)
<220> FEATURE:
<221> NAME/KEY: Intron
<222> LOCATION: (1741)..(1796)
<223> OTHER INFORMATION: Intron 9
<220> FEATURE:
<221> NAME/KEY: exon
<222> LOCATION: (1797)..(2093)

<400> SEQUENCE: 6
```

```
atg gcg aag ttc caa tcg ttg ctc tcc tgc gtt acc ctc ctt ttc gcc        48
Met Ala Lys Phe Gln Ser Leu Leu Ser Cys Val Thr Leu Leu Phe Ala
1               5                   10                  15 gcc tcc gcc tat gcg ggc atc ggt ccc aag acc gac ctc acc att tcc        96
Ala Ser Ala Tyr Ala Gly Ile Gly Pro Lys Thr Asp Leu Thr Ile Ser
            20                  25                  30 aat gcg gac gtc gcc ccc gat ggc tat act cgt gct gcc gtt gtg gtc       144
Asn Ala Asp Val Ala Pro Asp Gly Tyr Thr Arg Ala Ala Val Val Val
        35                  40                  45 aac ggt gtc ttc cct gcc ccg ctc att aca ggg aat aag gtgggcggcg        193
Asn Gly Val Phe Pro Ala Pro Leu Ile Thr Gly Asn Lys
    50                  55                  60 tatcgccacc ctttttccccta agatgtccac taacatgccg gccatactgt tcaccag      250 gga gac cgc ttc cag ctc aat gtc att gac caa atg acg aac cac acg       298
Gly Asp Arg Phe Gln Leu Asn Val Ile Asp Gln Met Thr Asn His Thr
            65                  70                  75 atg ctg aag agc acc agc att gtacgctgtc ttcgattgct aaatcaatgt          349
Met Leu Lys Ser Thr Ser Ile
            80 ctcactcatt attttcccag cat tgg cat ggc ttt ttc cag aag ggc acg aac     402
                      His Trp His Gly Phe Phe Gln Lys Gly Thr Asn
                          85                  90                  95 tgg gct gac gga ccc gcc ttc atc aac cag tgt cca att tct agc ggg       450
Trp Ala Asp Gly Pro Ala Phe Ile Asn Gln Cys Pro Ile Ser Ser Gly
            100                 105                 110 cac tct ttc ctc tac gat ttc cag gtc ccg gac cag gcc g taagctata       500
His Ser Phe Leu Tyr Asp Phe Gln Val Pro Asp Gln Ala
            115                 120 tcattggtgg tgtgttgtac gctcgggtac tcacgccggt cgtgtag gc  acc ttt       555
                                                        Gly Thr Phe
                                                            125 tgg tac cac agc cac ctc tct aca cag tac tgc gat ggt ctc aga gga       603
Trp Tyr His Ser His Leu Ser Thr Gln Tyr Cys Asp Gly Leu Arg Gly
            130                 135                 140 cca ttt gtg gta tat gat ccg aag gat ccc ctc aag aag ctc tac gac      651
Pro Phe Val Val Tyr Asp Pro Lys Asp Pro Leu Lys Lys Leu Tyr Asp
            145                 150                 155 atc gat gac g gtcagttctt actgtcatta ctactgcaac tttgggtttg             701
Ile Asp Asp
160 tctgacgtct atttcacata g ac tcg acc gtg atc acc ctt acc gac tgg        751
                       Asp Ser Thr Val Ile Thr Leu Thr Asp Trp
                                165                 170 tat cac gtt gct gcc agg ctt gga ccg cgc ttc cc  gtgagtatct            796
Tyr His Val Ala Ala Arg Leu Gly Pro Arg Phe Pro
    175                 180 taccgctggc gcccatcgac gttcttctca cgaagaatat caatgctaat tcgacatggg    856 atgtag t ctc ggg tcg gac tcg act ctc att aac ggc ctt ggc cgt agc     905
         Leu Gly Ser Asp Ser Thr Leu Ile Asn Gly Leu Gly Arg Ser
             185                 190                 195 act acc aac gtc acg gct gac ctt gcc gtc ata aat gtc acg cag ggc      953
Thr Thr Asn Val Thr Ala Asp Leu Ala Val Ile Asn Val Thr Gln Gly
            200                 205                 210 aaa cg gtatatgcac tctcgacgtt aatgcaagag gatgctcact tctttaaata g     1009
Lys Arg
215 c tac cgc ttc cgc ctt gtg tcc ttg tca tgc gac ccc aac tac act ttc   1058
  Tyr Arg Phe Arg Leu Val Ser Leu Ser Cys Asp Pro Asn Tyr Thr Phe
      220                 225                 230
```

```
agc atc gac gac cat aac atg acc gtt ata gag gcg gat ggg att gaa      1106
Ser Ile Asp Asp His Asn Met Thr Val Ile Glu Ala Asp Gly Ile Glu
            235                 240                 245 act cag ccc gtg acc gtt aac gcc att cag att ttc tcc gct caa cgc      1154
Thr Gln Pro Val Thr Val Asn Ala Ile Gln Ile Phe Ser Ala Gln Arg
        250                 255                 260 tat tct ttc gtg gtaagtaatc ctcgtccgct ttttgacgct gaagctaaat          1206
Tyr Ser Phe Val
265 ggtctcttct ag cta act gca aac cag acg att gac aac tac tgg atc cgt    1257
              Leu Thr Ala Asn Gln Thr Ile Asp Asn Tyr Trp Ile Arg
                  270                 275                 280 gcc aac ccg aac ttt ggt aac gtt ggt ttc acg gat gga atc aac tct      1305
Ala Asn Pro Asn Phe Gly Asn Val Gly Phe Thr Asp Gly Ile Asn Ser
                285                 290                 295 gcc atc ctg cgc tac gcg gga gcg gac ccc gtc gag cca acg aca tcc      1353
Ala Ile Leu Arg Tyr Ala Gly Ala Asp Pro Val Glu Pro Thr Thr Ser
            300                 305                 310 caa caa acg aca cag aac ctg ctt aat gag gtc gac ctc cac ccc ttt      1401
Gln Gln Thr Thr Gln Asn Leu Leu Asn Glu Val Asp Leu His Pro Phe
        315                 320                 325 gtc ccc aaa cgc acg gtacgtgata cgttcaatgc atgaaacaat gttcaatact      1456
Val Pro Lys Arg Thr
330 tatgacatct ctttctccag cct ggc cag cct acg cag ggt ggt gtc gat acg    1509
                      Pro Gly Gln Pro Thr Gln Gly Gly Val Asp Thr
                                  335                 340                 345 gcc atc aac atg gtc ttc aac ttc aac ggc tcg aat ttc ttc atc aac      1557
Ala Ile Asn Met Val Phe Asn Phe Asn Gly Ser Asn Phe Phe Ile Asn
                350                 355                 360 aac gca tcc ttt gta cct ccc act gtt ccc gtc ctc ctc cag att ttg      1605
Asn Ala Ser Phe Val Pro Pro Thr Val Pro Val Leu Leu Gln Ile Leu
            365                 370                 375 agt ggg gcg cag gct gcc cag gat ctc ttg cca tct gga agc gtc tac      1653
Ser Gly Ala Gln Ala Ala Gln Asp Leu Leu Pro Ser Gly Ser Val Tyr
        380                 385                 390 aca ctg ccg gtc aac aag tct atc gag ctc acc ttc ccc gca acg gcc      1701
Thr Leu Pro Val Asn Lys Ser Ile Glu Leu Thr Phe Pro Ala Thr Ala
    395                 400                 405 aac gct cct gga gct ccc cat ccc ttc cac ttg cac ggt gtaagtccac       1750
Asn Ala Pro Gly Ala Pro His Pro Phe His Leu His Gly
410                 415                 420 cacacatcta ttcgacacca cacactcacc tcttctcccc ccacag cac gcc ttc       1805
                                                   His Ala Phe
                                                           425 gct gtg gtc cgc agc gca ggt tcc acc gtg tac aac tat gac aac cct      1853
Ala Val Val Arg Ser Ala Gly Ser Thr Val Tyr Asn Tyr Asp Asn Pro
                430                 435                 440 gtc tgg cgg gac gtc gtc tcc acg ggc acc ccc gcg gcg ggc gac aac      1901
Val Trp Arg Asp Val Val Ser Thr Gly Thr Pro Ala Ala Gly Asp Asn
            445                 450                 455 gtc acg atc cgc ttc cag acc gac aac ccc ggt ccg tgg ttc ctc cac      1949
Val Thr Ile Arg Phe Gln Thr Asp Asn Pro Gly Pro Trp Phe Leu His
        460                 465                 470 tgc cac atc gac ttc cac ctc gag gcc ggc ttc gcc gtc gtg ttc gcc      1997
Cys His Ile Asp Phe His Leu Glu Ala Gly Phe Ala Val Val Phe Ala
    475                 480                 485 gaa gac ccc acc gac acc tcc cta gca aac cct gtg ccg aag gcg tgg      2045
Glu Asp Pro Thr Asp Thr Ser Leu Ala Asn Pro Val Pro Lys Ala Trp
```

```
                 490                 495                 500                 505
tcg gat ctc tgc ccg acg tac gac gcg ctc tcg gtc gat gat caa tga          2093
Ser Asp Leu Cys Pro Thr Tyr Asp Ala Leu Ser Val Asp Asp Gln
                510                 515                 520

<210> SEQ ID NO 7
<211> LENGTH: 9
<212> TYPE: PRT
<213> ORGANISM: Saccharomyces cerevisiae
<220> FEATURE:
<221> NAME/KEY: PEPTIDE
<222> LOCATION: (1)..(9)
<223> OTHER INFORMATION: alpha-mating factor pre pro peptide

<400> SEQUENCE: 7

Met Arg Ile Arg His Arg Ser Gln Asp
1               5

<210> SEQ ID NO 8
<211> LENGTH: 1563
<212> TYPE: DNA
<213> ORGANISM: Ganoderma lucidum
<220> FEATURE:
<221> NAME/KEY: CDS
<222> LOCATION: (1)..(1563)
<223> OTHER INFORMATION: LacGL1 cDNA

<400> SEQUENCE: 8 atg gcg aag ttc caa tcg ttg ctc tcc tgc gtt acc ctc ctt ttc gcc           48
Met Ala Lys Phe Gln Ser Leu Leu Ser Cys Val Thr Leu Leu Phe Ala
1               5                   10                  15 gcc tcc gcc tat gcg ggc atc ggt ccc aag acc gac ctc acc att tcc           96
Ala Ser Ala Tyr Ala Gly Ile Gly Pro Lys Thr Asp Leu Thr Ile Ser
                20                  25                  30 aat gcg gac gtc gcc ccc gat ggc tat act cgt gct gcc gtt gtg gtc          144
Asn Ala Asp Val Ala Pro Asp Gly Tyr Thr Arg Ala Ala Val Val Val
            35                  40                  45 aac ggt gtc ttc cct gcc ccg ctc att aca ggg aat aag gga gac cgc          192
Asn Gly Val Phe Pro Ala Pro Leu Ile Thr Gly Asn Lys Gly Asp Arg
        50                  55                  60 ttc cag ctc aat gtc att gac caa atg acg aac cac acg atg ctg aag          240
Phe Gln Leu Asn Val Ile Asp Gln Met Thr Asn His Thr Met Leu Lys
65                  70                  75                  80 agc acc agc att cat tgg cat ggc ttt ttc cag aag ggc acg aac tgg          288
Ser Thr Ser Ile His Trp His Gly Phe Phe Gln Lys Gly Thr Asn Trp
                85                  90                  95 gct gac gga ccc gcc ttc atc aac cag tgt cca att tct agc ggg cac          336
Ala Asp Gly Pro Ala Phe Ile Asn Gln Cys Pro Ile Ser Ser Gly His
                100                 105                 110 tct ttc ctc tac gat ttc cag gtc ccg gac cag gcc ggc acc ttt tgg          384
Ser Phe Leu Tyr Asp Phe Gln Val Pro Asp Gln Ala Gly Thr Phe Trp
            115                 120                 125 tac cac agc cac ctc tct aca cag tac tgc gat ggt ctc aga gga cca          432
Tyr His Ser His Leu Ser Thr Gln Tyr Cys Asp Gly Leu Arg Gly Pro
        130                 135                 140 ttt gtg gta tat gat ccg aag gat ccc ctc aag aag ctc tac gac atc          480
Phe Val Val Tyr Asp Pro Lys Asp Pro Leu Lys Lys Leu Tyr Asp Ile
145                 150                 155                 160 gat gac gac tcg acc gtg atc acc ctt acc gac tgg tat cac gtt gct          528
Asp Asp Asp Ser Thr Val Ile Thr Leu Thr Asp Trp Tyr His Val Ala
                165                 170                 175 gcc agg ctt gga ccg cgc ttc cct ctc ggg tcg gac tcg act ctc att          576
Ala Arg Leu Gly Pro Arg Phe Pro Leu Gly Ser Asp Ser Thr Leu Ile
```

```
                    180                 185                 190
aac ggc ctt ggc cgt agc act acc aac gtc acg gct gac ctt gcc gtc         624
Asn Gly Leu Gly Arg Ser Thr Thr Asn Val Thr Ala Asp Leu Ala Val
            195                 200                 205 ata aat gtc acg cag ggc aaa cgc tac cgc ttc cgc ctt gtg tcc ttg         672
Ile Asn Val Thr Gln Gly Lys Arg Tyr Arg Phe Arg Leu Val Ser Leu
    210                 215                 220 tca tgc gac ccc aac tac act ttc agc atc gac gac cat aac atg acc         720
Ser Cys Asp Pro Asn Tyr Thr Phe Ser Ile Asp Asp His Asn Met Thr
225                 230                 235                 240 gtt ata gag gcg gat ggg att gaa act cag ccc gtg acc gtt aac gcc         768
Val Ile Glu Ala Asp Gly Ile Glu Thr Gln Pro Val Thr Val Asn Ala
                245                 250                 255 att cag att ttc tcc gct caa cgc tat tct ttc gtg cta act gca aac         816
Ile Gln Ile Phe Ser Ala Gln Arg Tyr Ser Phe Val Leu Thr Ala Asn
            260                 265                 270 cag acg att gac aac tac tgg atc cgt gcc aac ccg aac ttt ggt aac         864
Gln Thr Ile Asp Asn Tyr Trp Ile Arg Ala Asn Pro Asn Phe Gly Asn
    275                 280                 285 gtt ggt ttc acg gat gga atc aac tct gcc atc ctg cgc tac gcg gga         912
Val Gly Phe Thr Asp Gly Ile Asn Ser Ala Ile Leu Arg Tyr Ala Gly
290                 295                 300 gcg gac ccc gtc gag cca acg aca tcc caa caa acg aca cag aac ctg         960
Ala Asp Pro Val Glu Pro Thr Thr Ser Gln Gln Thr Thr Gln Asn Leu
305                 310                 315                 320 ctt aat gag gtc gac ctc cac ccc ttt gtc ccc aaa cgc acg cct ggc        1008
Leu Asn Glu Val Asp Leu His Pro Phe Val Pro Lys Arg Thr Pro Gly
                325                 330                 335 cag cct acg cag ggt ggt gtc gat acg gcc atc aac atg gtc ttc aac        1056
Gln Pro Thr Gln Gly Gly Val Asp Thr Ala Ile Asn Met Val Phe Asn
            340                 345                 350 ttc aac ggc tcg aat ttc ttc atc aac aac gca tcc ttt gta cct ccc        1104
Phe Asn Gly Ser Asn Phe Phe Ile Asn Asn Ala Ser Phe Val Pro Pro
    355                 360                 365 act gtt ccc gtc ctc ctc cag att ttg agt ggg gcg cag gct gcc cag        1152
Thr Val Pro Val Leu Leu Gln Ile Leu Ser Gly Ala Gln Ala Ala Gln
370                 375                 380 gat ctc ttg cca tct gga agc gtc tac aca ctg ccg gtc aac aag tct        1200
Asp Leu Leu Pro Ser Gly Ser Val Tyr Thr Leu Pro Val Asn Lys Ser
385                 390                 395                 400 atc gag ctc acc ttc ccc gca acg gcc aac gct cct gga gct ccc cat        1248
Ile Glu Leu Thr Phe Pro Ala Thr Ala Asn Ala Pro Gly Ala Pro His
                405                 410                 415 ccc ttc cac ttg cac ggt cac gcc ttc gct gtg gtc cgc agc gca ggt        1296
Pro Phe His Leu His Gly His Ala Phe Ala Val Val Arg Ser Ala Gly
            420                 425                 430 tcc acc gtg tac aac tat gac aac cct gtc tgg cgg gac gtc gtc tcc        1344
Ser Thr Val Tyr Asn Tyr Asp Asn Pro Val Trp Arg Asp Val Val Ser
    435                 440                 445 acg ggc acc ccc gcc gcg ggc gac aac gtc acg atc cgc ttc cag acc        1392
Thr Gly Thr Pro Ala Ala Gly Asp Asn Val Thr Ile Arg Phe Gln Thr
450                 455                 460 gac aac ccc ggt ccg tgg ttc ctc cac tgc cac atc gac ttc cac ctc        1440
Asp Asn Pro Gly Pro Trp Phe Leu His Cys His Ile Asp Phe His Leu
465                 470                 475                 480 gag gcc ggc ttc gcc gtc gtg ttc gcc gaa gac ccc acc gac acc tcc        1488
Glu Ala Gly Phe Ala Val Val Phe Ala Glu Asp Pro Thr Asp Thr Ser
                485                 490                 495 cta gca aac cct gtg ccg aag gcg tgg tcg gat ctc tgc ccg acg tac        1536
```

```
Leu Ala Asn Pro Val Pro Lys Ala Trp Ser Asp Leu Cys Pro Thr Tyr
            500                 505                 510 gac gcg ctc tcg gtc gat gat caa tga                              1563
Asp Ala Leu Ser Val Asp Asp Gln
            515                 520
```

<210> SEQ ID NO 9
<211> LENGTH: 520
<212> TYPE: PRT
<213> ORGANISM: Ganoderma lucidum

<400> SEQUENCE: 9

```
Met Ala Lys Phe Gln Ser Leu Leu Ser Cys Val Thr Leu Leu Phe Ala
1               5                   10                  15

Ala Ser Ala Tyr Ala Gly Ile Gly Pro Lys Thr Asp Leu Thr Ile Ser
            20                  25                  30

Asn Ala Asp Val Ala Pro Asp Gly Tyr Thr Arg Ala Ala Val Val Val
        35                  40                  45

Asn Gly Val Phe Pro Ala Pro Leu Ile Thr Gly Asn Lys Gly Asp Arg
    50                  55                  60

Phe Gln Leu Asn Val Ile Asp Gln Met Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Ile Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Lys Asp Pro Leu Lys Lys Leu Tyr Asp Ile
145                 150                 155                 160

Asp Asp Asp Ser Thr Val Ile Thr Leu Thr Asp Trp Tyr His Val Ala
                165                 170                 175

Ala Arg Leu Gly Pro Arg Phe Pro Leu Gly Ser Asp Ser Thr Leu Ile
            180                 185                 190

Asn Gly Leu Gly Arg Ser Thr Thr Asn Val Thr Ala Asp Leu Ala Val
        195                 200                 205

Ile Asn Val Thr Gln Gly Lys Arg Tyr Arg Phe Arg Leu Val Ser Leu
    210                 215                 220

Ser Cys Asp Pro Asn Tyr Thr Phe Ser Ile Asp Asp His Asn Met Thr
225                 230                 235                 240

Val Ile Glu Ala Asp Gly Ile Glu Thr Gln Pro Val Thr Val Asn Ala
                245                 250                 255

Ile Gln Ile Phe Ser Ala Gln Arg Tyr Ser Phe Val Leu Thr Ala Asn
            260                 265                 270

Gln Thr Ile Asp Asn Tyr Trp Ile Arg Ala Asn Pro Asn Phe Gly Asn
        275                 280                 285

Val Gly Phe Thr Asp Gly Ile Asn Ser Ala Ile Leu Arg Tyr Ala Gly
    290                 295                 300

Ala Asp Pro Val Glu Pro Thr Thr Ser Gln Thr Thr Gln Asn Leu
305                 310                 315                 320

Leu Asn Glu Val Asp Leu His Pro Phe Val Pro Lys Arg Thr Pro Gly
                325                 330                 335

Gln Pro Thr Gln Gly Gly Val Asp Thr Ala Ile Asn Met Val Phe Asn
```

```
              340                 345                 350
Phe Asn Gly Ser Asn Phe Phe Ile Asn Asn Ala Ser Phe Val Pro Pro
            355                 360                 365

Thr Val Pro Val Leu Leu Gln Ile Leu Ser Gly Ala Gln Ala Ala Gln
        370                 375                 380

Asp Leu Leu Pro Ser Gly Ser Val Tyr Thr Leu Pro Val Asn Lys Ser
385                 390                 395                 400

Ile Glu Leu Thr Phe Pro Ala Thr Ala Asn Ala Pro Gly Ala Pro His
                405                 410                 415

Pro Phe His Leu His Gly His Ala Phe Ala Val Val Arg Ser Ala Gly
                420                 425                 430

Ser Thr Val Tyr Asn Tyr Asp Asn Pro Val Trp Arg Asp Val Val Ser
            435                 440                 445

Thr Gly Thr Pro Ala Ala Gly Asp Asn Val Thr Ile Arg Phe Gln Thr
        450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Pro Thr Asp Thr Ser
                485                 490                 495

Leu Ala Asn Pro Val Pro Lys Ala Trp Ser Asp Leu Cys Pro Thr Tyr
                500                 505                 510

Asp Ala Leu Ser Val Asp Asp Gln
            515                 520

<210> SEQ ID NO 10
<211> LENGTH: 526
<212> TYPE: PRT
<213> ORGANISM: Ganoderma lucidum
<220> FEATURE:
<221> NAME/KEY: mat_peptide
<222> LOCATION: (1)..(526)
<223> OTHER INFORMATION: Recombinant mature LacGL1

<400> SEQUENCE: 10

Gly Ile Gly Pro Lys Thr Asp Leu Thr Ile Ser Asn Ala Asp Val Ala
1               5                   10                  15

Pro Asp Gly Tyr Thr Arg Ala Ala Val Val Asn Gly Val Phe Pro Pro
                20                  25                  30

Ala Pro Leu Ile Thr Gly Asn Lys Gly Asp Arg Phe Gln Leu Asn Val
            35                  40                  45

Ile Asp Gln Met Thr Asn His Thr Met Leu Lys Ser Thr Ser Ile His
        50                  55                  60

Trp His Gly Phe Phe Gln Lys Gly Thr Asn Trp Ala Asp Gly Pro Ala
65                  70                  75                  80

Phe Ile Asn Gln Cys Pro Ile Ser Ser Gly His Ser Phe Leu Tyr Asp
                85                  90                  95

Phe Gln Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
            115                 120                 125

Pro Lys Asp Pro Leu Lys Lys Leu Tyr Asp Ile Asp Asp Ser Thr
        130                 135                 140

Val Ile Thr Leu Thr Asp Trp Tyr His Val Ala Ala Arg Leu Gly Pro
145                 150                 155                 160

Arg Phe Pro Leu Gly Ser Asp Ser Thr Leu Ile Asn Gly Leu Gly Arg
                165                 170                 175
```

Ser Thr Thr Asn Val Thr Ala Asp Leu Ala Val Ile Asn Val Thr Gln
              180                 185                 190

Gly Lys Arg Tyr Arg Phe Arg Leu Val Ser Leu Ser Cys Asp Pro Asn
        195                 200                 205

Tyr Thr Phe Ser Ile Asp Asp His Asn Met Thr Val Ile Glu Ala Asp
    210                 215                 220

Gly Ile Glu Thr Gln Pro Val Thr Val Asn Ala Ile Gln Ile Phe Ser
225                 230                 235                 240

Ala Gln Arg Tyr Ser Phe Val Leu Thr Ala Asn Gln Thr Ile Asp Asn
                245                 250                 255

Tyr Trp Ile Arg Ala Asn Pro Asn Phe Gly Asn Val Gly Phe Thr Asp
                260                 265                 270

Gly Ile Asn Ser Ala Ile Leu Arg Tyr Ala Gly Ala Asp Pro Val Glu
            275                 280                 285

Pro Thr Thr Ser Gln Gln Thr Thr Gln Asn Leu Leu Asn Glu Val Asp
    290                 295                 300

Leu His Pro Phe Val Pro Lys Arg Thr Pro Gly Gln Pro Thr Gln Gly
305                 310                 315                 320

Gly Val Asp Thr Ala Ile Asn Met Val Phe Asn Phe Asn Gly Ser Asn
                325                 330                 335

Phe Phe Ile Asn Asn Ala Ser Phe Val Pro Pro Thr Val Pro Val Leu
                340                 345                 350

Leu Gln Ile Leu Ser Gly Ala Gln Ala Ala Gln Asp Leu Leu Pro Ser
            355                 360                 365

Gly Ser Val Tyr Thr Leu Pro Val Asn Lys Ser Ile Glu Leu Thr Phe
    370                 375                 380

Pro Ala Thr Ala Asn Ala Pro Gly Ala Pro His Pro Phe His Leu His
385                 390                 395                 400

Gly His Ala Phe Ala Val Val Arg Ser Ala Gly Ser Thr Val Tyr Asn
                405                 410                 415

Tyr Asp Asn Pro Val Trp Arg Asp Val Val Ser Thr Gly Thr Pro Ala
                420                 425                 430

Ala Gly Asp Asn Val Thr Ile Arg Phe Gln Thr Asp Asn Pro Gly Pro
            435                 440                 445

Trp Phe Leu His Cys His Ile Asp Phe His Leu Glu Ala Gly Phe Ala
    450                 455                 460

Val Val Phe Ala Glu Asp Pro Thr Asp Thr Ser Leu Ala Asn Pro Val
465                 470                 475                 480

Pro Lys Ala Trp Ser Asp Leu Cys Pro Thr Tyr Asp Ala Leu Ser Val
                485                 490                 495

Asp Asp Gln Ala Ala Ser Phe Leu Glu Gln Lys Leu Ile Ser Glu
                500                 505                 510

Glu Asp Leu Asn Ser Ala Val Asp His His His His His
        515                 520                 525

<210> SEQ ID NO 11
<211> LENGTH: 12
<212> TYPE: PRT
<213> ORGANISM: Ganoderma lucidum
<220> FEATURE:
<221> NAME/KEY: PEPTIDE
<222> LOCATION: (1)..(12)
<223> OTHER INFORMATION: LacGL1 peptide amino acid residues 88-100

<400> SEQUENCE: 11

Thr Thr Ser Ile His Trp His Gly Phe Phe Gln Lys
1               5                   10

<210> SEQ ID NO 12
<211> LENGTH: 18
<212> TYPE: PRT
<213> ORGANISM: Ganoderma lucidum
<220> FEATURE:
<221> NAME/KEY: PEPTIDE
<222> LOCATION: (1)..(18)
<223> OTHER INFORMATION: LacGL1 peptide amino acid residues 245-263

<400> SEQUENCE: 12

Asp Asp Asp Ser Thr Val Leu Thr Leu Ala Asp Trp Tyr His Val Ala
1               5                   10                  15

Ala Arg

<210> SEQ ID NO 13
<211> LENGTH: 14
<212> TYPE: PRT
<213> ORGANISM: Ganoderma lucidum
<220> FEATURE:
<221> NAME/KEY: PEPTIDE
<222> LOCATION: (1)..(14)
<223> OTHER INFORMATION: LacGL1 peptide amino acid residues 452-466

<400> SEQUENCE: 13

Thr Leu Ser Asn Ala Asp Ile Ala Pro Asp Gly Phe Thr Arg
1               5                   10

<210> SEQ ID NO 14
<211> LENGTH: 12
<212> TYPE: PRT
<213> ORGANISM: Ganoderma lucidum
<220> FEATURE:
<221> NAME/KEY: PEPTIDE
<222> LOCATION: (1)..(12)
<223> OTHER INFORMATION: LacGL1 peptide amino acid residues 185-197

<400> SEQUENCE: 14

Gly Ser Asp Ser Thr Leu Ile Asn Gly Leu Gly Arg
1               5                   10

<210> SEQ ID NO 15
<211> LENGTH: 18
<212> TYPE: DNA
<213> ORGANISM: Ganoderma lucidum
<220> FEATURE:
<221> NAME/KEY: primer_bind
<222> LOCATION: (1)..(18)
<223> OTHER INFORMATION: WADGP_fwd3 primer

<400> SEQUENCE: 15
ctgggcggat ggtcccgc                                                 18

<210> SEQ ID NO 16
<211> LENGTH: 20
<212> TYPE: DNA
<213> ORGANISM: Ganoderma lucidum
<220> FEATURE:
<221> NAME/KEY: primer_bind
<222> LOCATION: (1)..(20)
<223> OTHER INFORMATION: LINGLP_rev1 primer

<400> SEQUENCE: 16
cggccaaggc cattgatgag                                               20

```
<210> SEQ ID NO 17
<211> LENGTH: 23
<212> TYPE: DNA
<213> ORGANISM: Ganoderma lucidum
<220> FEATURE:
<221> NAME/KEY: primer_bind
<222> LOCATION: (1)..(23)
<223> OTHER INFORMATION: QYCDGLR_fwd1 primer

<400> SEQUENCE: 17
cagtactgcg acggtctaag agg                                              23

<210> SEQ ID NO 18
<211> LENGTH: 23
<212> TYPE: DNA
<213> ORGANISM: Ganoderma lucidum
<220> FEATURE:
<221> NAME/KEY: primer_bind
<222> LOCATION: (1)..(23)
<223> OTHER INFORMATION: YHSHLST_rev1 primer

<400> SEQUENCE: 18
ggtggagaga tgactgtggt acc                                              23

<210> SEQ ID NO 19
<211> LENGTH: 23
<212> TYPE: DNA
<213> ORGANISM: Ganoderma lucidum
<220> FEATURE:
<221> NAME/KEY: primer_bind
<222> LOCATION: (1)..(23)
<223> OTHER INFORMATION: IAPDGFT_fwd1 primer

<400> SEQUENCE: 19
catcgctccc gatggcttca ctc                                              23

<210> SEQ ID NO 20
<211> LENGTH: 21
<212> TYPE: DNA
<213> ORGANISM: Ganoderma lucidum
<220> FEATURE:
<221> NAME/KEY: primer_bind
<222> LOCATION: (1)..(21)
<223> OTHER INFORMATION: DLCTS_rev1 primer

<400> SEQUENCE: 20
ctgacgtcgg gcaaagatcc g                                                21

<210> SEQ ID NO 21
<211> LENGTH: 25
<212> TYPE: DNA
<213> ORGANISM: Ganoderma lucidum
<220> FEATURE:
<221> NAME/KEY: primer_bind
<222> LOCATION: (1)..(25)
<223> OTHER INFORMATION: SLANPVPK_rev primer

<400> SEQUENCE: 21
cttcggcaca gggtttgcta gggag                                            25

<210> SEQ ID NO 22
<211> LENGTH: 24
<212> TYPE: DNA
<213> ORGANISM: Ganoderma lucidum
<220> FEATURE:
<221> NAME/KEY: primer_bind
<222> LOCATION: (1)..(24)
<223> OTHER INFORMATION: QKGTNWAD_fwd primer
```

```
<400> SEQUENCE: 22
cagaagggca cgaactgggc tgac                                           24

<210> SEQ ID NO 23
<211> LENGTH: 41
<212> TYPE: DNA
<213> ORGANISM: Ganoderma lucidum
<220> FEATURE:
<221> NAME/KEY: primer_bind
<222> LOCATION: (1)..(41)
<223> OTHER INFORMATION: LSVDDQ_rev primer

<400> SEQUENCE: 23
tagcgcggcc gcctattatc attgatcatc gaccgagagc g                        41

<210> SEQ ID NO 24
<211> LENGTH: 32
<212> TYPE: DNA
<213> ORGANISM: Ganoderma lucidum
<220> FEATURE:
<221> NAME/KEY: primer_bind
<222> LOCATION: (1)..(32)
<223> OTHER INFORMATION: MAKFQSL_fwd primer

<400> SEQUENCE: 24
atgcgaattc atggcgaagt tccaatcgtt gc                                  32

<210> SEQ ID NO 25
<211> LENGTH: 28
<212> TYPE: DNA
<213> ORGANISM: Saccharomyces cerevisiae
<220> FEATURE:
<221> NAME/KEY: primer_bind
<222> LOCATION: (1)..(28)
<223> OTHER INFORMATION: alpha-FACTOR_fwd primer

<400> SEQUENCE: 25
atgcgaattc ggcatcggtc ccaagacc                                       28

<210> SEQ ID NO 26
<211> LENGTH: 45
<212> TYPE: DNA
<213> ORGANISM: Ganoderma lucidum
<220> FEATURE:
<221> NAME/KEY: primer_bind
<222> LOCATION: (1)..(45)
<223> OTHER INFORMATION: Universal Primer - long

<400> SEQUENCE: 26
ctaatacgac tcactatagg gcaagcagtg gtatcaacgc agagt                    45

<210> SEQ ID NO 27
<211> LENGTH: 22
<212> TYPE: DNA
<213> ORGANISM: Ganoderma lucidum
<220> FEATURE:
<221> NAME/KEY: primer_bind
<222> LOCATION: (1)..(22)
<223> OTHER INFORMATION: Universal Primer - short

<400> SEQUENCE: 27
ctaatacgac tcactatagg gc                                             22

<210> SEQ ID NO 28
<211> LENGTH: 1563
<212> TYPE: DNA
<213> ORGANISM: Ganoderma lucidum
```

```
<220> FEATURE:
<221> NAME/KEY: CDS
<222> LOCATION: (1)..(1563)
<223> OTHER INFORMATION: GL1ac1 cDNA encoding signal peptide (1-63bp)
      and mature polypepetide (64-1560)

<400> SEQUENCE: 28 atg gtg aaa ttc caa tcg ttg ctc tcc tgc gtc acc ctt ctt ttc gcc      48
Met Val Lys Phe Gln Ser Leu Leu Ser Cys Val Thr Leu Leu Phe Ala
1               5                   10                  15 gcc tca gcc cat gcg ggc att ggc ccc aag gcc gac ctt acc att tcc      96
Ala Ser Ala His Ala Gly Ile Gly Pro Lys Ala Asp Leu Thr Ile Ser
            20                  25                  30 aac gcg aac atc gcc cct gat ggc tac acc cgt gcc gcc gtt gtg gtg     144
Asn Ala Asn Ile Ala Pro Asp Gly Tyr Thr Arg Ala Ala Val Val Val
        35                  40                  45 aat ggt gtc ttc cct ggg ccg ctc atc aca ggg aac aag gga gac cgt     192
Asn Gly Val Phe Pro Gly Pro Leu Ile Thr Gly Asn Lys Gly Asp Arg
    50                  55                  60 ttc cag ctg aat gtc atc gac caa ctg acg aac cac aca atg ctg aag     240
Phe Gln Leu Asn Val Ile Asp Gln Leu Thr Asn His Thr Met Leu Lys
65                  70                  75                  80 acc acc agc att cat tgg cat ggc ttt ttc cag aag ggc acg aac tgg     288
Thr Thr Ser Ile His Trp His Gly Phe Phe Gln Lys Gly Thr Asn Trp
                85                  90                  95 gcg gat ggt ccc gcg ttc atc aac cag tgt ccg att gct agc ggg cac     336
Ala Asp Gly Pro Ala Phe Ile Asn Gln Cys Pro Ile Ala Ser Gly His
            100                 105                 110 tcg ttc ctc tac gat ttc cag gtt ccg gat cag gcc ggc act ttt tgg     384
Ser Phe Leu Tyr Asp Phe Gln Val Pro Asp Gln Ala Gly Thr Phe Trp
        115                 120                 125 tac cac agc cat ctc tcc acg cag tac tgt gac ggt ctc agg ggt cca     432
Tyr His Ser His Leu Ser Thr Gln Tyr Cys Asp Gly Leu Arg Gly Pro
    130                 135                 140 ttc gtg gta tat gac cct aag gac ccc ctc aag gga ctg tac gac gtc     480
Phe Val Val Tyr Asp Pro Lys Asp Pro Leu Lys Gly Leu Tyr Asp Val
145                 150                 155                 160 gac aac gac tcg act gtg atc acc ctc tcc gac tgg tat cac gtg gct     528
Asp Asn Asp Ser Thr Val Ile Thr Leu Ser Asp Trp Tyr His Val Ala
                165                 170                 175 gcc agg ctt gga ccg agc ttc ccg ctc ggc tcg gac tcg act ctc atc     576
Ala Arg Leu Gly Pro Ser Phe Pro Leu Gly Ser Asp Ser Thr Leu Ile
            180                 185                 190 aat ggc ctt ggc cgt agc act acc aac gct acc gcc ggc ctc gct gtt     624
Asn Gly Leu Gly Arg Ser Thr Thr Asn Ala Thr Ala Gly Leu Ala Val
        195                 200                 205 atc aac gtc aca cag ggc aaa cgt tat cgc ttc cgc ctt gtg tcc ttg     672
Ile Asn Val Thr Gln Gly Lys Arg Tyr Arg Phe Arg Leu Val Ser Leu
    210                 215                 220 tca tgc gac ccc aac tac acc ttc agc atc gac ggc cat gac atg tcc     720
Ser Cys Asp Pro Asn Tyr Thr Phe Ser Ile Asp Gly His Asp Met Ser
225                 230                 235                 240 gtt att gag gcg gat ggt att gca acg caa ccc gtg acc gcg aac gct     768
Val Ile Glu Ala Asp Gly Ile Ala Thr Gln Pro Val Thr Ala Asn Ala
                245                 250                 255 att caa atc ttc tct gct caa cga tat tct ttc gtg ctg act gca aat     816
Ile Gln Ile Phe Ser Ala Gln Arg Tyr Ser Phe Val Leu Thr Ala Asn
            260                 265                 270 cag aca att ggc aac tat tgg att cgc gcc aac ccg agc ttt gga aat     864
Gln Thr Ile Gly Asn Tyr Trp Ile Arg Ala Asn Pro Ser Phe Gly Asn
        275                 280                 285
```

-continued

```
att ggt ttc acg aat gga atc aac tct gcc atc ctg cgc tac tcg gga      912
Ile Gly Phe Thr Asn Gly Ile Asn Ser Ala Ile Leu Arg Tyr Ser Gly
    290                 295                 300 gcg gat ccc atc gaa cct acg acg gcc caa caa acc aca cag aac ctc      960
Ala Asp Pro Ile Glu Pro Thr Thr Ala Gln Gln Thr Thr Gln Asn Leu
305                 310                 315                 320 ctc aat gag gtc gac ctc cac ccc ttt gtc gct aaa cag acg cct ggc     1008
Leu Asn Glu Val Asp Leu His Pro Phe Val Ala Lys Gln Thr Pro Gly
                325                 330                 335 cgc gct aca cag ggt ggt acc gat gtg gcc atc aac atg gtc ttc aac     1056
Arg Ala Thr Gln Gly Gly Thr Asp Val Ala Ile Asn Met Val Phe Asn
            340                 345                 350 ttt aac ggc tcg aac ttc ttc atc aac aac gcg tcc ttc acg cct ccc     1104
Phe Asn Gly Ser Asn Phe Phe Ile Asn Asn Ala Ser Phe Thr Pro Pro
        355                 360                 365 act gtc ccc gtc ctc ctt cag att ttg agc ggc gca cag gcc gcc cag     1152
Thr Val Pro Val Leu Leu Gln Ile Leu Ser Gly Ala Gln Ala Ala Gln
370                 375                 380 gac ctc ctg cct tcc gga agt gtc tac acg ctg ccg atc aac aag tcc     1200
Asp Leu Leu Pro Ser Gly Ser Val Tyr Thr Leu Pro Ile Asn Lys Ser
385                 390                 395                 400 atc gag ctc acc ttc ccc gcc acg gtc aac gcc ccc ggg gct ccc cac     1248
Ile Glu Leu Thr Phe Pro Ala Thr Val Asn Ala Pro Gly Ala Pro His
                405                 410                 415 ccc ttc cac ctg cac ggt cat tcg ttc gct gtg gtc cgc agc gcc ggc     1296
Pro Phe His Leu His Gly His Ser Phe Ala Val Val Arg Ser Ala Gly
            420                 425                 430 tcc aca gaa tac aac tat aac aat ccc gta tgg cgc gac gtc gtt tcg     1344
Ser Thr Glu Tyr Asn Tyr Asn Asn Pro Val Trp Arg Asp Val Val Ser
        435                 440                 445 acc ggc acc cct gca gcg ggc gac aac gtc acg atc cgc ttc cag acc     1392
Thr Gly Thr Pro Ala Ala Gly Asp Asn Val Thr Ile Arg Phe Gln Thr
450                 455                 460 gac aac ccc gga ccg tgg ttc ctc cat tgc cac atc gac ttc cat ctc     1440
Asp Asn Pro Gly Pro Trp Phe Leu His Cys His Ile Asp Phe His Leu
465                 470                 475                 480 gag gcg ggc ttc gct gtc gtg ttc gcc gag gac acc gct gat act tct     1488
Glu Ala Gly Phe Ala Val Val Phe Ala Glu Asp Thr Ala Asp Thr Ser
                485                 490                 495 ctg gcg aac cat gtc cca caa gca tgg tcg gat ctt tgc ccg acg tac     1536
Leu Ala Asn His Val Pro Gln Ala Trp Ser Asp Leu Cys Pro Thr Tyr
            500                 505                 510 gat gcg ctc tcg gct gat gat cac tga                                  1563
Asp Ala Leu Ser Ala Asp Asp His
        515                 520

<210> SEQ ID NO 29
<211> LENGTH: 520
<212> TYPE: PRT
<213> ORGANISM: Ganoderma lucidum

<400> SEQUENCE: 29

Met Val Lys Phe Gln Ser Leu Leu Ser Cys Val Thr Leu Leu Phe Ala
1               5                   10                  15

Ala Ser Ala His Ala Gly Ile Gly Pro Lys Ala Asp Leu Thr Ile Ser
            20                  25                  30

Asn Ala Asn Ile Ala Pro Asp Gly Tyr Thr Arg Ala Ala Val Val Val
        35                  40                  45

Asn Gly Val Phe Pro Gly Pro Leu Ile Thr Gly Asn Lys Gly Asp Arg
```

-continued

```
                50                  55                  60
Phe Gln Leu Asn Val Ile Asp Gln Leu Thr Asn His Thr Met Leu Lys
 65                      70                  75                  80

Thr Thr Ser Ile His Trp His Gly Phe Phe Gln Lys Gly Thr Asn Trp
                         85                  90                  95

Ala Asp Gly Pro Ala Phe Ile Asn Gln Cys Pro Ile Ala Ser Gly His
                100                 105                 110

Ser Phe Leu Tyr Asp Phe Gln Val Pro Asp Gln Ala Gly Thr Phe Trp
                115                 120                 125

Tyr His Ser His Leu Ser Thr Gln Tyr Cys Asp Gly Leu Arg Gly Pro
                130                 135                 140

Phe Val Val Tyr Asp Pro Lys Asp Pro Leu Lys Gly Leu Tyr Asp Val
145                     150                 155                 160

Asp Asn Asp Ser Thr Val Ile Thr Leu Ser Asp Trp Tyr His Val Ala
                165                 170                 175

Ala Arg Leu Gly Pro Ser Phe Pro Leu Gly Ser Asp Ser Thr Leu Ile
                180                 185                 190

Asn Gly Leu Gly Arg Ser Thr Thr Asn Ala Thr Ala Gly Leu Ala Val
                195                 200                 205

Ile Asn Val Thr Gln Gly Lys Arg Tyr Arg Phe Arg Leu Val Ser Leu
210                     215                 220

Ser Cys Asp Pro Asn Tyr Thr Phe Ser Ile Asp Gly His Asp Met Ser
225                     230                 235                 240

Val Ile Glu Ala Asp Gly Ile Ala Thr Gln Pro Val Thr Ala Asn Ala
                245                 250                 255

Ile Gln Ile Phe Ser Ala Gln Arg Tyr Ser Phe Val Leu Thr Ala Asn
                260                 265                 270

Gln Thr Ile Gly Asn Tyr Trp Ile Arg Ala Asn Pro Ser Phe Gly Asn
                275                 280                 285

Ile Gly Phe Thr Asn Gly Ile Asn Ser Ala Ile Leu Arg Tyr Ser Gly
                290                 295                 300

Ala Asp Pro Ile Glu Pro Thr Thr Ala Gln Gln Thr Thr Gln Asn Leu
305                     310                 315                 320

Leu Asn Glu Val Asp Leu His Pro Phe Val Ala Lys Gln Thr Pro Gly
                325                 330                 335

Arg Ala Thr Gln Gly Gly Thr Asp Val Ala Ile Asn Met Val Phe Asn
                340                 345                 350

Phe Asn Gly Ser Asn Phe Phe Ile Asn Asn Ala Ser Phe Thr Pro Pro
                355                 360                 365

Thr Val Pro Val Leu Leu Gln Ile Leu Ser Gly Ala Gln Ala Ala Gln
                370                 375                 380

Asp Leu Leu Pro Ser Gly Ser Val Tyr Thr Leu Pro Ile Asn Lys Ser
385                     390                 395                 400

Ile Glu Leu Thr Phe Pro Ala Thr Val Asn Ala Pro Gly Ala Pro His
                405                 410                 415

Pro Phe His Leu His Gly His Ser Phe Ala Val Val Arg Ser Ala Gly
                420                 425                 430

Ser Thr Glu Tyr Asn Tyr Asn Pro Val Trp Arg Asp Val Val Ser
                435                 440                 445

Thr Gly Thr Pro Ala Ala Gly Asp Asn Val Thr Ile Arg Phe Gln Thr
                450                 455                 460

Asp Asn Pro Gly Pro Trp Phe Leu His Cys His Ile Asp Phe His Leu
465                     470                 475                 480
```

```
Glu Ala Gly Phe Ala Val Val Phe Ala Glu Asp Thr Ala Asp Thr Ser
            485                 490                 495

Leu Ala Asn His Val Pro Gln Ala Trp Ser Asp Leu Cys Pro Thr Tyr
            500                 505                 510

Asp Ala Leu Ser Ala Asp Asp His
            515                 520
```